US008206719B2

(12) United States Patent
Tahara et al.

(10) Patent No.: US 8,206,719 B2
(45) Date of Patent: Jun. 26, 2012

(54) KDR PEPTIDES AND VACCINES COMPRISING THE SAME

(75) Inventors: Hideaki Tahara, Meguro-ku (JP); Satoshi Wada, Meguro-ku (JP); Takuya Tsunoda, Minato-ku (JP)

(73) Assignee: Oncotherapy Science, Inc., Kanagawa (JP)

( * ) Notice: Subject to any disclaimer, the term of this patent is extended or adjusted under 35 U.S.C. 154(b) by 100 days.

(21) Appl. No.: 12/711,159

(22) Filed: Feb. 23, 2010

(65) Prior Publication Data

US 2010/0215676 A1    Aug. 26, 2010

Related U.S. Application Data

(62) Division of application No. 12/355,616, filed on Jan. 16, 2009, now Pat. No. 7,695,720, which is a division of application No. 10/527,496, filed as application No. PCT/JP03/11722 on Sep. 12, 2003, now Pat. No. 7,514,084.

(30) Foreign Application Priority Data

Sep. 12, 2002 (JP) ................ 2002-267285
Mar. 7, 2003 (JP) ................ 2003-062003
Jun. 11, 2003 (JP) ................ 2003-167042

(51) Int. Cl.
*A61K 38/04* (2006.01)
*A61K 38/08* (2006.01)
*A61K 38/10* (2006.01)
*A61K 38/17* (2006.01)
*C07K 7/06* (2006.01)
*C07K 7/08* (2006.01)
*C07K 4/12* (2006.01)
*C07K 14/705* (2006.01)

(52) U.S. Cl. ............ 424/185.1; 514/21.5; 514/21.6; 530/327; 530/328

(58) Field of Classification Search ............... None
See application file for complete search history.

(56) References Cited

U.S. PATENT DOCUMENTS

| | | | |
|---|---|---|---|
| 5,712,380 A | | 1/1998 | Kendall et al. |
| 5,766,860 A | * | 6/1998 | Terman et al. ............ 435/7.2 |
| 5,942,428 A | * | 8/1999 | Mohammadi et al. ........ 435/194 |
| 6,348,333 B1 | | 2/2002 | Niwa et al. |
| 6,897,294 B2 | * | 5/2005 | Davis-Smyth et al. ........ 530/350 |
| 7,514,084 B2 | * | 4/2009 | Tahara et al. ............ 424/185.1 |
| 7,556,809 B2 | | 7/2009 | Romero et al. |
| 7,695,720 B2 | * | 4/2010 | Tahara et al. ............ 424/185.1 |
| 2005/0187241 A1 | | 8/2005 | Wen et al. |
| 2008/0254050 A1 | | 10/2008 | Romero et al. |
| 2009/0036479 A1 | | 2/2009 | Wen et al. |
| 2009/0214581 A1 | | 8/2009 | Tahara et al. |
| 2010/0297157 A1 | | 11/2010 | Tamaki et al. |

FOREIGN PATENT DOCUMENTS

| | | |
|---|---|---|
| EP | 0 921 193 A1 | 6/1999 |
| EP | 1 055 684 A1 | 11/2000 |
| EP | 1 502 599 A1 | 2/2005 |
| JP | 2006-501145 A | 1/2006 |
| JP | 2006-511475 A | 4/2006 |
| WO | WO 94/11499 A1 | 5/1994 |
| WO | WO 94/21679 A1 | 9/1994 |
| WO | WO 96/26214 A1 | 8/1996 |
| WO | WO 98/11223 A1 | 3/1998 |
| WO | WO 98/31794 A1 | 7/1998 |
| WO | WO 98/58053 A1 | 12/1998 |
| WO | WO 99/40118 A1 | 8/1999 |
| WO | WO 99/43801 A1 | 9/1999 |
| WO | WO 99/59636 A1 | 11/1999 |
| WO | WO 01/12809 A2 | 2/2001 |
| WO | WO 02/056907 A2 | 7/2002 |
| WO | WO 02/056907 A3 | 7/2002 |
| WO | WO 03/086450 A1 | 10/2003 |
| WO | WO 2004/027027 A2 | 4/2004 |
| WO | WO 2008/099908 A1 | 8/2008 |
| WO | WO 2009/028150 A1 | 3/2009 |

OTHER PUBLICATIONS

Adams, H-P. et al., "Prediction of binding to MHC class I molecules," *Journal of Immunological Methods*, vol. 185(2), pp. 181-190 (Sep. 25, 1995).
Li, Yiwen et al.; "Active Immunization Against the Vascular Endothelial Growth Factor Receptor flk1 Inhibits Tumor Angiogenesis and Metastasis"; *J. Exp. Med.*; Jun. 17, 2002; pp. 1575-1584; vol. 195, No. 12.
Parker, K., et al., "Scheme for ranking potential HLA-A2 binding peptides based on independent binding of individual peptide side-chains," *Journal of Immunology*, vol. 152(1), pp. 163-175 (Jan. 1, 1994).
Schueler-Furman, O., et al., "Structure-based prediction of binding peptides to MHC class I molecules: Application to a broad range of MHC alleles," *Protein Science*, vol. 9(9), pp. 1838-1846(Sep. 2000).
Tokunaga, K., et al., "Sequence-based association analysis of HLA class I and II alleles in Japanese supports conservation of common haplotypes," *Immunogenetics*, vol. 46(3), pp. 199-205 (1997).
Baxevanus, Constantin et al.; "Immunogenic HER-2/neu peptides as tumor vaccines"; *Cancer Immunology, Immunotherapy*; 2006; pp. 85-95; vol. 55.
Bicknell, Roy et al.; "Mechanisms and therapeutic implications of angiogenesis" *Current Opinion in Oncology*; 1996; pp. 60-65; vol. 8.
Binétruy-Tournaire, Roselyne et al.; "Identification of a peptide blocking vascular endothelial growht factor (VEGF)-mediated angiogenesis"; *The EMBO Journal*; 2000; pp. 1525-1533; vol. 19, No. 7.
Bruns et al.; "Effect of the vascular endothelial growth factor receptor-2 antibody DC101 plus gemcitabine on growth, metastasis and angiogenesis of human pancreatic cancer growing orthotopically in nude mice"; *Int. J. Cancer*; 102: 101-108 (2002).

(Continued)

*Primary Examiner* — Phuong Huynh
(74) *Attorney, Agent, or Firm* — Kilpatrick Townsend & Stockton LLP

(57) ABSTRACT

The present invention provides nonapeptides selected from peptides comprising the amino acid sequence of SEQ ID NO:2, 3, 5, 8, 11, or 12; nonapeptides or decapeptides selected from peptides comprising the amino acid sequence of SEQ ID NO:29, 30, 33, 34, 40, or 46; and peptides with cytotoxic T cell inducibility, in which one, two, or several amino acids are substituted or added to the above-mentioned amino acid sequences, as well as pharmaceuticals for treating or preventing tumors, where the pharmaceuticals comprise these peptides. The peptides of this invention can be used as vaccines.

11 Claims, 32 Drawing Sheets

OTHER PUBLICATIONS

Flamme, Ingo, et al.; "Vascular endothelial growth factor (VEGF) and VEGF Receptor 2 (flk-1) are expressed during vasculogenesis and vascular differentiation in the quail embryo"; *Developmental Biology*; 1995; pp. 699-712; vol. 169.

Folkman, Judah; "Angiogenesis in cancer, vascular rheumatoid and other disease"; *Nature Medicine*; 1995; pp. 27-31; vol. 1, No. 1.

Huang, Xiaojun et al.; "Combined Therapy of Local and Metastatic 4T1 Breast Tumor in Mice Using SU6668, an Inhibitor of Angiogenic Receptor Tyrosine Kinases, and the Immunostimulator B7.2-IgG Fusion Protein"; *Cancer Research*; Oct. 15, 2002; pp. 5727-5735; vol. 62.

Hou et al.; "Combination of low-dose gemcitabine and recombinant quail vascular endothelial growth factor receptor-2 as a vaccine induces synergistic antitumor activities"; *Oncology*; 69: 81-87 (2005) *ePub* on Aug. 2, 2005.

Kindler et al.; "Phase II trial of bevacizumab plus gemcitabine in patients with advanced pancreatic cancer"; *J. Clin. Oncol.*; 23(31): 8033-8040 (2005).

Kondo, Akihiro et al.; "Prominent Roles of Secondary Anchor Reisues in Peptide Binding to HLA-A24 Human Class I Molecules"; *The Journal of Immunologl*; 1995; pp. 4307-4312; vol. 155.

Krause et al.; "Vascular endothelial growth factor antisense pretreatment of bladder cancer cells significantly enhances the cytotoxicity of mitomycin C, gemcitabine and cisplatin"; *J. Urology*; 174: 328-331 (2005).

Kubo, Ralph T. et al.; "Definition of Specific Peptide Motifs for Four Major HLA-A Alleles"; *Journal of Immunology*; 1994; pp. 3913-3924; vol. 152.

Leggatt, Graham et al.; "The importance of pairwise interactions between peptide residues in the delineation of TCR specificity"; *The Journal of Immunology*; 1998; pp. 4728-4735; vol. 161.

Mestas, Javier and C.C.W. Hughes; "Of mice and not men: Differences between Mouse and Human Immunology"; *The Journal of Immunology*; 2004; pp. 2731-2738; vol. 192.

Miyazawa et al.; "Combination therapy against pancreatic cancer using epitope peptide and gemcitabine in that the molecular target is VEGFR2"; *Suzio*; vol. 23, Abstract S-10 Jun. 1, 2008.

Norgren, R.B. et al.; "Kinase insert domain receptor"; Jun. 1, 2002; EMBL Accession No. Q8SPP1.

Rammensee, Hans-Georg et al.; "MHC ligands and peptide motifs: first listing"; *Immunogenetics*; 1995; pp. 178-228; vol. 41.

Wada, Satoshi et al.; "Development of cancer vaccine targeting tumor angiogenesis"; *Cancer Science (Proceedings of the 62nd Annual Meeting of the Japanese Cancer Association)*; Sep. 25-27, 2003, p. 202; Abstract 2267-OP.

Wada, et al.; "Development of a new type of cancer immunotherapy that targets tumor angiogenesis"; *The Japanese Journal of Gastroenterological Surgery*; 2003, p. 564, Abstract PP-2-606; vol. 36, No. 7.

Wada et al.; "Development of a cancer vaccine therapy that targets tumor angiogenesis"; *Journal of the Japanese Surgical Society*; 2003; p. 533, Abstract PS3124-3; vol. 104(Suppl.).

Wada, Satoshi et al.; "Development of cancer immunotherapy against tumor angiogenesis"; *Proceedings of the 94th Annual Meeting of the American Association for Cancer Research*; Jul. 11-14, 2003; p. 167, Abstract 848; Washington D.C. (The previously scheduled meeting on Apr. 5-9, 2003 in Toronto, Canada was postponed. A program from the April meeting is also enclosed).

Wada, Satoshi et al.; "Development of the new cancer vaccine treatment that can be opposed to escape mechanism of immunological"; *Cancer Science (Proceedings of the 63rd Annual Meeting of the Japanese Cancer Association)*; Sep. 29-Oct. 1, 2004, p. 436, Abstract W-464; vol. 95(Suppl).

Wada, Satoshi et al.; "Rationale for Antiangiogenic Cancer Therapy with Vaccination Using Eiptope Peptides Derived from Human Vascular Endothelial Growth Factor Receptor 2"; *Cancer Res.*; Jun. 1, 2005; pp. 4939-4936; vol. 65, No. 11.

Waltenberger, Johannes et al.; "Different Signal Transduction Properties of KDR and Flt1, Two Receptors for Vascular Endothelial Growth Factor"; *The Journal of Biological Chemistry*; Oct. 28, 1994; pp. 26988-26995; vol. 269, No. 43.

Zaremba et al.; "Identification of an enhancer agonist cytotoxic T lymphocyte peptide from human carcinoembryonic antigen"; 1997; *Cancer Res.*; vol. 57, pp. 4750-4757.

U.S. Appl. No. 12/674,754, filed Dec. 6, 2010, 53 pgs.

Hida et al.; "A simple culture protocol to detect peptide-specific cytotoxic T lymphocyte precursors in the circulation"; *Cancer Immunol. Immunother.*; 51:219-228 (2002).

Sadovnikova et al.; "Generation of human tumor-reactive cytotoxic T cells against peptides presented by non-self HLA class I molecules"; *Eur. J. Immunol.*; 28:193-200.

Database UniProt Accession No. Q9SX54; "Rabbit mRNA for vascular endothelial growth factor (VEGF) receptor 2/Flk-1, partial cds"; Umeki, K., et al.; 1998 (1 page).

* cited by examiner

ID NO:2, 3, 5, 8, 11, or 12.

```
                        SEQUENCE LISTING

<160> NUMBER OF SEQ ID NOS: 56

<210> SEQ ID NO 1
<211> LENGTH: 9
<212> TYPE: PRT
<213> ORGANISM: Homo sapiens

<400> SEQUENCE: 1

Trp Tyr Lys Leu Gly Pro Gln Pro Leu
 1               5

<210> SEQ ID NO 2
<211> LENGTH: 9
<212> TYPE: PRT
<213> ORGANISM: Homo sapiens

<400> SEQUENCE: 2

Val Tyr Ser Ser Glu Glu Ala Glu Leu
 1               5

<210> SEQ ID NO 3
<211> LENGTH: 9
<212> TYPE: PRT
<213> ORGANISM: Homo sapiens

<400> SEQUENCE: 3

Gly Tyr Arg Ile Tyr Asp Val Val Leu
 1               5

<210> SEQ ID NO 4
<211> LENGTH: 9
<212> TYPE: PRT
<213> ORGANISM: Homo sapiens

<400> SEQUENCE: 4

Lys Phe Gly Asn Leu Ser Thr Tyr Leu
 1               5

<210> SEQ ID NO 5
<211> LENGTH: 9
```

```
<212> TYPE: PRT
<213> ORGANISM: Homo sapiens

<400> SEQUENCE: 5

Ser Tyr Met Ile Ser Tyr Ala Gly Met
 1               5

<210> SEQ ID NO 6
<211> LENGTH: 9
<212> TYPE: PRT
<213> ORGANISM: Homo sapiens

<400> SEQUENCE: 6

Glu Phe Pro Arg Asp Arg Leu Lys Leu
 1               5

<210> SEQ ID NO 7
<211> LENGTH: 9
<212> TYPE: PRT
<213> ORGANISM: Homo sapiens

<400> SEQUENCE: 7

Thr Phe Ser Glu Leu Val Glu His Leu
 1               5

<210> SEQ ID NO 8
<211> LENGTH: 9
<212> TYPE: PRT
<213> ORGANISM: Homo sapiens

<400> SEQUENCE: 8

Arg Phe Val Pro Asp Gly Asn Arg Ile
 1               5

<210> SEQ ID NO 9
<211> LENGTH: 9
<212> TYPE: PRT
<213> ORGANISM: Homo sapiens

<400> SEQUENCE: 9

Ala Phe Gly Ser Gly Met Glu Ser Leu
 1               5

<210> SEQ ID NO 10
<211> LENGTH: 9
<212> TYPE: PRT
<213> ORGANISM: Homo sapiens

<400> SEQUENCE: 10

Lys Asn Leu Asp Thr Leu Trp Lys Leu
 1               5

<210> SEQ ID NO 11
<211> LENGTH: 9
<212> TYPE: PRT
<213> ORGANISM: Homo sapiens

<400> SEQUENCE: 11

Lys Trp Glu Phe Pro Arg Asp Arg Leu
 1               5

<210> SEQ ID NO 12
<211> LENGTH: 9
<212> TYPE: PRT
<213> ORGANISM: Homo sapiens
```

```
<400> SEQUENCE: 12

Asp Phe Leu Thr Leu Glu His Leu Ile
 1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Asp Tyr Val Gly Ala Ile Pro Val Asp Leu
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Ser Tyr Gln Tyr Gly Thr Thr Gln Thr Leu
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Asp Tyr Val Arg Lys Gly Asp Ala Arg Leu
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Leu Tyr Thr Cys Ala Ala Ser Ser Gly Leu
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Val Tyr Ser Ser Glu Glu Ala Glu Leu Leu
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18
```

```
Leu Tyr Thr Cys Gln Ala Cys Ser Val Leu
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Thr Tyr Leu Arg Ser Lys Arg Asn Glu Phe
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Lys Tyr Leu Gly Tyr Pro Pro Pro Glu Ile
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Val Tyr Val Gln Asp Tyr Arg Ser Pro Phe
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Asn Tyr Thr Val Ile Leu Thr Asn Pro Ile
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Phe Phe Trp Leu Leu Leu Val Ile Ile Leu
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Ser Tyr Ala Gly Met Val Phe Cys Glu Ala
 1               5                  10
```

```
<210> SEQ ID NO 25
<211> LENGTH: 9
<212> TYPE: PRT
<213> ORGANISM: Homo sapiens

<400> SEQUENCE: 25

Thr Tyr Ala Cys Phe Val Ser Asn Leu
1               5

<210> SEQ ID NO 26
<211> LENGTH: 9
<212> TYPE: PRT
<213> ORGANISM: Homo sapiens

<400> SEQUENCE: 26

Val Leu Leu Trp Glu Ile Phe Ser Leu
1               5

<210> SEQ ID NO 27
<211> LENGTH: 9
<212> TYPE: PRT
<213> ORGANISM: Homo sapiens

<400> SEQUENCE: 27

Ser Leu Gln Asp Gln Gly Asp Tyr Val
1               5

<210> SEQ ID NO 28
<211> LENGTH: 9
<212> TYPE: PRT
<213> ORGANISM: Homo sapiens

<400> SEQUENCE: 28

Val Leu Leu Ala Val Ala Leu Trp Leu
1               5

<210> SEQ ID NO 29
<211> LENGTH: 9
<212> TYPE: PRT
<213> ORGANISM: Homo sapiens

<400> SEQUENCE: 29

Ala Met Phe Phe Trp Leu Leu Leu Val
1               5

<210> SEQ ID NO 30
<211> LENGTH: 9
<212> TYPE: PRT
<213> ORGANISM: Homo sapiens

<400> SEQUENCE: 30

Val Ile Ala Met Phe Phe Trp Leu Leu
1               5

<210> SEQ ID NO 31
<211> LENGTH: 9
<212> TYPE: PRT
<213> ORGANISM: Homo sapiens

<400> SEQUENCE: 31

Ile Leu Leu Ser Glu Lys Asn Val Val
1               5

<210> SEQ ID NO 32
```

```
<211> LENGTH: 9
<212> TYPE: PRT
<213> ORGANISM: Homo sapiens

<400> SEQUENCE: 32

Lys Asn Leu Asp Thr Leu Trp Lys Leu
  1               5

<210> SEQ ID NO 33
<211> LENGTH: 9
<212> TYPE: PRT
<213> ORGANISM: Homo sapiens

<400> SEQUENCE: 33

Ala Val Ile Ala Met Phe Phe Trp Leu
  1               5

<210> SEQ ID NO 34
<211> LENGTH: 9
<212> TYPE: PRT
<213> ORGANISM: Homo sapiens

<400> SEQUENCE: 34

Lys Leu Ile Glu Ile Gly Val Gln Thr
  1               5

<210> SEQ ID NO 35
<211> LENGTH: 9
<212> TYPE: PRT
<213> ORGANISM: Homo sapiens

<400> SEQUENCE: 35

Ile Met Trp Phe Lys Asp Asn Glu Thr
  1               5

<210> SEQ ID NO 36
<211> LENGTH: 9
<212> TYPE: PRT
<213> ORGANISM: Homo sapiens

<400> SEQUENCE: 36

Thr Leu Trp Lys Leu Asn Ala Thr Met
  1               5

<210> SEQ ID NO 37
<211> LENGTH: 9
<212> TYPE: PRT
<213> ORGANISM: Homo sapiens

<400> SEQUENCE: 37

Phe Gln Gly Gly Asn Lys Ile Glu Val
  1               5

<210> SEQ ID NO 38
<211> LENGTH: 9
<212> TYPE: PRT
<213> ORGANISM: Homo sapiens

<400> SEQUENCE: 38

Tyr Gln Tyr Gly Thr Thr Gln Thr Leu
  1               5

<210> SEQ ID NO 39
<211> LENGTH: 9
<212> TYPE: PRT
<213> ORGANISM: Homo sapiens
```

```
<400> SEQUENCE: 39

Ala Leu Ile Glu Gly Lys Asn Lys Thr
1               5

<210> SEQ ID NO 40
<211> LENGTH: 9
<212> TYPE: PRT
<213> ORGANISM: Homo sapiens

<400> SEQUENCE: 40

Tyr Met Ile Ser Tyr Ala Gly Met Val
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic peptide

<400> SEQUENCE: 41

Leu Leu Trp Glu Ile Phe Ser Leu Gly Ala
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

<400> SEQUENCE: 42

Val Leu Leu Ala Val Ala Leu Trp Leu Cys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Leu Met Thr Lys Lys Asn Ser Thr Phe Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide

<400> SEQUENCE: 44

Trp Leu Leu Leu Val Ile Ile Leu Arg Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide

<400> SEQUENCE: 45

Ala Leu Ile Glu Gly Lys Asn Lys Thr Val
```

<210> SEQ ID NO 46
<211> LENGTH: 10
<212> TYPE: PRT
<213> ORGANISM: Artificial Sequence
<220> FEATURE:
<223> OTHER INFORMATION: Synthetic peptide

<400> SEQUENCE: 46

Ile Gln Ser Asp Val Trp Ser Phe Gly Val
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide

<400> SEQUENCE: 47

Gly Leu Tyr Thr Cys Gln Ala Cys Ser Val
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Synthetic peptide

<400> SEQUENCE: 48

Leu Leu Leu Val Ile Ile Leu Arg Thr Val
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Synthetic peptide

<400> SEQUENCE: 49

Leu Leu Ala Val Ala Leu Trp Leu Cys Val
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Tyr Ile Thr Glu Asn Lys Asn Lys Thr Val
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide

<400> SEQUENCE: 51

Leu Leu Ser Glu Lys Asn Val Val Lys Ile
 1               5                  10

```
<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

Lys Val Leu Leu Ala Val Ala Leu Trp Leu
 1               5                  10

<210> SEQ ID NO 53
<211> LENGTH: 10
<212> TYPE: PRT
<213> ORGANISM: Homo sapiens

<400> SEQUENCE: 53

Asp Val Leu Tyr Gly Pro Asp Thr Pro Ile
 1               5                  10

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Val Leu Ala Met Phe Phe Trp Leu Leu
 1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

Ile Leu Lys Glu Pro Val His Gly Val
 1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Arg Tyr Leu Arg Asp Gln Gln Leu Leu
 1               5
```

KDR PEPTIDES AND VACCINES COMPRISING THE SAME

CROSS-REFERENCES TO RELATED APPLICATIONS

This application is a divisional of U.S. patent application Ser. No. 12/355,616, filed Jan. 16, 2009, now U.S. Pat. No. 7,695,720, which is a divisional of U.S. patent application Ser. No. 10/527,496, filed on Feb. 13, 2006, now U.S. Pat. No. 7,514,084, which is the National Stage Entry under 35 U.S.C. §371 of International Application No. PCT/JP03/11722, filed Sep. 12, 2003, which claims the benefit of JP Application No. 2003-167042, filed Jun. 11, 2003, JP Application No. 2003-62003, filed Mar. 7, 2003 and JP Application No. 2002-267285, filed Sep. 12, 2002. The entire disclosures of each of these applications is hereby incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

TECHNICAL FIELD

The present invention relates to novel peptides that are extremely useful as cancer vaccines, and pharmaceuticals that comprise these peptides, for treating and preventing tumors.

BACKGROUND ART

Tumor-rejection antigen genes have mainly been identified for malignant melanomas, and accordingly, cancer immunotherapies utilizing these genes are developed. Specifically, with recognition of the importance of CD8-positive T cells in anti-tumor immune responses, cancer vaccine therapy that induces tumor-specific CD8-positive T cells in vivo has received attention, and is being applied to various clinical applications. In addition, the mechanism by which peptides consisting of approximately ten amino acid residues activate T cells via the Class I pathway, by the assistance of various costimulatory molecules, to induce tumor-specific cytotoxic T cells (CTLs) was also elucidated. Furthermore, peptides restricted to individual HLA molecules are being actively identified.

However, complete control of tumors is currently impossible. This may be due to tumor cell heterogeneity, a reduction or disappearance of MHC-Class I expression in tumor cells, and the absence of target molecules in the tumor cells. Furthermore, the currently identified tumor antigen peptides exist in some types of tumors, but can not exist in all tumor types. Thus, to resolve these problems, the present inventors did not use tumor cells as target cells, but rather focused on the endothelial cells of tumor vessels. More specifically, endothelial cells have hardly any problems involving a decrease or disappearance of MHC-Class I expression, or heterogeneity. Thus, if CTLs that target tumor vessels can be induced, problems in conventional cancer vaccine therapy, such as the disappearance of Class I and absence of a target molecule, may be overcome, regardless of the type of tumor, and excellent therapeutic effects can be anticipated. Studies on tumor angiogenesis were started from a pioneering hypothesis proposed by Folkman et al. in the 1970's, and have been conducted from various angles. Many studies have been carried out on vascular endothelial growth factor (VEGF)—VEGF receptors (VEGFRs) to evaluate their significance in tumor angiogenesis. Angiogenesis inhibitors have been vigorously developed as target-oriented drugs, particularly in cancer therapy, and are already being clinically tested. However, therapies that use this concept for cancer vaccine treatments are not yet in use. One of the reasons may be immunotolerance to VEGFR, which is expressed in normal cells. However, in the 1990's, Plate, Millauer, and Risau et al. confirmed that VEGFRs were strongly expressed in the endothelial cells of tumoral tissues. In addition, the immune response to autoantigens such as CEA and HER/neu, which are also expressed in normal cells, is not necessarily one of immunotolerance. Thus, the present inventors reasoned that VEGFRs may be used as targets for cancer vaccine therapy.

Recently, it was reported that active immunization against VEGFRs can inhibit angiogenesis in tumors, and metastasis (The Journal of Experimental Medicine, 2002, 195:12, 1575-1584). However, this literature merely used soluble VEGFR proteins, and made no investigation of the amino acid sequences of effective peptides.

SUMMARY OF THE INVENTION

The present inventors focused on possible cancer vaccine therapies that target VEGFR2 (KDR/flk-1; referred to below as KDR), where VEGFR2 is strongly expressed in tumoral tissue endothelial cells, and is thought be involved in the proliferation of endothelial cells on the VEGF signal. Furthermore, the present inventors screened for peptides that can be effectively used as vaccines, examining their specificity, and completing this invention.

More specifically, the present invention provides [1] to [22] as follows.

[1] A nonapeptide selected from a group of peptides comprising the amino acid sequence of SEQ ID NO:2, 3, 5, 8, 11, or 12.

[2] A peptide with cytotoxic T cell inducibility, wherein one, two, or more amino acids are substituted or added to the amino acid sequence of SEQ ID NO:2, 3, 5, 8, 11, or 12.

[3] The peptide of [2], wherein the second amino acid from the N terminus is phenylalanine, tyrosine, methionine, or tryptophan.

[4] The peptide of [2] or [3], wherein the C-terminal amino acid is phenylalanine, leucine, isoleucine, tryptophan, or methionine.

[5] A nonapeptide or decapeptide selected from a group of peptides comprising the amino acid sequence of SEQ ID NO:29, 30, 33, 34, 40, or 46.

[6] A peptide with cytotoxic T cell inducibility, wherein one, two, or more amino acids are substituted or added to the amino acid sequence of SEQ ID NO:29, 30, 33, 34, 40, or 46.

[7] The peptide of [6], wherein the second amino acid from the N terminus is leucine or methionine.

[8] The peptide of [6] or [7], wherein the C-terminal amino acid is valine or leucine.

[9] A pharmaceutical for treating and/or preventing tumors, wherein the pharmaceutical comprises one or more peptides of any one of [1] to [8].

[10] A pharmaceutical for treating diabetic retinopathy, chronic rheumatoid arthritis, psoriasis, and atherosclerosis, wherein the pharmaceutical comprises one or more peptides of any one of [1] to [8].

[11] An exosome that presents on its surface a complex comprising a peptide of any one of [1] to [8], and an HLA antigen.

[12] The exosome of [11], wherein the HLA antigen is HLA-A24 or HLA-A02.

[13] The exosome of [12], wherein the HLA antigen is HLA-A2402 or HLA-0201.

[14] A method for inducing an antigen-presenting cell with high cytotoxic T cell inducibility by using a peptide of any one of [1] to [8].

[15] A method for inducing a cytotoxic T cell by using a peptide of any one of [1] to [8].

[16] A method for inducing an antigen-presenting cell with high cytotoxic T cell inducibility, wherein said method comprises the step of introducing a gene that comprises a polynucleotide encoding a peptide of any one of [1] to [8] into an antigen-presenting cell.

[17] An isolated cytotoxic T cell that is induced by using a peptide of any one of [1] to [8].

[18] An antigen-presenting cell that presents a complex of an HLA antigen and a peptide of any one of [1] to [8].

[19] The antigen-presenting cell of [18], which is induced by the method of [14] or [15].

[20] A vaccine for inhibiting angiogenesis at a diseased site, wherein the vaccine comprises a peptide of any one of [1] to [8] as an active ingredient.

[21] The vaccine of [20], which is used for administration to a subject whose HLA antigen is HLA-A24 or HLA-A02.

[22] The vaccine of [20] or [21], which is used to suppress the growth and/or metastasis of malignant tumors.

The present specification comprises the contents described in the specifications and/or drawings of Japanese Patent Application Nos. 2002-267285, 2003-062003, and 2003-167042, on which the priority rights of this invention are based.

Figure 1:
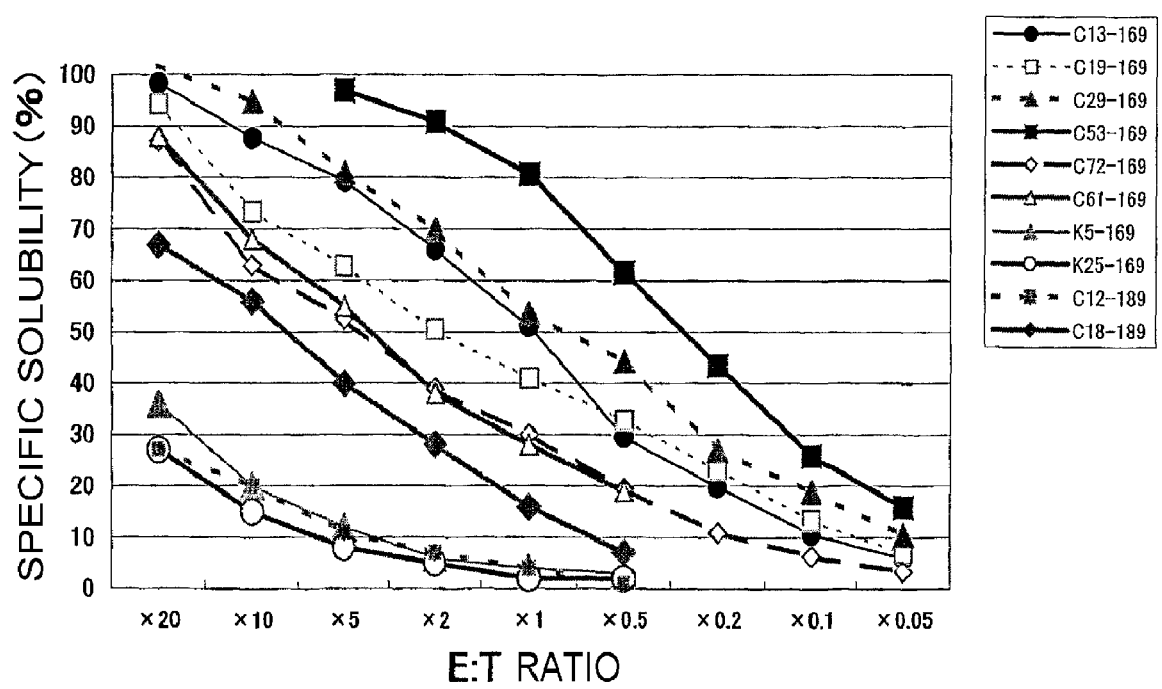
FIG. 1 shows the cytotoxicity of CTL clones against the target cells.

(A) The cytotoxic effect of colon cancer patient-derived CTL obtained by stimulation with SEQ ID NO:8 (in which the amino acid initiation position is KDR169);

(B) The cytotoxic effect of colon cancer patient-derived CTL obtained by stimulation with SEQ ID NO:5 (in which the amino acid initiation position is KDR189); and (C) The cytotoxic effect of colon cancer patient-derived CTL obtained by stimulation with SEQ ID NO:3 (in which the amino acid initiation position is KDR220).

DETAILED DESCRIPTION OF THE INVENTION

Mode for Carrying Out the Invention

The present inventors first considered that various proteins are presented in vivo on antigen presenting cells after being degraded to 9-mer peptides (nonapeptides), and examined the binding affinity of 9-mer or 10-mer partial peptides of KDR proteins to HLA antigens, which are human major histocompatibility antigens (MHC antigens). The lower case letters in the peptide sequences shown on the right of Table 1 indicate the fifth amino acids.

The amino acid sequence of human KDR protein is well known, disclosed by U.S. Pat. No. 5,861,301, for example, and can be easily obtained by one skilled in the art. The 9-mer and 10-mer peptides can be obtained by synthesizing peptides initiated from any position, based on the full-length amino acid sequence of the obtained KDR protein. Peptides can be synthesized according to conventional methods used in peptide chemistry. Commonly used synthesis methods are described, for example, in literatures such as Peptide Synthesis, Interscience, New York, 1966; The Proteins, vol. 2, Academic Press Inc., New York, 1976; Peptide Synthesis (Peputido Gousei), Maruzen Co., Ltd., 1975; Foundations and Experiments in Peptide Synthesis (Peputido Gousei no Kiso to Jikken), Maruzen Co., Ltd., 1985; and Development of Pharmaceuticals, New Series (Iyakuhin no Kaihatsu, Zoku), Volume 14, Peptide Synthesis (Peputido Gousei), Hirokawa Shoten, 1991, and in publications such as International Publication No. WO 99/67288. Binding with HLA antigens can be measured by isolating cells that comprise HLA antigens on their cell surface, such as dendritic cells, and using conventional methods to measure the binding of peptides to cells.

Alternatively, software programs now available on the Internet, such as those described in Parker, K. C., J. Immunol., 152, 1994, may be used to calculate the binding affinities between various peptides and HLA antigens in silico. Binding affinity with HLA antigens can be measured as described, for example, in Parker, K. C., J. Immunol., 152, 1994; and Nukaya, I., Int. J. Cancer, 80, 1999.

To obtain sufficient results, A-24 type and A-02 type antigens, said to be highly expressed among the Japanese, are preferably used as the HLA antigens. More preferably, subtypes such as A-2402 and A-0201 are used. However, clinically, by predetermining the HLA antigen type of a patient in need of treatment, a peptide can be appropriately selected to have a high level of binding affinity to that antigen, or level of cytotoxic T cell (CTL) inducibility upon antigen presentation. Furthermore, to obtain peptides with high levels of binding affinity and CTL inducibility, substitution or addition of one, two, or several amino acids may be performed based on the amino acid sequence of the naturally occurring KDR partial peptide. Herein, the term "several" means five or less, or preferably three or less. In addition to peptides in nature, the sequence regularity of the peptides displayed by binding to HLA antigens is already known (J. Immunol., 152:3913, 1994; Immunogenetics., 41:178, 1995; J. Immunol., 155: 4307, 1994). Thus, modifications based on this regularity can also be performed on the obtained peptides. For example, peptides in which the second amino acid from the N terminus is substituted with phenylalanine, tyrosine, methionine, or tryptophan, and in which the C terminal amino acid is substituted with phenylalanine, leucine, isoleucine, tryptophan, or methionine may also be preferably used as peptides with high HLA-24 binding affinity. On the other hand, peptides in which the second amino acid from the N terminus is substituted with leucine or methionine, and in which C terminal amino acid is substituted with valine or leucine may be preferably used as peptides with high HLA-0201 binding affinity. Furthermore, one to two amino acids may also be added to the N and/or C terminus of the peptides.

However, when a peptide sequence is identical to a portion of an amino acid sequence of an endogenous or exogenous protein with a different function, it may cause side effects such as autoimmune diseases or allergic symptoms against specific substances. Therefore, it is preferable to use available databases to carry out homology searches, to avoid situations in which a sequence matches the amino acid sequence of another protein. Furthermore, if homology searches reveal that no peptides comprising even a one- or two-amino acid difference exist, there is no risk of such problems caused by modifications of the above-mentioned amino acid sequences for increasing the binding affinity with HLA antigens and/or the CTL inducibility.

As described above, peptides with high binding affinity to the HLA antigens are expected to be highly effective as cancer vaccines. However, it is necessary to determine whether the candidate peptides, which are selected using high binding affinity as an indicator, actually have CTL inducibility or not. Confirmation of CTL inducibility is carried out by inducing antigen-presenting cells comprising human MHC antigens (such as B-lymphocytes, macrophages, and dendritic cells), more specifically dendritic cells derived from human peripheral blood mononuclear leukocytes; stimulating the cells with the peptides; mixing the cells with CD8-positive cells; and then measuring cytotoxicity against the target cells. As the reaction system, transgenic animals generated to express a human HLA antigen may be used (for example, those described in Hum. Immunol. 2000 August; 61(8):764-79 Related Articles, Books, Linkout Induction of CTL response by a minimal epitope vaccine in HLA A*0201/DR1 transgenic mice: dependence on HLA class II restricted T(H) response, BenMohamed, L., Krishnan, R., Longmate, J., Auge, C., Low, L., Primus, J., and Diamond, D. J.). For example, by radiolabeling the target cells with $^{51}$Cr or such, cytotoxicity can be calculated from the radioactivity released from the target cells. Alternatively, the activity can be examined by measuring the IFN-γ produced and released by CTL in the presence of antigen-presenting cells that have immobilized peptides, and visualizing the inhibition zone on the media using anti-IFN-γ monoclonal antibodies.

The results of examining the CTL inducibility of peptides as described above revealed that those with high binding affinity to HLA antigens do not necessarily have high inducibility. Furthermore, nonapeptides selected from peptides comprising the amino acid sequences of VYSSEEAEL (SEQ ID NO:2), GYRIYDVVL (SEQ ID NO:3), SYMISYAGM (SEQ ID NO:5), RFVPDGNRI (SEQ ID NO:8), KWEFPRDRL (SEQ ID NO:11), or DFLTLEHLI (SEQ ID NO:12), and nonapeptides and decapeptides selected from peptides comprising the amino acid sequence of AMFFWLLLV (SEQ ID NO:29), VIAMFFWLL (SEQ ID NO:30), AVIAMFFWL (SEQ ID NO:33), KLIEIGVQT (SEQ ID NO:34), YMISYAGMV (SEQ ID NO:40), or IQSDVWSFGV (SEQ ID NO:46), showed particularly high CTL inducibility.

The present invention further provides peptides with cytotoxic T cell inducibility, wherein one, two, or several amino acids are substituted with or added to the amino acid sequence of SEQ ID NO:2, 3, 5, 8, 11, or 12. One, two, or several amino acids can be substituted or added to the amino acid sequences of SEQ ID NOs:2, 3, 5, 8, 11, and 12, consisting of nine amino acids, as long as they have CTL inducibility and do not match the amino acid sequence of another protein. In particular, for example, the second amino acid from the N terminus is preferably substituted to phenylalanine, tyrosine, methionine, or tryptophan, or the C terminal amino acid is preferably substituted to phenylalanine, leucine, isoleucine, tryptophan, or methionine; or one or two amino acids are added to the N terminus and/or C terminus.

The present invention also provides peptides with cytotoxic T cell inducibility, wherein one, two, or several amino acids are substituted or added to the amino acid sequence of SEQ ID NO:29, 30, 33, 34, 40, or 46. One, two, or several amino acids can be substituted or added to the amino acid sequences of SEQ ID NOs:29, 30, 33, 34, 40, and 46, consisting of nine or ten amino acids, as long as they have CTL inducibility and do not match the amino acid sequence of another protein. In particular, for example, the second amino acid from the N terminus is preferably substituted to leucine or methionine, or the C terminal amino acid is preferably substituted to valine or leucine; or one or two amino acids are added to the N terminus and/or C terminus. An example of such a modified peptide is the peptide of SEQ ID NO:30, in which the second amino acid from the N terminus is substituted to leucine (SEQ ID NO:54), but this example is not limiting. CTL clones obtained on stimulation with these modified peptides can recognize the original peptides, and cause damage.

The peptides of this invention can be used alone or in combinations of two or more, as cancer vaccines capable of inducing CTL in vivo. By administering the peptides of this invention, the peptides are presented at a high density on the HLA antigens of antigen-presenting cells. CTLs that specifically react with the complexes formed between the displayed peptides and the HLA antigens are induced, increasing aggression against vascular endothelial cells in the tumor cells to be targeted. Alternatively, antigen-presenting cells on whose cell surface the peptides of this invention are immobilized can be obtained by deriving dendritic cells from a subject, and stimulating them with the peptides of this invention. The obtained antigen-presenting cells are re-administered to the subjects to induce CTL in the subjects. As a result, aggression towards the target cells can be increased.

More specifically, the present invention provides pharmaceuticals for treating tumors or preventing proliferation, metastasis, and such of tumors, where the pharmaceuticals comprise one or more peptides of this invention. Angiogenesis at pathologic sites is closely associated with not only tumors, but also with diseases such as diabetic retinopathy, chronic rheumatoid arthritis, psoriasis, and atherosclerosis, and the metastasis of solid tumors (Folkman, J., Nature Med., 1:27-31 (1995); Bicknell, R. and Harris, A. L., Curr. Opin. Oncol., 8:60-65 (1996)). Therefore, the peptides of this invention can be used to treat tumors, diseases such as diabetic retinopathy, chronic rheumatoid arthritis, psoriasis, atherosclerosis, and metastasis of solid tumors.

The peptides of this invention were confirmed to inhibit the formation of tortuous blood vessels, which are morphologically different from normal blood vessels, and which are formed in malignant tumoral tissues. The results of analyzing wound healing and fertility in vaccinated mice also confirmed that the peptides do not have an adverse effect on normal physiological angiogenesis. Furthermore, by using CTL clones that recognize the peptides of this invention, cytotoxicity against non-proliferative or proliferative endothelial cells was tested in vitro. These clones showed stronger activity towards proliferative endothelial cells than non-proliferative endothelial cells. More specifically, they can function very specifically for disorders involving proliferative endothelial cells, and particularly cancer.

In vivo and in vitro stimulation of dendritic cells by the peptides of this invention can be easily performed by exposing the cells to a high concentration of the peptides, which causes these peptides to replace the peptides originally immobilized on the cells. Therefore, the peptides used in this invention must have at least a certain level of binding affinity to HLA antigens.

The pharmaceuticals of this invention may be directly administered as the peptides of this invention themselves, or may be administered as pharmaceutical compositions that have been formulated by conventional formulation methods. In such cases, the pharmaceuticals of this invention can appropriately include, in addition to the peptides of this invention, carriers, excipients, and such that are ordinarily used for pharmaceuticals, without particular limitations. The pharmaceuticals of this invention can be used for treatment and prevention of various tumors, such as gastric cancer, duodenal cancer, colon cancer, lung cancer, breast cancer, prostate cancer, and brain tumors. The peptides of this invention do not target the tumor cells themselves, but target the endothelial cells of blood vessels that are newly formed in tumoral tissues. Therefore, a wide variety of tumors can be treatment targets, and the pharmaceuticals of this invention are not particularly limited in their use.

Pharmaceuticals for treating and/or preventing tumors, which comprise a peptide of this invention as an active ingredient, can be administered with adjuvants so that cellular immunity is induced effectively; can be administered with other active ingredients such as antitumor agents; and can be administered in granular forms. Those adjuvants described in the literature (Clin. Microbiol. Rev., 7:277-289, 1994) or such are applicable. Furthermore, the pharmaceuticals of this invention can be administered as liposome formulations, as granular formulations bound to beads of a few micrometers in diameter, and as formulations to which lipids are bound. Administration methods may be carried out, for example, orally, intradermally, or subcutaneously, or through intravenous injection, or such. Systemic administration or local administration to the vicinity of the target tumor may be applicable. Doses of the peptides of this invention can be adjusted appropriately, depending on the disease to be treated, age and weight of the patients, administration methods, and such. Ordinarily, 0.001 mg to 1,000 mg, preferably 0.01 mg to 100 mg, more preferably 0.1 mg to 10 mg, of the peptides of this invention are preferably administered once in a few days to a few months. One skilled in the art can appropriately select suitable doses.

Alternatively, the present invention provides intracellular vesicles which present complexes formed between the peptides of this invention and HLA antigens on their surface. These intracellular vesicles are called exosomes. Exosomes can be prepared, for example, according to the methods specifically described in Published Japanese Translation of International Publication Nos. Hei 11-510507 and 2000-512161. Exosomes can preferably be prepared using antigen-presenting cells obtained from subjects who are to be the target of therapy or prophylaxis. The exosomes of this invention can be inoculated as cancer vaccines, as for the peptides of this invention.

The type of HLA antigens to be used must match that of the subject in need of therapy and/or prophylaxis. For example, for Japanese people, HLA-A24 or HLA-A02, particularly HLA-A2402 or HLA-0201, is often appropriate.

The present invention also provides methods for inducing antigen-presenting cells using the peptides of this invention. The antigen-presenting cells can be induced by inducing dendritic cells from peripheral blood monocytes; and then contacting (stimulating) them with the peptides of this invention, in vitro or in vivo. Administering the peptides of this invention to subjects induces in the body of the subject antigen-presenting cells to which the peptides of this invention are immobilized. Alternatively, the peptides of this invention can be immobilized to the antigen-presenting cells to be administered to the subject as a vaccine.

The present invention also provides methods for inducing antigen-presenting cells with a high level of cytotoxic T cell inducibility, wherein said methods comprise the in vitro introduction to an antigen-presenting cell of a gene that comprises a polynucleotide encoding a peptide of this invention. The genes to be introduced may be in the form of DNA or RNA. The introduction methods may be various methods commonly used in the art, such as lipofection, electroporation, and calcium phosphate methods, without particular limitations. More specifically, the methods may be performed as described in, for example. Cancer Res., 56:5672, 1996; J. Immunol., 161:5607, 1998; J. Exp. Med., 184:465, 1996; or Published Japanese Translation of International Publication No. 2000-509281. By introducing the genes into antigen-presenting cells, the genes undergo transcription, translation, and such in the cells. The obtained proteins are then subjected to Class I or II MHC processing and a presentation pathway to present partial peptides.

Furthermore, the present invention provides methods for inducing CTLs using the peptides of this invention. By administering the peptides of this invention to a subject, CTLs are induced in the body of the subject, enhancing immunity against the angiogenic endothelial cells in the tumoral tissues. Alternatively, the methods may be used for ex vivo therapeutic methods, in which subject-derived, antigen-presenting cells, CD8-positive cells, or peripheral blood mononuclear leukocytes are contacted (stimulated) in vitro with the peptides of this invention to induce CTLs, and then the cells are returned to the subject.

In addition, the present invention provides cytotoxic T cells, that are induced using the peptides of this invention and then isolated. The cytotoxic T cells, which have been induced by stimulation with antigen-presenting cells that present the peptides of this invention, are preferably derived from subjects to be the target of therapy and/or prophylaxis. The cytotoxic T cells can be administered alone or, for the purpose of antitumor effect, in combination with other drugs, including the peptides, exosomes and so on of this invention. The obtained cytotoxic T cells act specifically against target cells presenting the peptides of this invention, or preferably, against target cells presenting the same peptides used for induction. The target cells may be cells that endogenously express KDR, or cells forced to express KDR. Furthermore, cells that present the peptides of this invention on their cell surface due to stimulation by these peptides can also be targeted.

The present invention also provides antigen-presenting cells that present complexes formed between HLA antigens and the peptides of this invention. The antigen-presenting cells that are obtained by contact with the peptides of this invention, or with nucleotides encoding the peptides of this invention, are preferably derived from subjects to be targeted for therapy and/or prophylaxis. The antigen-presenting cells can be administered as vaccines alone, or in combination with other drugs such as the peptides of this invention, exosomes, and cytotoxic T cells.

BEST MODE FOR CARRYING OUT THE INVENTION

Herein below, the present invention will be specifically described using Examples, but it is not to be construed as being limited thereto.

Example 1

Prediction of VEGFR-2 (KDR)-Derived Peptides—1 (HLA-A*2402)

Based on the entire amino acid sequence of KDR protein, twelve types of 9-mer peptides (SEQ ID NOs:1 to 12), and twelve types of 10-mer peptides (SEQ ID NOs:13 to 24) were predicted in order from that with the highest binding affinity to HLA-A*2402, using BioInformatics & Molecular Analysis Section (BIMAS) HLA Peptide Binding Prediction software (on the World Wide Web at bimas.dcrt.nih.gov/cgi-bin/molbio/ken_parker_comboform) (Table 1). Table 1 shows the binding affinity of each of the 9 mers and 10 mers in order from the highest value, together with the position of their N termini in the amino acid sequence of the KDR protein. In the table, CE652 (SEQ ID NO:25) refers to one of the epitopes of tumor antigen CEA (carcinoembryonic antigen) that has been reported by Nukaya, I. (Int. J. Cancer, 80, 1999). HIV peptides (ILKEPVHGV (SEQ ID NO:55) and RYLRDQQLL (SEQ ID NO:56)) were used as the negative control peptides.

The peptides were synthesized according to standard solid-phase synthesis methods using Cleaved PepSet (Mimotope, San Diego, Calif.), and purified by reverse phase HPLC. The purity (>95%) and the type of peptide were individually determined using HPLC and mass spectrometry.

TABLE 1

Binding of HLAA*2402 to KDR-derived peptides

| SEQ ID NO: | INITIATION POSITION | AA SEQUENCE (9 mers) | BINDING AFFINITY*[1] | SEQ ID NO: | INITIATION POSITION | AA SEQUENCE (10 mers) | BINDING AFFINITY*[1] |
|---|---|---|---|---|---|---|---|
| 1 | KDR583 | WYKLGPQPL | 240 | 13 | KDR950 | DYVGaIPVDL | 420 |
| 2 | KDR1318 | VYSSEEAEL | 220 | 14 | KDR434 | SYQYgTTQTL | 360 |
| 3 | KDR220 | GYRIYDVVL | 200 | 15 | KDR1058 | DYVRkGDARL | 300 |
| 4 | KDR920 | KFGNLSTYL | 48 | 16 | KDR304 | LYTCaASSGL | 200 |
| 5 | KDR189 | SYMISYAGM | 38 | 17 | KDR1318 | VYSSeEAELL | 200 |
| 6 | KDR828 | EFPRDRLKL | 33 | 18 | KDR734 | LYTCqACSVL | 200 |
| 7 | KDR1152 | TFSELVEHL | 29 | 19 | KDR926 | TYLRsKRNEF | 198 |
| 8 | KDR169 | RFVPDGNRI | 22 | 20 | KDR353 | KYLGyPPPEI | 165 |
| 9 | KDR331 | AFGSGMESL | 20 | 21 | KDR116 | VYVQdYRSPF | 150 |
| 10 | KDR604 | KNLDTLWKL | 16 | 22 | KDR395 | NYTViLTNPI | 72 |
| 11 | KDR826 | KWEFPRDRL | 12 | 23 | KDR777 | FFWL1LVIIL | 24 |
| 12 | KDR998 | DFLTLEHLI | 9 | 24 | KDR193 | SYAGmVFCEA | 9.2 |
| 25 | CE652*[2] | TYACFVSNL | 200 | | | | |

*[1]Parker KC:1994 J.Immunol 152
*[2]Nukava I:1999 Int J.Cancer 80

Example 2

Establishment of CTL Lines Using the Predicted Peptides

Epstein-Barr virus (EBV)-immortalized B cell lines, TISI (HLA-A24/24) and EHM (HLA-A3/3), were provided by Takara Shuzo Biotechnology Research Laboratory.

HLA serotyping was performed using 7 mL of peripheral blood collected from a healthy subject. Peripheral blood mononuclear lymphocytes (PBMCs) were isolated from HLA-A24-positive peripheral blood using Ficoll Paque (Pharmacia) specific gravity centrifugation.

The obtained PBMCs were left to stand for ten hours in a culture flask (Corning, 43072). After removing the suspended cells, the cells that adhered to the flask were cultured in AIM-V medium (Invitrogen) supplemented with 2% autoserum by adding 1,000 U/mL of human GM-CSF (provided by Kirin Brewery), and 1,000 U/mL of human IL-4 (Genzyme). Five days later, the cells were cultured for another 48 hours in 10 μg/mL of OK-432 (provided by Chugai Pharmaceutical Co., Ltd.), and were used as antigen-presenting cells for CTL induction. Dendritic cells (DCs) were confirmed to be DCs by reaction with FITC-labeled anti-ClassII, CD80, and CD86 antibodies, and with PE-labeled anti-ClassI, CD11c, CD40 and CD83 (Immunotech) antibodies; followed by analysis of surface antigens by FACS-Calibur (Beckton-Dickinson) using Cell Quest software.

Pre-induced DCs were pulsed for four hours at 20° C. with twelve kinds of 9-mer peptides (SEQ ID NOs:1 to 12) (20 μg/mL), that were predicted in Example 1 to have high binding affinity, in the presence of 3 μg/mL of β2-microglobulin. The resulting DCs were mixed with CD8-positive cells selected by magnetic beads (Dynabeads M-450 and Detachabeads) from PBMC, at a ratio of 1:20 or 1:2, and then cultured in a 48-well plate (Corning), in the presence of 10 ng/mL of human IL-7 (Genzyme). Three days later, the final concentration of 10 U/mL of IL-2 (Sigma) was added to the culture. And seven and 14 days later, the same DCs were stimulated to induce CTLs, and 20 days later, cytotoxicity was measured for each well using peptide-pulsed TISI cells as targets. Only the positive wells were cultured by a stimulation method with allo-PBMC, EBV-immortalized B cell lines (EHM), and 30 ng/mL of anti-CD3 antibody. CTLs were functionally analyzed 14 days later.

Cytotoxic activity was evaluated by a four-hour $^{51}$Cr release assay. A concentration of 20 μg/mL of the target cells were pulsed with peptides overnight. The target cells were labeled with 100 μCi of Na$_2$$^{51}$CrO$_4$ at 37° C. for one hour, and then washed three times with RPMI1640. The target cells (1×10$^4$/100 μL) and 100 μL of effector cells at various concentrations with a total volume of 200 μL were placed into a U-shaped 96-well microtiter plate (Corning), and cultured at 37° C. in a CO$_2$ incubator for four hours. After culturing, 100 μL of supernatant was collected from each well, and measured using a γ counter. Natural decay was the radioactivity of the target cells and the medium, and maximum decay was the radioactivity of the target cells and 1 M HCl. Cytotoxic activity (percentage of specific lysis) was calculated by the following formula:

$$\text{Cytotoxic activity}(\%\text{ Cytotoxicity}) = (\text{Experimental decay} - \text{natural decay})/(\text{maximum decay} - \text{natural decay}) \times 100$$

Six types of CTL lines were established as a result, as shown in Table 2. In particular, nonapeptides shown by SEQ ID NO:2 (amino acid initiation position KDR1318), SEQ ID NO:3 (KDR220), SEQ ID NO:5 (KDR189), SEQ ID NO:8 (KDR169), SEQ ID NO:11 (KDR826), and SEQ ID NO:12 (KDR998) were shown to be effective as epitope peptides.

TABLE 2

| SEQ ID NO: | INITIATION POSITION | AA SEQUENCE | BINDING AFFINITY[1] | CYTOTOXIC ACTIVITY ×20 Pep(+) | ×20 Pep(−) | ×2 Pep(+) | ×2 Pep(−) |
|---|---|---|---|---|---|---|---|
| 1 | KDR583 | WYKLGPQPL | 240 | 6% | 4% | 0% | 0% |
| 2 | KDR1318 | VYSSEEAEL | 220 | 39% | 21% | 8% | 3% |
| 3 | KDR220 | GYRIYDVVL | 200 | 67% | 2% | 20% | 0% |
| 4 | KDR920 | KFGNLSTYL | 48 | 3% | 4% | 0% | 2% |
| 5 | KDR189 | SYMISYAGM | 38 | 41% | 3% | 20% | 0% |
| 6 | KDR828 | EFPRDRLKL | 33 | 3% | 2% | 1% | 0% |
| 7 | KDR1152 | TFSELVEHL | 29 | 0% | 0% | 0% | 0% |
| 8 | KDR169 | RFVPDGNRI | 22 | 98% | 2% | 53% | 0% |
| 9 | KDR331 | AFGSGMESL | 20 | 6% | 6% | 0% | 0% |
| 10 | KDR604 | KNLDTLWKL | 16 | 3% | 2% | 1% | 1% |
| 11 | KDR826 | KWEFPRDRL | 12 | 23% | 0% | 11% | 0% |
| 12 | KDR998 | DFLTLEHLI | 9 | 13% | 4% | 8% | 0% |
| 26 | CE652[2] | TYACFVSNL | 200 | 29% | 16% | 7% | 1% |

[1] Parker.KC:1994.J.Immunol 152
[2] Nukaya I:1999 Int.J.Cancer 80

Example 3

Establishment of CTL Clones Derived from Predicted Peptides

The six types of CTL lines established in Example 2 were diluted to 0.3, 1, or 3 cells/well in a U-shaped 96-well plate. 7×10⁴ cells/well of allo-PBMC, 1×10⁴ cells/well of EHM, 30 ng/mL of anti-CD3 antibody, and 125 U/mL of IL-2 were added to each well, and AIM-V supplemented with 5% autoserum was added thereto, so that total concentration was 150 µL/well. Ten days later, 50 µL/well of IL-2-supplemented medium adjusted was added to a final IL-2 concentration of 125 U/mL. CTLs were functionally analyzed on the 14th day, and CTLs with activity were cultured on a large scale.

As a result, from each of the five types of nonapeptides shown by SEQ ID NO:8 (amino acid initiation position KDR169), SEQ ID NO:5 (KDR189), SEQ ID NO:3 (KDR220), SEQ ID NO:2 (KDR1318), and SEQ ID NO:11 (KDR826), eight types (C13-169, C19-169, C29-169, C53-169, C72-169, C61-169, K5-169, and K25-169), two types (C12-189 and C18-189), eleven types (KWC3, 23, 25, 26, 36, 42, 46, 58, 61, 70, and 77), one type (C7-1318), and one type (C65-826) of CTL clones were established, respectively (Table 3).

TABLE 3

| CLONE NAME | CYTOTOXIC ACTIVITY X20 Pep(+) | X20 Pep(−−) | X2 Pep(+) | X2 Pep(−−) |
|---|---|---|---|---|
| C13-169 | 98% | 2% | 66% | 2% |
| C19-169 | 94% | 2% | 50% | 0% |
| C29-169 | 100% | 1% | 70% | 0% |
| C53-169 | 100% | 2% | 91% | 2% |
| C72-169 | 87% | 1% | 39% | 0% |
| C61-169 | 88% | 0% | 38% | 0% |
| K5-169 | 36% | 0% | 6% | 0% |
| K25-169 | 27% | 0% | 5% | 0% |
| C12-189 | 27% | 18% | 7% | 3% |
| C18-189 | 67% | 18% | 28% | 7% |
| KWC3 | 54% | 2% | 11% | 1% |
| KWC23 | 95% | 1% | 49% | 1% |
| KWC25 | 93% | 1% | 70% | 1% |
| KWC26 | 87% | 1% | 34% | 0% |
| KWC36 | 62% | 2% | 11% | 2% |
| KWC42 | | | 67% | 0% |
| KWC46 | 94% | 1% | 51% | 0% |
| KWC58 | | | 76% | 0% |
| KWC61 | 70% | 2% | 19% | 1% |
| KWC70 | 92% | 3% | 64% | 2% |
| KWC77 | 99% | 3% | 70% | 2% |
| C65-826 | 38% | 6% | 8% | 3% |
| C7-1318 | 84% | 1% | 62% | 1% |

Example 4

Measurement of the Cytotoxicity of Established CTL Clones

The degrees of cytotoxicity of the ten types of CTL clones established in Example 3 were examined by varying their ratio with the target cells (E:T ratio).

As a result, C53-169 derived from the nonapeptide of SEQ ID NO:8 (amino acid initiation position KDR169) showed the strongest cytotoxicity.

Example 5

HLA-Tetramer Analysis of Established CTL Clones

An HLA-tetramer was synthesized from HLA-A*2402 and the peptide of SEQ ID NO:8 (amino acid initiation position KDR169). More specifically, plasmid vectors expressing the H chain (approximately 35 kDa) and L chain (approximately 11 kDa) were produced individually, and their recombinant protein was expressed using E. coli. The H-chain plasmid vector consists only of the extracellular domain, in which the carboxyl terminus was substituted with a biotinylation enzyme recognition sequence. The H chain and L chain form an HLA peptide complex by refolding with an antigenic peptide. The HLA peptide complexes were biotinylated by a biotinylation enzyme, excess biotin was removed by gel filtration chromatography and ion exchange chromatography, and the biotinylated HLA peptide complexes were isolated and purified. HLA-tetramer was synthesized by reacting the obtained biotinylated HLA peptide complex with streptavidin (SA) at a mole ratio of 4:1 to form a tetramer. When analyzing the samples, SA fluorescently labeled with phycoerythrin (PE) (SA-PE) was used to form the tetramer. CD8 molecule is known to bind to the 245th amino acid in the α3 domain, which is alanine, with the exception of portions of HLA-A, B, and C. Therefore, the present inventors mutagenized the alanine in the HLA-tetramers to valine, to produce a mutant HLA-tetramer capable of selectively detecting CTLs with high avidity towards HLA peptide complexes, independent of the binding between the CD8 molecule and the α3 domain.

Figure 2:
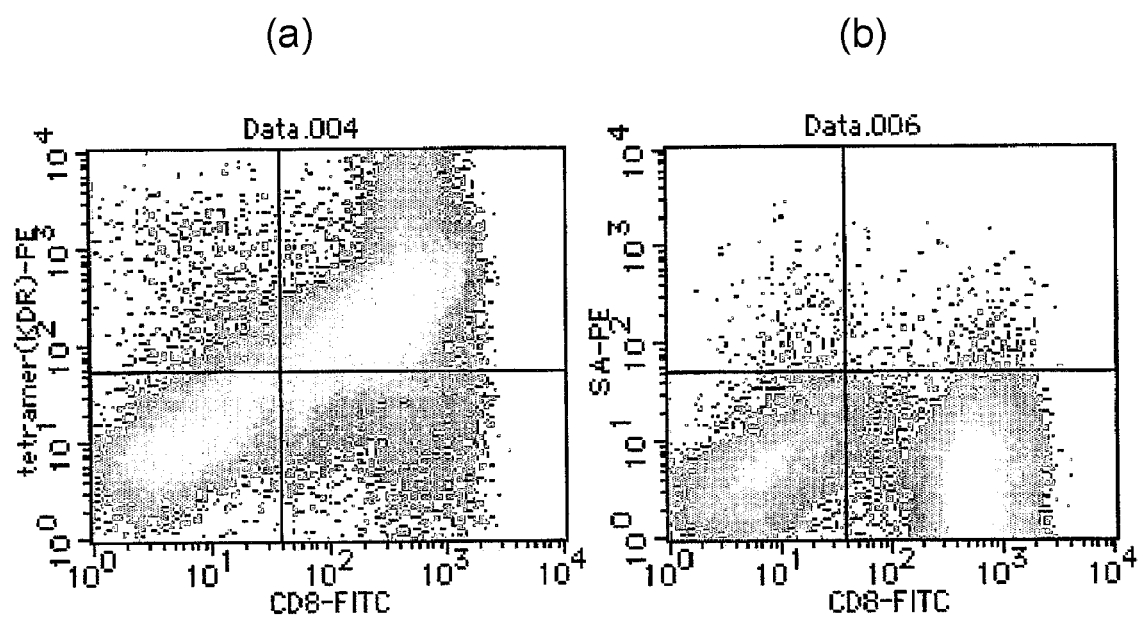
FIG. 2 shows the results of HLA-tetramer analyses of established CTL clones:
(a) CTL clones induced by the peptides of this invention, and feeder cells; and
(b) feeder cells (control).

Established CTL clones were detected by the synthesized HLA-A24 KDR169-tetramer mutant. As a result, as shown in FIG. 2, the established CTL clones were found to be strongly stained by the tetramer-positive and CD8-positive fractions, and to specifically recognize complexes formed between the peptides of this invention and HLA antigens. The signals in the tetramer-negative and CD8-negative fractions are due to feeder cells.

Example 6

Prediction of VEGFR-2 (KDR)-Derived Peptides—2 (HLA-A*0201)

In a similar manner to Example 1, 15 types of 9-mer peptides (SEQ ID NOs:26 to 40), and 12 types of 10-mer peptides (SEQ ID NOs:41 to 52) were predicted from the entire amino acid sequence of the KDR protein, in order from highest binding affinity with HLA-A*0201, using HLA Peptide Binding Prediction software (on the World Wide Web at bimas.dcrt.nih.gov/cgi-bin/molbio/ken_parker_comboform) (Table 4). Table 4 shows the binding affinity of each of the 9 mers and 10 mers in order from the highest value, together with the position of their N terminal in the amino acid sequence of the KDR protein. In the table, CEA588 (SEQ ID NO:53) refers to one of the epitopes of tumor antigen CEA (carcinoembryonic antigen) reported by Tanaka, H. et al. (poster presentation, AACR #3669, vol. 42, p 681-682, March 2001).

TABLE 4

Binding of HLA1A*0201 to KDR-derived peptides

| SEQ ID NO: | INITIATION POSITION | AA SEQUENCE (9 mers) | BINDING AFFINITY | SEQ ID NO: | INITIATION POSITION | AA SEQUENCE (10 mers) | BINDING AFFINITY |
|---|---|---|---|---|---|---|---|
| 26 | KDR1093 | VLLWEIFSL | 1792 | 41 | KDR1094 | LLWEIFSLGA | 1092 |
| 27 | KDR 633 | SLQDQGDYV | 769 | 42 | KDR 5 | VLLAvALWLC | 539 |
| 28 | KDR 5 | VLLAVALWL | 739 | 43 | KDR 313 | LMTKkNSTFV | 470 |
| 29 | KDR 775 | AMFFWLLLV | 427 | 44 | KDR 779 | WLLLvIILRT | 292 |
| 30 | KUR 773 | VIAMFFWLL | 270 | 45 | KDR 505 | ALIEgKNKTV | 285 |
| 31 | KDR1034 | ILLSEKNVV | 179 | 46 | KDR1084 | IQSDvWSFGV | 285 |
| 32 | KDR 604 | KNLDTLWKL | 128 | 47 | KDR 733 | GLYTcQACSV | 223 |
| 33 | KDR 772 | AVIAMFFWL | 113 | 48 | KDR 780 | LLLViILRTV | 201 |
| 34 | KDR1328 | KLIEIGVQT | 107 | 49 | KDR 6 | LLAVaLWLCV | 201 |
| 35 | KDR 698 | IMWFKDNET | 76 | 50 | KDR 137 | YITEnKNKTV | 180 |
| 36 | KDR 608 | TLWKLNATM | 41 | 51 | KDR1035 | LLSEkNVVKI | 167 |
| 37 | KDR 491 | FQGGNKIEV | 32 | 52 | KDR 4 | KVLLaVALWL | 133 |
| 38 | KDR 435 | YQYGTTQTL | 32 | | | | |
| 39 | KDR 505 | ALIEGKNKT | 31 | | | | |
| 40 | KDR 190 | YMISYAGMV | 30 | 53 | CEA 588*[1] | DVLYGPDTPI | 0.25 |

*[1]Tanaka H et al.:Poster presented at AACR 2001

Example 7

Determination of HLA-A*0201 Immobilizing Epitope Peptides

CTLs were induced by a vaccination method, using the 16 types of 9-mer and 10-mer peptides (SEQ ID NOs:26 to 41)

predicted in Example 6 on transgenic mice that express human HLA (A0201) (Hum. Immunol., 2000 August; 61(8): 764-79 Related Articles, Books, Linkout Induction of CTL response by a minimal epitope vaccine in HLA A*0201/DR1 transgenic mice: dependence on HLA class II restricted T(H) response, BenMohamed, L., Krishnan, R., Longmate, J., Auge, C., Low, L., Primus, J., and Diamond, D. J.).

Six- to eight-week old BALB/C(H-2$^d$) mice were obtained from CLEA Japan. A2/Kb transgenic mice (TGM) were provided by F. Jim Primus, Ph.D. at Vanderbilt-Ingram Cancer Center. T2 cells (TAP-deficient and HLA-A*0201-positive cells) were provided by Prof. H. Shiku at Mie University's Third Department of Internal Medicine.

Bone marrow was collected from mouse femur and tibia, and lymphocytes and granulocytes were removed using anti-CD4, CD8, Gr-1 antibodies (Beckton-Dickinson), anti-B220 antibody (Bioscience) and rabbit complement (PeL-Freez). The obtained cells were cultured in a 6-well plate. Suspended cells were collected the following day to culture in RPMI1640 (Invitrogen) medium supplemented with 10% FBS in another 6-well plate, to which 1,000 U/mL of mouse GM-CSF (provided by Kirin Brewery) and 1,000 U/mL of mouse IL-4 (PEPRO TECH) were added. Three days later, half of the above-mentioned medium was changed, and another two days later, the cells were cultured for 20 hours in 10 μg/mL of OK-432. The resulting suspended cells were used as DCs. DCs were reacted with FITC-labeled anti-ClassII and CD40 antibodies, and PE-labeled anti-ClassI, CD11c, CD80, and CD86 antibodies (all from Beckton-Dickinson), and confirmed to be DCs by analysis of the surface antigens by FACS-Calibur (Beckton-Dickinson) using Cell Quest software.

Next, 100 μg of each peptide, 140 μg of HbcAg120-140 helper peptide, and 100 μL of IFA were mixed (200 μL in total). The mixture was administered subcutaneously to the right abdomen on day 0, and to the left abdomen on day 11. The spleens of the vaccinated mice were collected on day 21, erythrocytes were hemolytically removed using red lysis buffer (Sigma), and a portion of those cells were used as responder cells for IFN-γ ELISPOT assay. The remaining cells were placed into a 24-well plate (Corning) at 6×10$^6$ cells/well with feeder cells at a ratio of 3:1, and stimulated again. Their cytotoxicity was measured five days later. Erythrocyte-free splenocytes, which were derived from syngeneic mice, were cultured for three days in the presence of 25 μg/mL of lipopolysaccharide (LPS) to use as feeder cells.

In this Example, the IFN-γ ELISPOT method was used to evaluate CTL inducibility according to SPOTs produced by IFN-γ producing cells. Flat-bottomed 96-well multiscreen plate MAHA S45 (Millipore) was treated at 4° C. overnight with anti-mouse IFN-γ monoclonal antibody (Pharmingen). On the following day, the plate washed with PBS containing 0.05% Tween 20, and then reacted with a blocking buffer at room temperature for two hours. Thereafter, peptide-pulsed T2 cells and unpulsed T2 cells were added to each well at 10$^5$ cells/100 pt. The splenocytes of vaccinated mice were further added to each well at a maximum of 4×10$^6$ cells/100 μL (200 μL in total), and cultured overnight at 37° C. The next day, each well was washed, and reacted for two hours with biotinylated rat anti-mouse IFN-γ antibodies (Pharmingen). After washing the plate thoroughly, Extravidin was added to each well and reacted at room temperature for two hours. After washing, alkaline phosphatase conjugate substrate (BIO-RAD) was added to the wells, which were left to stand at room temperature for five minutes. The blue spots resulting from IFN-γ production were measured using KS ELISPOT compact release (Carl Zeiss).

Specific blue spots were determined as:

Specific blue spot=($TISI$(+)SPOT−$TISI$(−)SPOT)

Those satisfying the following condition were considered effective:

$TISI$(+)SPOT/$TISI$(−)SPOT≧2

As a result, five types of epitope peptides, SEQ ID NO:29 (amino acid initiation position KDR775), SEQ ID NO:30 (KDR773), SEQ ID NO:33 (KDR772), SEQ ID NO:34 (KDR1328), and SEQ ID NO:40 (KDR190) were obtained by IFN-γ ELISPOT assay (Table 5).

TABLE 5

ELISPOT Analysis

| | | | | ELISPOT ANALYSIS × 40 (SFC) | | | |
| | | | | MOUSE1 | | MOUSE2 | |
| SEQ ID NO: | INITIATION POSITION | AA SEQUENCE | BINDING AFFINITY | pep(+) | pep(−) | pep(+) | pep(−) |
|---|---|---|---|---|---|---|---|
| 26 | KDR1093 | VLLWEIFSL | 1792 | 5 | 8 | 7 | 1 |
| 41 | KDR1094 | LLWEIFSLGA | 1092 | 0 | 0 | 0 | 0 |
| 27 | KDR 633 | SLQDQGDYV | 769 | 0 | 0 | 0 | 0 |
| 28 | KDR 5 | VLLAVALWL | 739 | 6 | 0 | 7 | 3 |
| 29 | KDR 775 | AMFFWLLLV | 427 | 95 | 32 | 322 | 17 |
| 30 | KDR 773 | VIAMFFWLL | 270 | 171 | 6 | 193 | 1 |
| 31 | KDR1034 | ILLSEKNVV | 179 | 0 | 0 | 0 | 0 |
| 32 | KDR 604 | KNLDTLWKL | 128 | 0 | 7 | 0 | 0 |
| 33 | KDR 772 | AVIAMFFWL | 113 | 88 | 19 | 143 | 31 |
| 34 | KDR1328 | KLIEIGVQT | 107 | 0 | 0 | 81 | 5 |
| 35 | KDR 698 | IMWFKDNET | 76 | 0 | 0 | 0 | 0 |

TABLE 5-continued

ELISPOT Analysis

| | | | | ELISPOT ANALYSIS × 40 (SFC) | | | |
|---|---|---|---|---|---|---|---|
| | | | | MOUSE1 | | MOUSE2 | |
| SEQ ID NO: | INITIATION POSITION | AA SEQUENCE | BINDING AFFINITY | pep(+) | pep(-) | pep(+) | pep(-) |
| 36 | KDR 608 | TLWKLNATM | 41 | 0 | 0 | 0 | 0 |
| 37 | KDR 491 | FQGGNKIEV | 32 | 0 | 0 | 0 | 0 |
| 38 | KDR 435 | YQYGTTQTL | 32 | 0 | 0 | 0 | 0 |
| 39 | KDR 505 | ALIEGKNKT | 31 | 0 | 0 | 0 | 0 |
| 40 | KDR 190 | YMISYAGMV | 30 | 122 | 6 | 33 | 11 |
| 53 | CEA 588*[1] | DVLYGPDTPI | 0.25 | 229 | 2 | 230 | 6 |

*[1]Tanaka H et al.:Poster presented at AACR 2001

Example 8

Confirmation of In Vivo Antitumor Effect—1

Bone marrow was collected from six- to eight-week old male BALB/c mice (CLEA Japan, Inc.) with that same anchor motif as human HLA-A2402. As in Example 7, GM-CSF (Kirin Brewery) (1,000 U/mL) and IL-4 (Genzyme) (1,000 U/mL) were added to the bone marrow and cultured to prepare dendritic cells. The dendritic cells were pulsed with the peptide of SEQ ID NO:5 (amino acid initiation position KDR189) and then administered (1×10$^6$ cells/mouse) twice to nine BALB/c mice at the right lower quadrant, with an interval of seven days. Seven days later, colon cancer cell line (5×10$^5$ cells), Colon 26 (Taiho Pharmaceutical), was inoculated to the right abdomens of the mice, and mice survival and tumor growth were examined.

Figure 3:
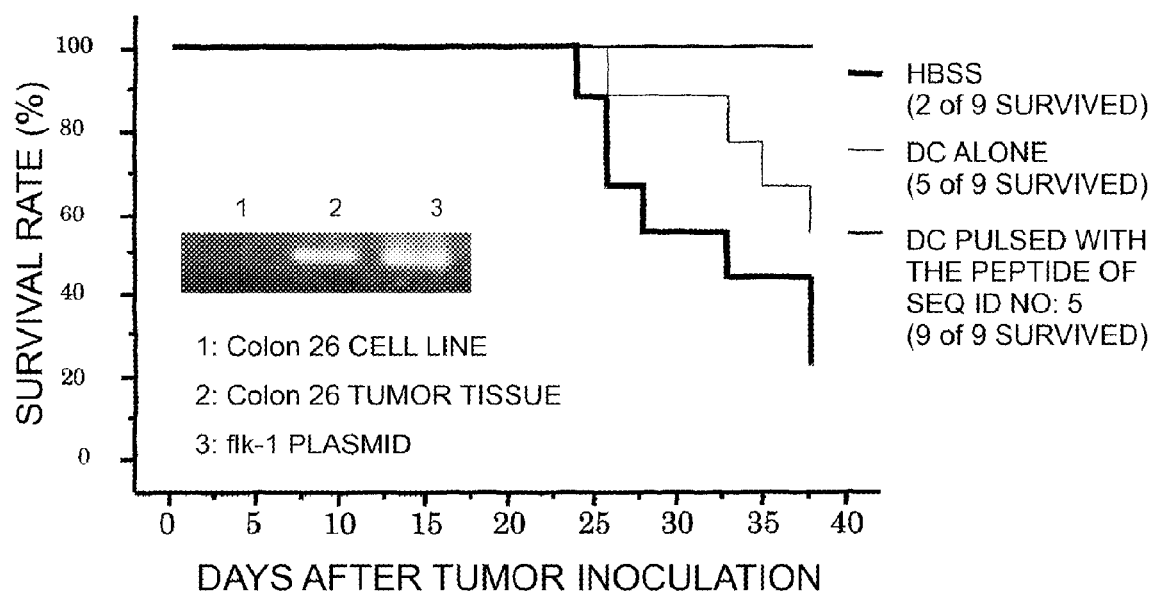
FIG. 3 shows the effect of vaccination using the peptides of this invention on the survival rate of Colon 26-inoculated BALB/c mice.

First, KDR expression was analyzed by RT-PCR, as indicated in FIG. 3, to confirm that KDR was not expressed in Colon 26 cells alone, but expressed in the tumoral tissues of mice inoculated with Colon 26. More specifically, tumor vessels were confirmed to appear in tumoral tissues, and to form the tumor.

FIG. 3 shows the survival curve of Colon 26-inoculated mice. 35 days after tumor inoculation, two out of nine mice survived when HBSS (Hank's Balanced Salt Solution) was administered alone (100 μL) as a control; five out of nine mice survived when inoculated with dendritic cells that were not pulsed with peptides; and all of the nine mice survived when inoculated with dendritic cells pulsed with the peptide of SEQ ID NO:5.

Figure 4:
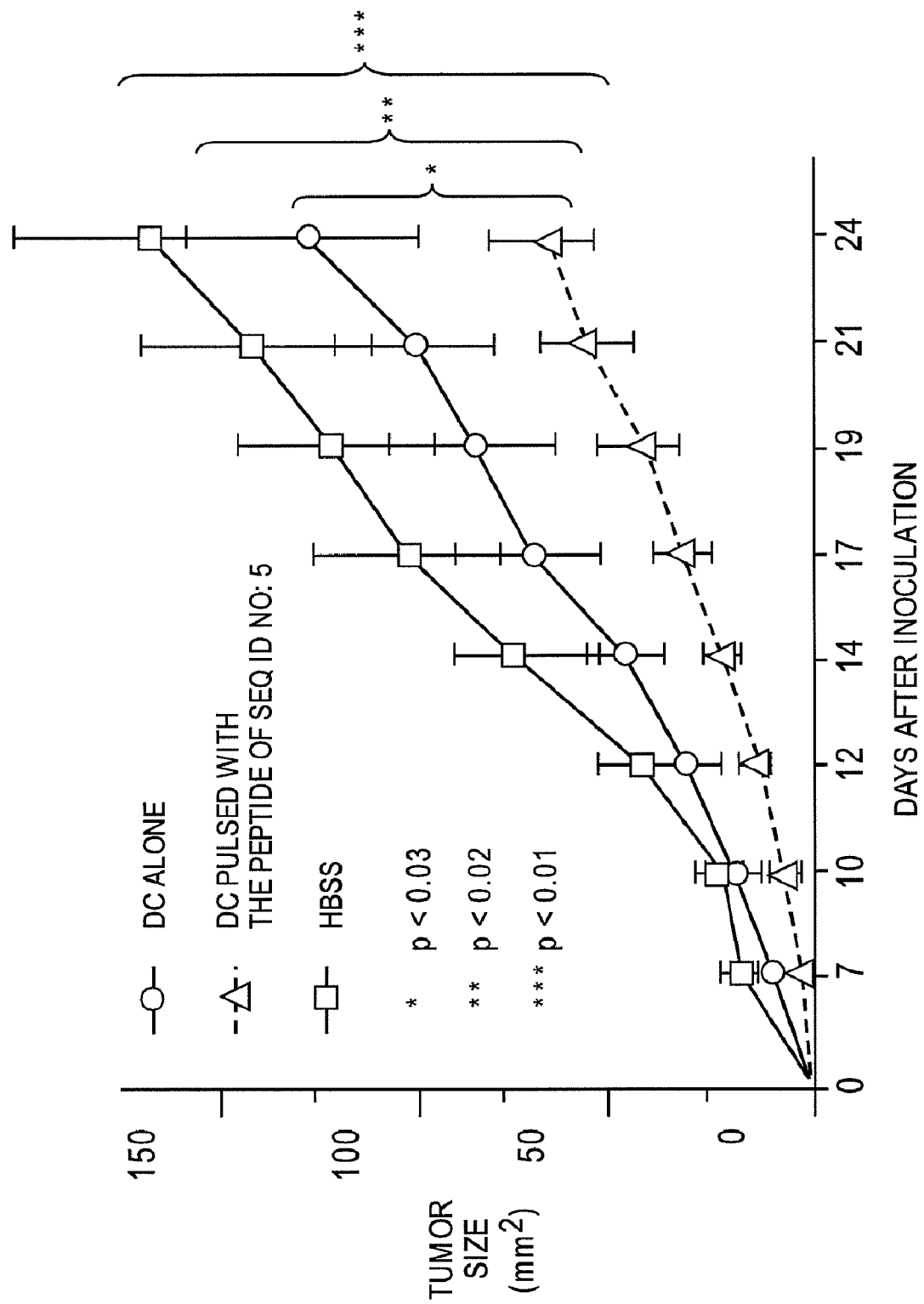
FIG. 4 shows the effect of vaccination using the peptides of this invention on the growth of Colon 26-derived tumors.

FIG. 4 shows the effect on the growth of Colon 26-derived tumors in mice. Compared to the control, suppressive effects on tumor growth were observed when inoculating dendritic cells, and remarkable suppression effects were observed when inoculating dendritic cells pulsed with the peptide of SEQ ID NO:5.

Example 9

Homology Searches for the Peptides of this Invention

Homology searches for the peptides of this invention (SEQ ID NO:2 (amino acid initiation position KDR1318), SEQ ID NO:3 (KDR220), SEQ ID NO:5 (KDR189), SEQ ID NO:8 (KDR169), SEQ ID NO:11 (KDR826), SEQ ID NO:30 (KDR773), and SEQ ID NO:40 (KDR190)) were carried out by using the BLAST program (on the World Wide Web at ncbi.nlm.nih.gov/blast/blast.cgi). No peptides with a sequence completely identical to any one of these peptides could be found (Table 6). The 9-mer peptide (KDR169) of SEQ ID NO:8 capable of inducing strong CTL activity in Example 4 had only one sequence containing two mismatches (77.8% homology), and two sequences containing three mismatches (66.7% homology). The peptide of SEQ ID NO:5 (KDR189), whose remarkable in vivo anti-tumor effect was observed in Example 8, had only one sequence containing three mismatches (66.7% homology).

TABLE 6

Homology analysis using the BLAST program (on the World Wide Web at ncbi.nlm.nih.gov/blast/blast.cgi)

| | KDR169 | KDR189 | KDR826 | KDR220 | KDR1318 | KDR773 | KDR190 |
|---|---|---|---|---|---|---|---|
| IDENTITY (9/9) | 0 | 0 | 0 | 0 | 0 | 0 | 0 |
| IDENTITY (8/9) | 0 | 0 | 3 | 0 | 0 | 0 | 0 |
| IDENTITY (7/9) | 1 | 0 | 2 | 0 | 2 | 2 | 0 |
| IDENTITY (6/9) | 2 | 1 | — | 0 | — | 2 | 0 |

Example 10

Confirmation of In Vivo Anti-Tumor Effect—2

Bone marrow was collected from six- to eight-week old male A2/Kb transgenic mice (TGM) expressing human HLA-A0201. As in Example 8, GM-CSF (Kirin Brewery) (1,000 U/mL) and IL-4 (Genzyme) (1,000 U/mL) were added to the bone marrow and then cultured to prepare dendritic cells. The dendritic cells were pulsed with the peptide of SEQ ID NO:30

(amino acid initiation position KDR773), and administered (1×10⁶ cells/mouse) twice to the left lower quadrant of twelve A2/Kb transgenic mice, with an interval of seven days. Seven days later, B16 melanoma cells (ATCC) were inoculated (1×10⁶ cells) to the right abdomen of the mice, and mice survival and tumor growth were examined.

Figure 5:
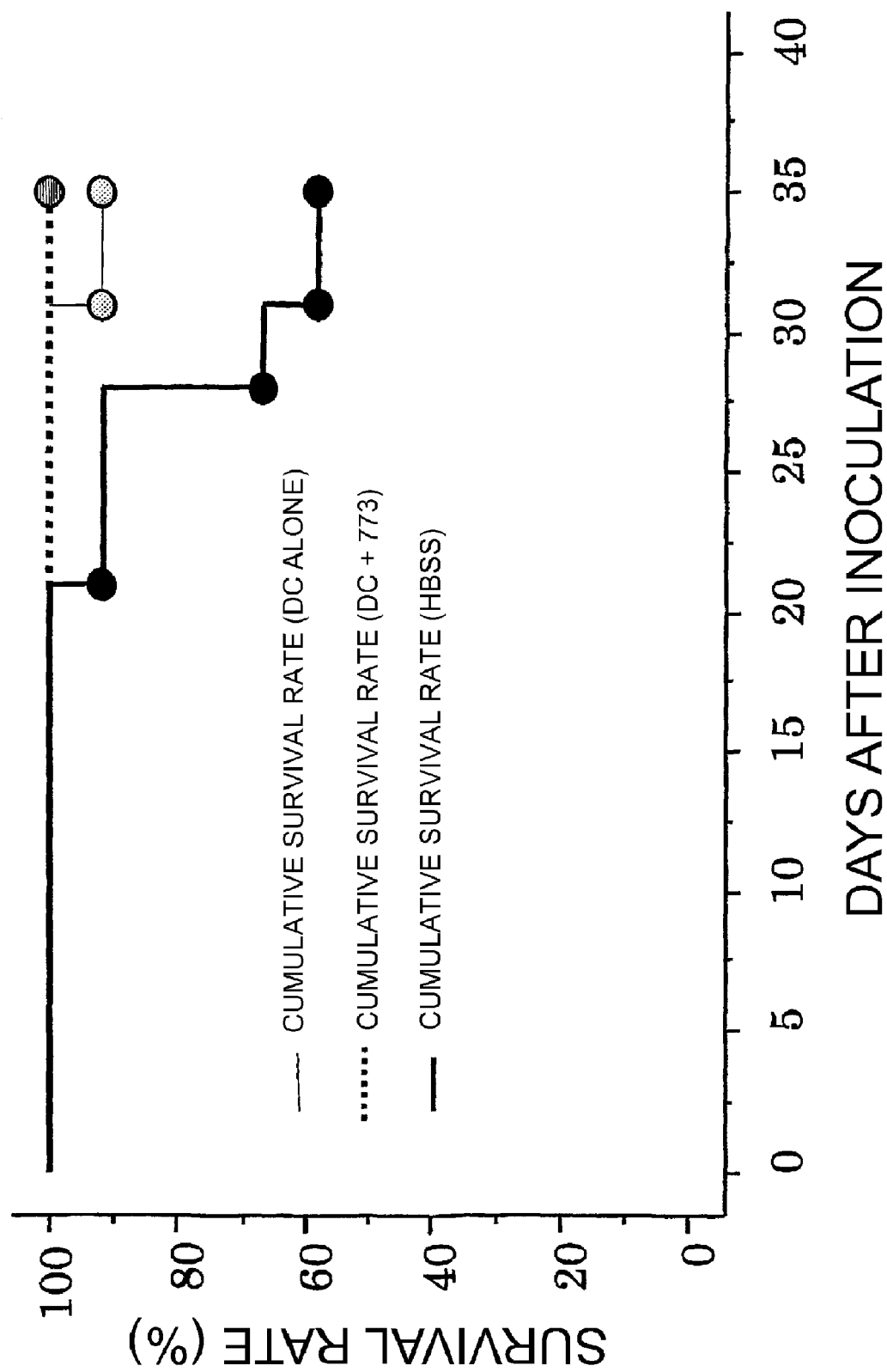
FIG. 5 shows the effect of vaccination using the peptides of this invention on the survival rate of B16-inoculated mice.

FIG. 5 shows the survival rate of B16-inoculated mice. 35 days after tumor inoculation, eight of twelve mice survived when HBSS was administered alone (100 μL) as a control; eleven of twelve mice survived when inoculated with dendritic cells that were not pulsed with peptides; and all twelve mice survived when inoculated with dendritic cells pulsed with the peptide of SEQ ID NO:30.

Figure 6:
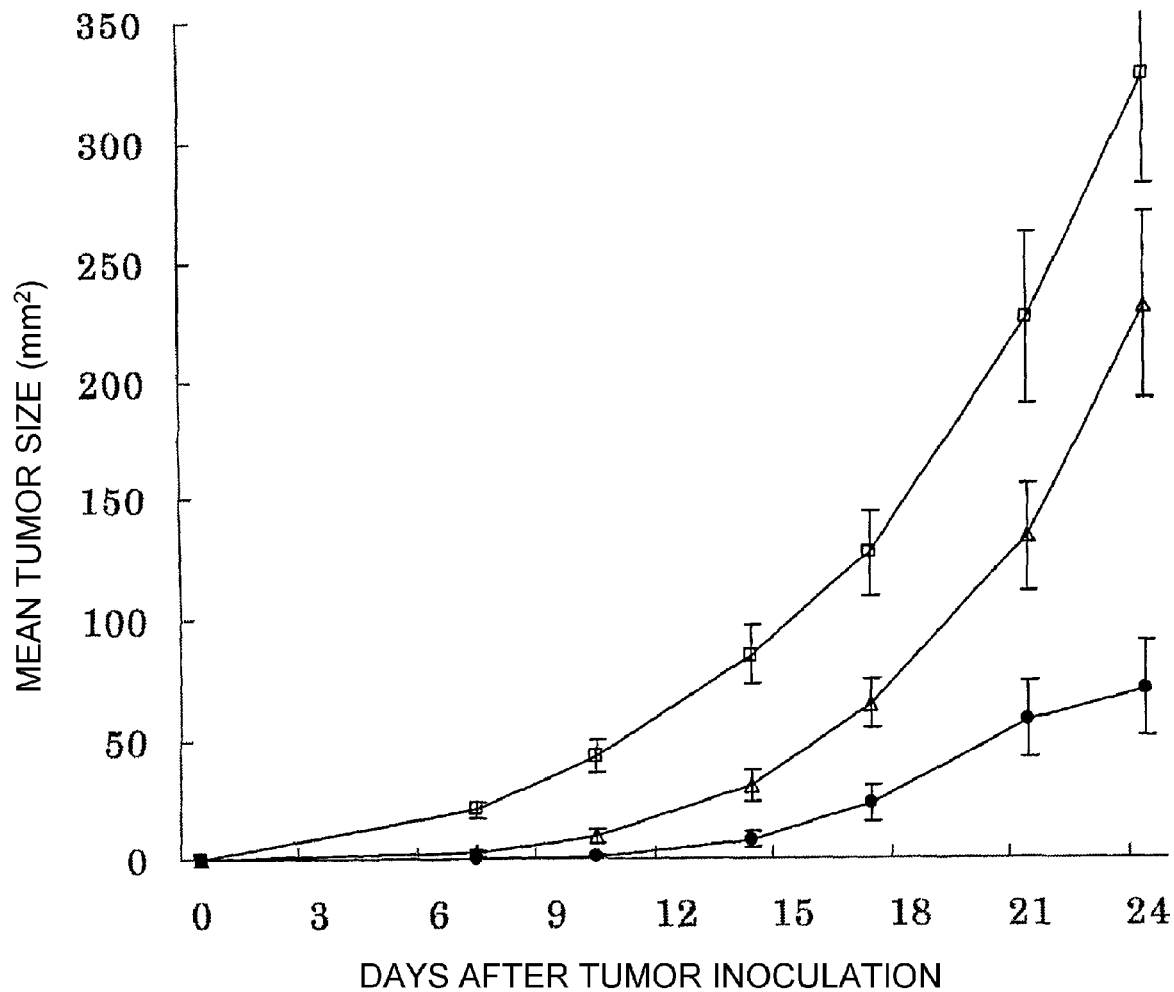
FIG. 6 shows the effect of vaccination using the peptides of this invention on the growth of B16 melanoma-derived tumors. Before challenge with a subcutaneous injection of B16 tumor cells, A2/Kb TGM were vaccinated twice, with a one-week interval, with DC pulsed with KDR773 (black circles), DC alone (white triangles), or HBSS (white squares). The figure shows mean tumor growth (P<0.01).

FIG. 6 shows the effect on the growth of B16 mice-derived tumors in mice. Compared to the control, suppressive effects were observed against tumor growth when inoculating with dendritic cells, and remarkable suppressive effects were observed on inoculating dendritic cells pulsed with the peptide of SEQ ID NO:30.

Example 11

Cytotoxic Activity Against Cells Forcibly Expressing KDR

Using adenoviruses, KDR (see, J. Biol. Chem., 1994 Oct. 28; 269(43):26988-95) was forcedly expressed in HLA-A24-positive human colon cancer HT29 strain (ATCC), according to the method described by Miyake, S. et al., Proc. Natl. Acad. Sci. USA., 93, 1320-1324 (1996). More specifically, based on the titer determined by plaque assay of human 293 cells, cells were infected at a specific multiplicity. HT29 cells were plated at a cell density of 105 cells in a 60-mm dish, and incubated for 24 hours. On the following day, the medium was removed and exchanged with 200 μL of viruses continuously diluted with fresh medium. The cells were incubated at 37° C. for one hour, and then growth medium was added to the cells, which were cultured for 48 hours to be used as target cells. HLA-A24-positive HT29 strain, forced by adenoviruses to express EGFP (see, Leukemia 1999 April; 13(4):605-13), was used as a control. HT29 strains forcedly expressing KDR and EGFP, respectively, can potentially present partial peptides of each protein on their respective cell surface.

Using CTL clone C29-169, induced from the peptide of SEQ ID NO:8 (amino acid initiation position KDR169), as described in Example 3, which binds to HLA-A24, the cytotoxic effect on HLA-A24-positive HT29 cells forced to express KDR was measured by chromium release assay. The results are shown in FIG. 7.

Cytotoxic activity was measured by $^{51}$Cr release assay for four hours. The target cells were cultured in a 6-well plate at a concentration of 1×10⁶ cells/well for 24 hours, infected with adenovirus to which KDR or EGFP has been inserted (Ad-KDR or Ad-EGFP) at MOI 50, and used after 48 hours. The target cells were labeled with 100 μCi of Na₂$^{51}$CrO₄ at 37° C. for one hour, and washed three times with RPMI1640. The target cells (1×10⁴ cells/100 μL) and 100 μL of effector cells at various concentrations were added (200 μL in total) to a U-shaped 96-well microtiter plate (Corning), and cultured in a CO₂ incubator at 37° C. for four hours. After culturing, 100 μL of supernatant was collected from each well and measured using a γ counter to calculate cytotoxicity, in the same manner as in Example 2.

Figure 7:
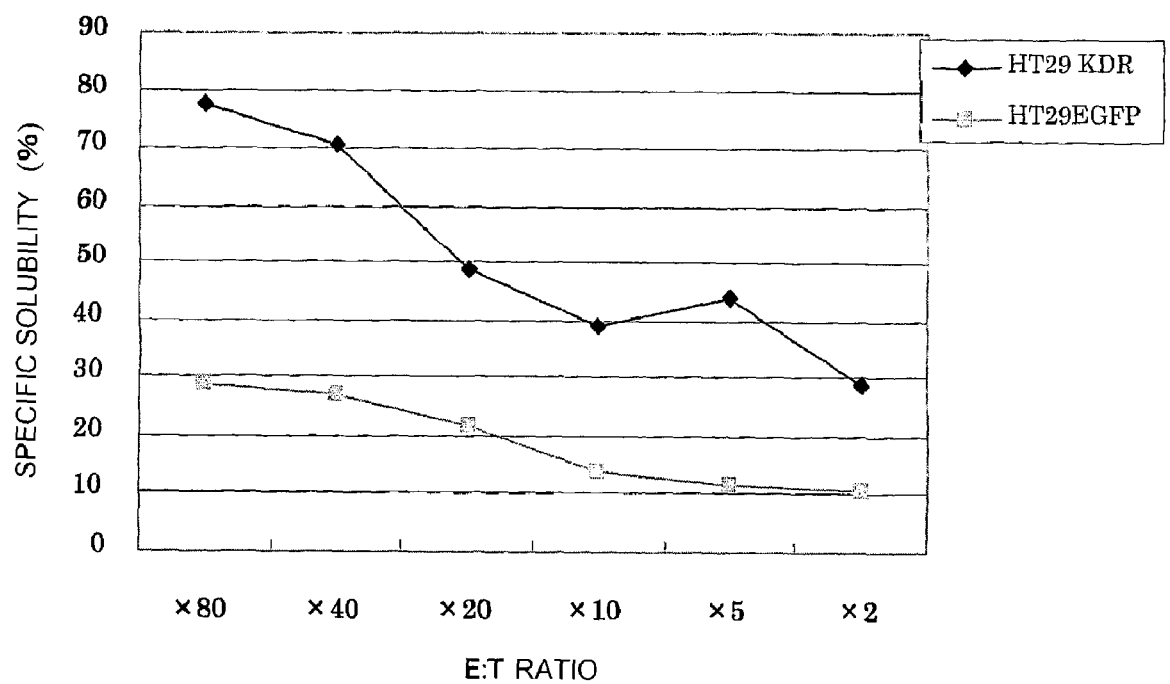
FIG. 7 shows the cytotoxic effect of CTL clone C29-169 on HLA-A24-positive cells presenting peptides of this invention.

As a result, as shown in FIG. 7, CTL clone C29-169 showed remarkably high cytotoxic effect towards HLA-A24-positive HT29 forcedly expressing KDR, compared to that towards cells forcedly expressing EGFP.

Example 12

Cytotoxic Activity Against Cells Endogenously Expressing KDR

The cytotoxic effect of the CTL clone C29-169 described in Example 3, against HUVEC KT5 strain, derived from HLA-A24-positive human umbilical cord vascular endothelial cells that endogenously express KDR, was examined using KDR-positive and HLA-A24-negative HUVEC strain, P8, as a control. These cells present partial peptides of KDR on their cell surface.

Cytotoxic activity was measured by a four hour $^{51}$Cr release assay. The target cells were labeled with 100 μCi of Na₂$^{51}$CrO₄ at 37° C. for one hour, then washed three times with RPMI1640. Target cells (1×10⁴ cells/100 μL) and 100 μL of effector cells at various concentrations were added (200 μL in total) to a U-shaped 96-well microtiter plate (Corning), and cultured in a CO₂ incubator at 37° C. for four hours. After culturing, 100 μL of supernatant was collected from each well and measured using a γ counter to calculate the cytotoxicity in the same manner as in Example 2.

Figure 8:
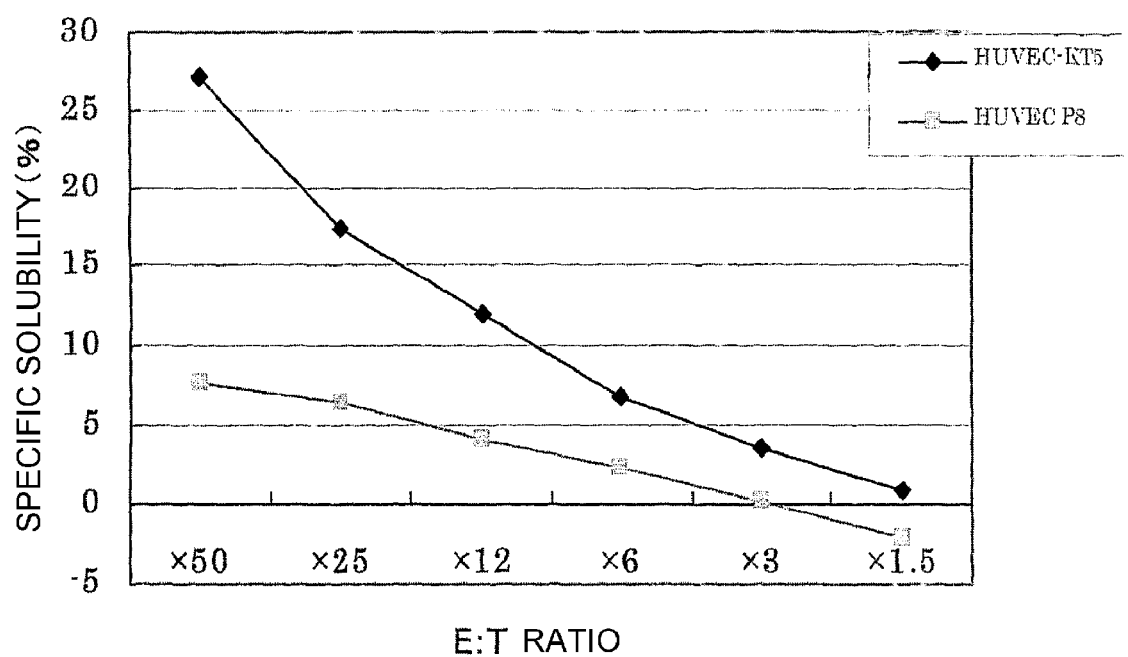
FIG. 8 shows the cytotoxic effect of CTL clone C29-169 on HLA-A24-positive cells presenting peptides of this invention.

As apparent from the results of FIG. 8, CTL clone C29-169 showed cytotoxic effect against HLA-A24-positive HUVEC endogenously expressing KDR, and showed weak cytotoxic effect against HLA-A24-negative HUVEC.

Example 13

Establishment of CTL Clones Using HLA-A0201-Binding Peptides

By using the peptide of SEQ ID NO:40 (amino acid initiation position KDR190), KDR773-2L peptide (SEQ ID NO:54) in which the second amino acid from the N terminal in the peptide of SEQ ID NO:30 (KDR773) has been converted to leucine, the peptide of SEQ ID NO:29 (KDR775), the peptide of SEQ ID NO:34 (KDR1328), and the peptide of SEQ ID NO:33 (KDR772), which bind to HLA-A0201 and which were determined to be effective according to the ELISPOT analysis in Example 7, two types (KWC14-190 and KWC65-190), four types (KWC44-773-2L, KWC76-773-2L, KWC129-773-2L, and KWC134-773-2L), two types (KWC81-775 and KWC85-775), twelve types (KWC16, KWC21, KWC22, KWC47, KWC51, KWC108, KWC117, KWC132, KWC151, KWC153, KWC156, and KWC159), and one type (KWC72-772) of CTL clones, respectively, were obtained as in Example 3. The respective cytotoxicities are shown in Table 7.

TABLE 7

| | CYTOTOXIC ACTIVITY | | | |
|---|---|---|---|---|
| | X20 | | X2 | |
| CLONE NAME | Pep(+) | Pep(--) | Pep(+) | Pep(--) |
| KWC14-190 | 43% | 0% | 9% | 0% |
| KWC65-190 | 83% | 0% | 27% | 0% |
| KWC44-773-2L | 87% | 0% | 64% | 0% |
| KWC76-773-2L | 83% | 2% | 68% | 1% |
| KWC129-773-2L | 89% | 0% | 82% | 1% |
| KWC134-773-2L | 89% | 2% | 54% | 2% |
| KWC81-775 | 86% | 0% | 64% | 0% |
| KWC85-775 | 90% | 0% | 63% | 0% |

TABLE 7-continued

| | CYTOTOXIC ACTIVITY | | | |
|---|---|---|---|---|
| | X20 | | X2 | |
| CLONE NAME | Pep(+) | Pep(--) | Pep(+) | Pep(--) |
| KWC16 | 95% | 0% | 85% | 0% |
| KWC21 | 100% | 0% | 91% | 0% |
| KWC22 | 93% | 0% | 77% | 0% |
| KWC47 | 109% | 2% | 87% | 1% |
| KWC51 | 101% | 0% | 93% | 1% |
| KWC108 | 71% | 2% | 23% | 2% |
| KWC117 | 83% | 0% | 42% | 0% |
| KWC132 | 102% | 0% | 55% | 0% |
| KWC151 | 102% | 0% | 101% | 0% |
| KWC153 | 47% | 0% | 18% | 0% |
| KWC156 | 64% | 0% | 23% | 0% |
| KWC159 | 93% | 0% | 86% | 0% |
| KWC72-772 | 101% | 0% | 67% | 0% |

As apparent from the results in Table 7, the peptides of SEQ ID NOs:29, 33, 34, and 40, as well as the peptide of SEQ ID NO:54, in which the second amino acid from the N terminus in the peptide of SEQ ID NO:30 is leucine, can all induce CTLs having remarkable cytotoxicity, and were thus shown to be effective as epitope peptides.

Example 14

The peptide of SEQ ID NO:29 (amino acid initiation position KDR775) was added to HLA-A0201-positive T2 strain to produce a target cell. By using the cell, the cytotoxic effect of the CTL clone (KDR C85-775 (KWC85-775)) obtained from the peptide of SEQ ID NO:29 in Example 13 was examined by chromium release assay.

Figure 9:
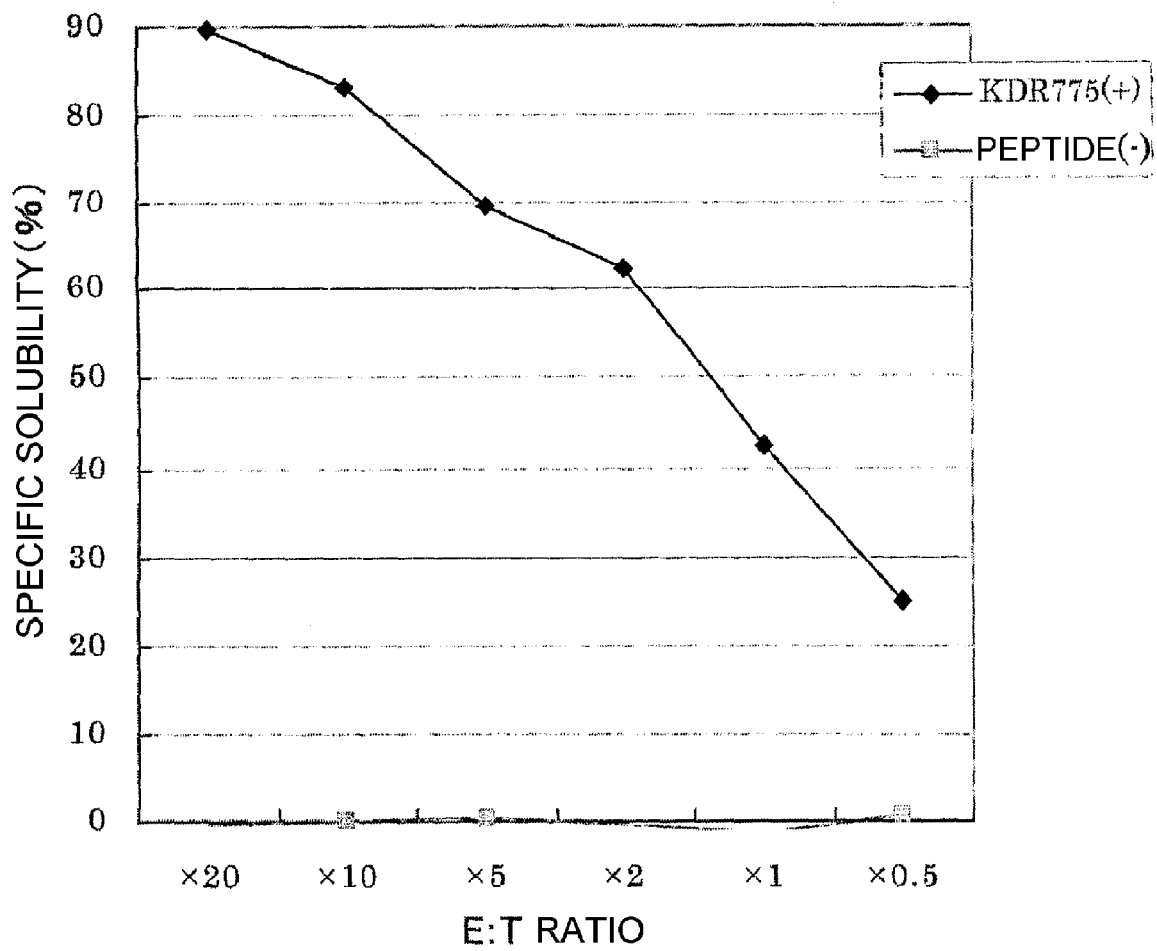
FIG. 9 shows the cytotoxic effect of CTL clone KDR C85-775 (KWC85-775) on HLA-A0201-positive cells presenting peptides of this invention.

In the results, shown in FIG. 9, CTL clone C85-775 (KWC85-775) clearly showed a cytotoxic effect against HLA-A0201-positive cells presenting the peptide of SEQ ID NO:29. In contrast, absolutely no cytotoxic effect was observed against control cells not presenting the peptide of SEQ ID NO:29.

Example 15

The cytotoxic effect of the CTL clone (KDR C85-775 (KWC85-775)) against hepatocellular carcinoma cell line HLA-A0201-positive HePG2, forced by adenoviruses to express KDR, was examined by chromium release assay. HLA-A0201-positive HePG2 forced to express EGFP was used as control.

Figure 10:
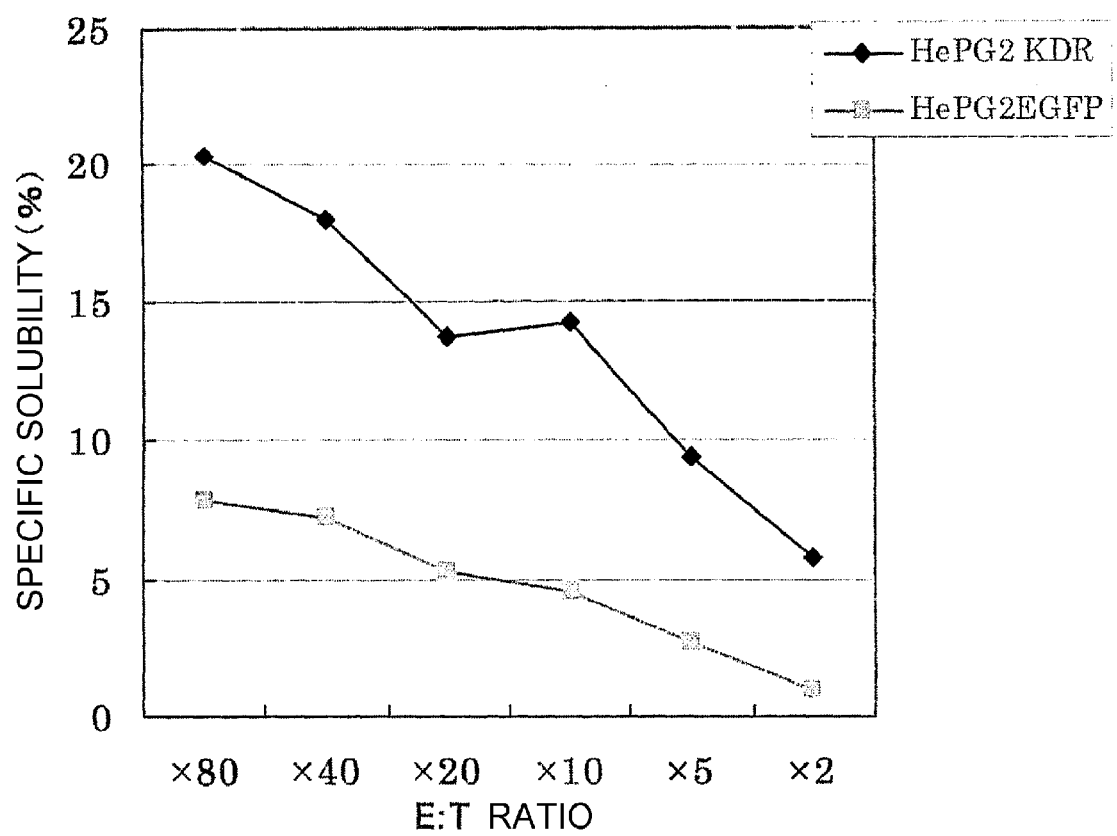
FIG. 10 shows the cytotoxic effect of CTL clone KDR C85-775 (KWC85-775) on HLA-A0201-positive cells presenting KDR peptides.

In the results, shown in FIG. 10, CTL clone KDR C85-775 (KWC85-775) showed remarkably high cytotoxic effect against HLA-A0201-positive cells presenting KDR peptides on the surface, compared to activity against cells presenting the EGFP peptide.

Example 16

The peptide of SEQ ID NO:34 (amino acid initiation position KDR1328) was added to HLA-A0201-positive T2 strain to produce target cells. Using these cells, the cytotoxic effect of the CTL clone (KDR C51-1328 (KWC51)) obtained from the peptide of SEQ ID NO:34 in Example 13 was examined by chromium release assay.

Figure 11:
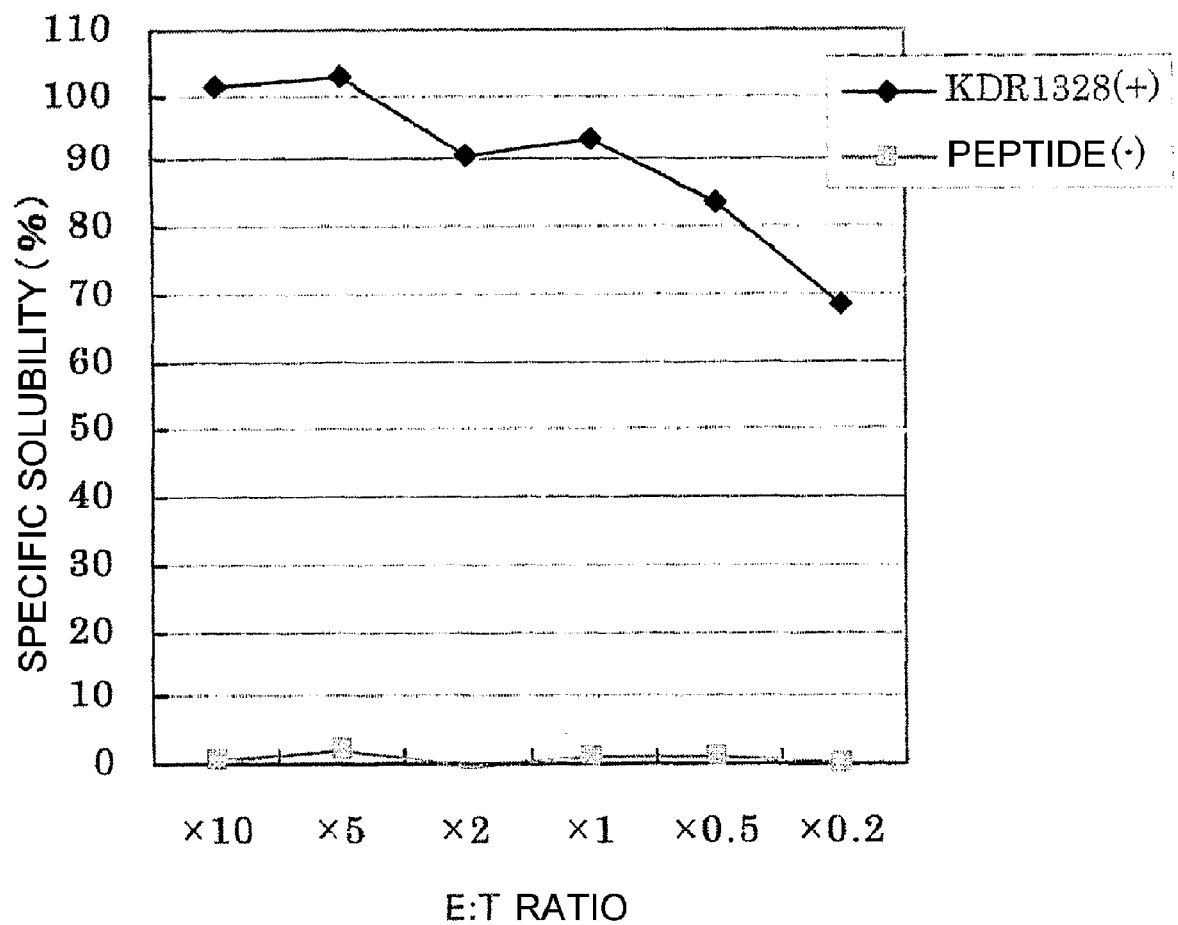
FIG. 11 shows the cytotoxic effect of CTL clone KDR C51-1328 (KWC51) on HLA-A0201-positive cells presenting peptides of this invention.

In the results, shown in FIG. 11, CTL clone KDR C51-1328 (KWC51) clearly showed a cytotoxic effect against HLA-A0201-positive cells presenting the peptide of SEQ ID NO:34. In contrast, absolutely no cytotoxic effect was observed against control cells not presenting the peptide of SEQ ID NO:34.

Example 17

The cytotoxic effect of the CTL clone (KDR C51-1328 (KWC51)) against hepatocellular carcinoma cell line HLA-A0201-positive HePG2, forced by adenoviruses to express KDR, was examined by chromium release assay. HLA-A0201-positive HePG2 forced to expressing EGFP was used as control.

Figure 12:
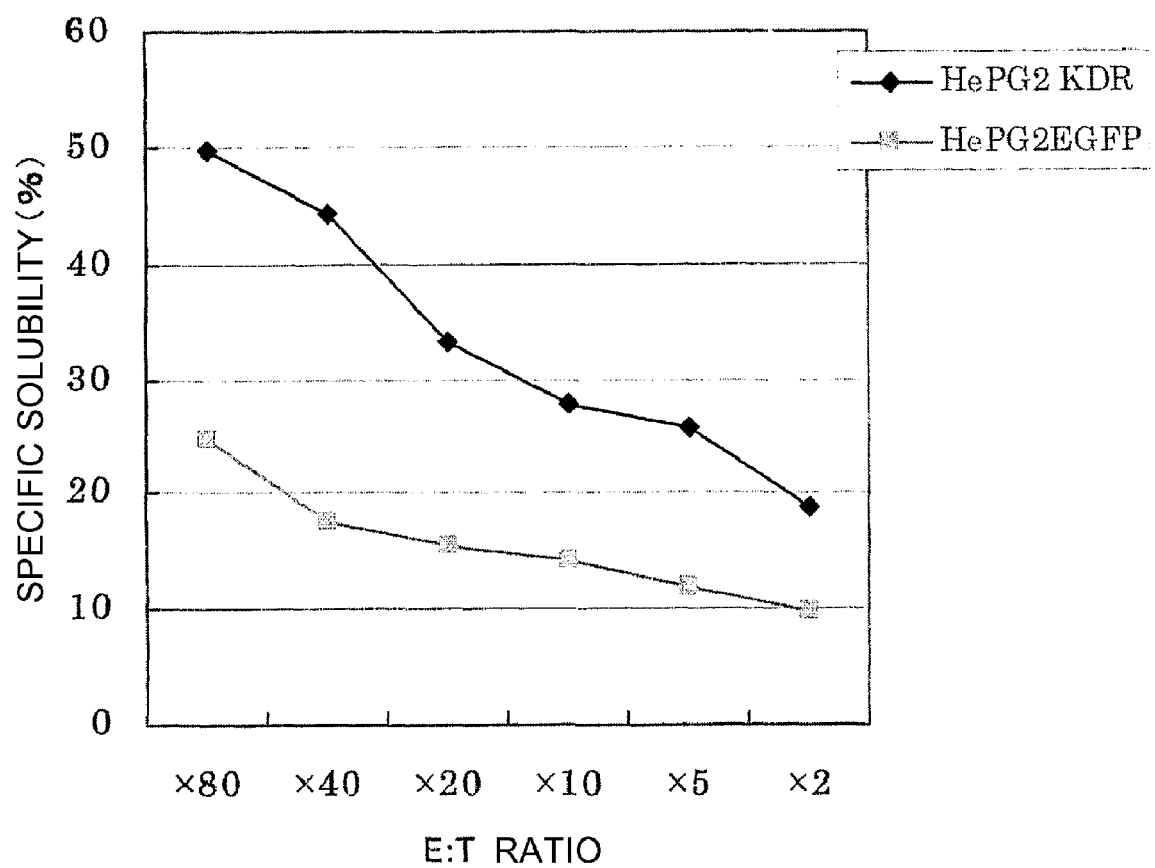
FIG. 12 shows the cytotoxic effect of CTL clone KDR C51-1328 (KWC51) on HLA-A0201-positive cells presenting KDR peptides.

In the results, shown in FIG. 12, CTL clone KDR C51-1328 (KWC51) showed remarkably high cytotoxicity against HLA-A0201-positive cells presenting KDR peptides on the surface, compared to activity against cells presenting the EGFP peptide.

Example 18

Figure 13:
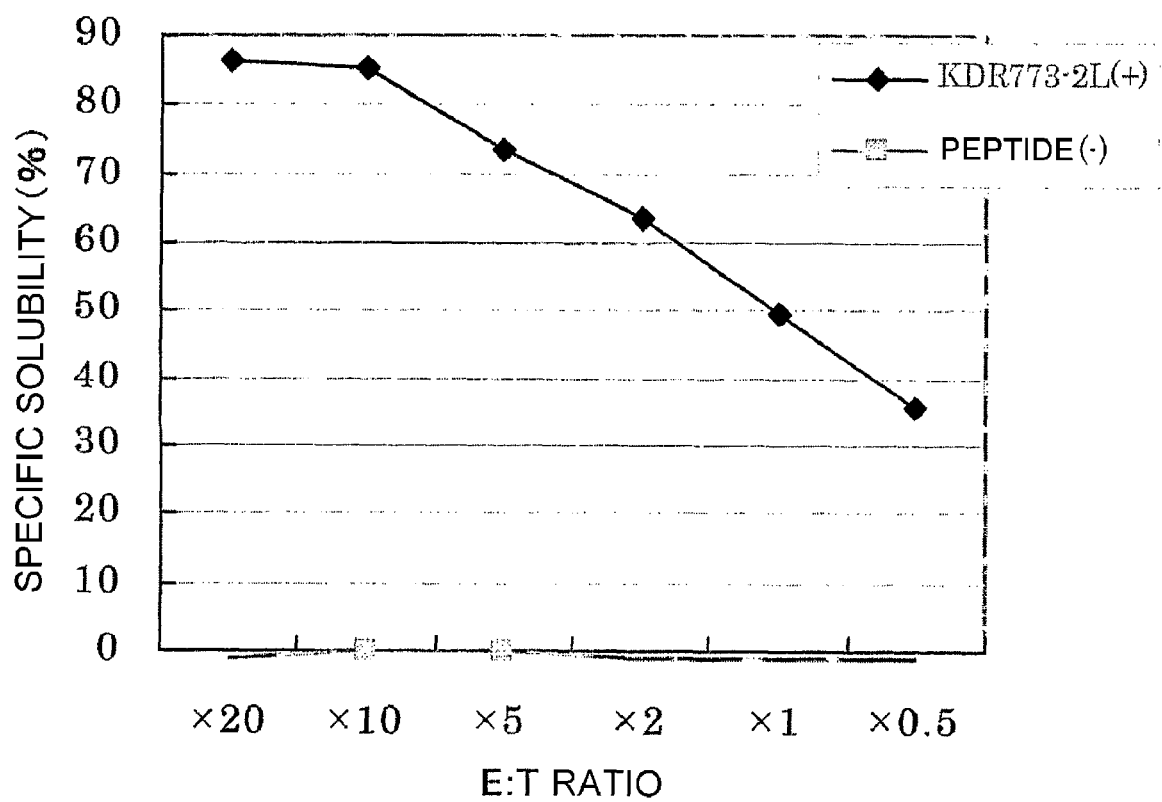
FIG. 13 shows the cytotoxic effect of CTL clone KDR C44-773-2L (KWC44-773-2L) on HLA-A0201-positive cells presenting peptides of this invention.

The peptide of SEQ ID NO:54 (KDR773-2L), in which the second peptide of SEQ ID NO:30 is converted to leucine, was added to HLA-A0201-positive T2 strain to produce target cells. Using these cells, the cytotoxic effect of the CTL clone (KDR C44-773-2L (KWC44-773-2L)) obtained from the peptide of SEQ ID NO:54 in Example 13 was examined by chromium release assay. FIG. 13 shows the results.

In the results, shown in FIG. 13, CTL clone KDR C44-773-2L (KWC44-773-2L) clearly showed a cytotoxic effect against HLA-A0201-positive cells presenting KDR773-2L. In contrast, absolutely no cytotoxic effect was observed against control cells not presenting KDR773-2L.

Example 19

The cytotoxic effect of the CTL clone (KDR C44-773-2L (KWC44-773-2L) obtained from the peptide of SEQ ID NO:54 (KDR773-2L), in which the second peptide of SEQ ID NO:30 has been converted to leucine, was examined by chromium release assay using HLA-A0201-positive T2 strain pulsed with the unmodified peptide of SEQ ID NO:30 (amino acid initiation position KDR773) as the target cell.

Figure 14:
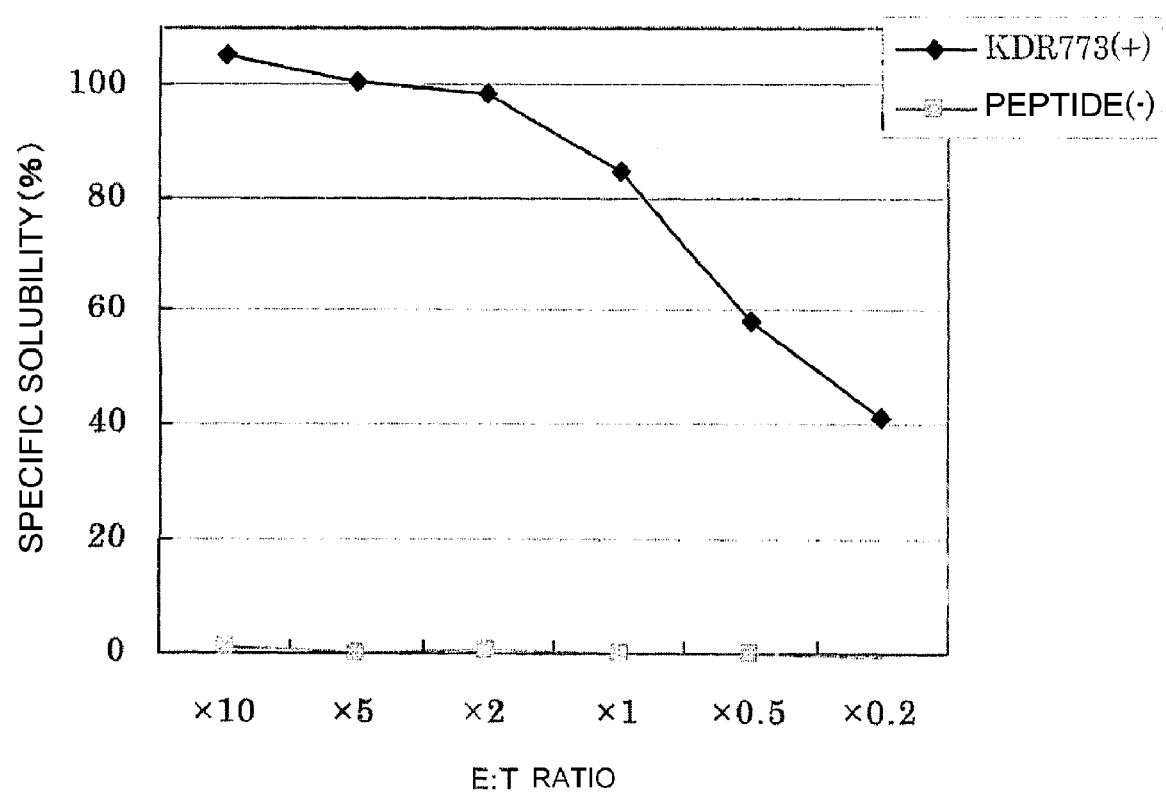
FIG. 14 shows the cytotoxic effect of CTL clone KDR C44-773-2L (KWC44-773-2L) on HLA-A0201-positive cells presenting peptides of this invention.

In the results, shown in FIG. 14, CTL clones obtained by stimulation with the modified peptide could recognize and damage the post-modification peptide.

Example 20

The cytotoxic effect of the CTL clone (KDR C44-773-2L (KWC44-773-2L)) against hepatocellular carcinoma cell line HLA-A0201-positive HePG2, forced by adenoviruses to express KDR, was examined by chromium release assay. HLA-A0201-positive HePG2 forced to express EGFP was used as control.

Figure 15:
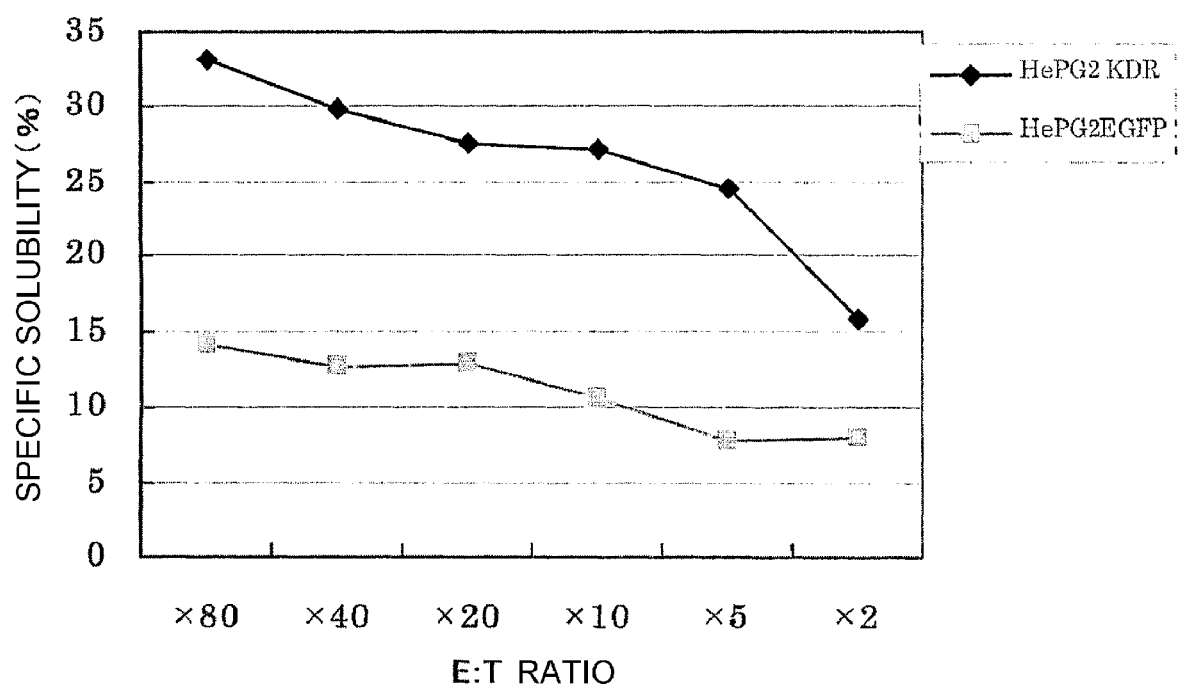
FIG. 15 shows the cytotoxic effect of CTL clone KDR C44-773-2L (KWC44-773-2L) on HLA-A0201-positive cells presenting KDR peptides.

In the results, shown in FIG. 15, CTL clone KDR C44-773-2L (KWC44-773-2L) showed remarkably high cytotoxic effect against HLA-A0201-positive cells presenting KDR peptides on the surface, compared to activity against cells presenting the EGFP peptide.

Example 21

The present inventors determined whether various antibodies can block the cytotoxic effect of the CTL clone (KDR C51-1328 (KWC51)), obtained from the peptide of SEQ ID NO:34, against hepatocellular carcinoma cell line HLA-A0201-positive HePG2, forced by adenoviruses to express KDR.

Figure 16:
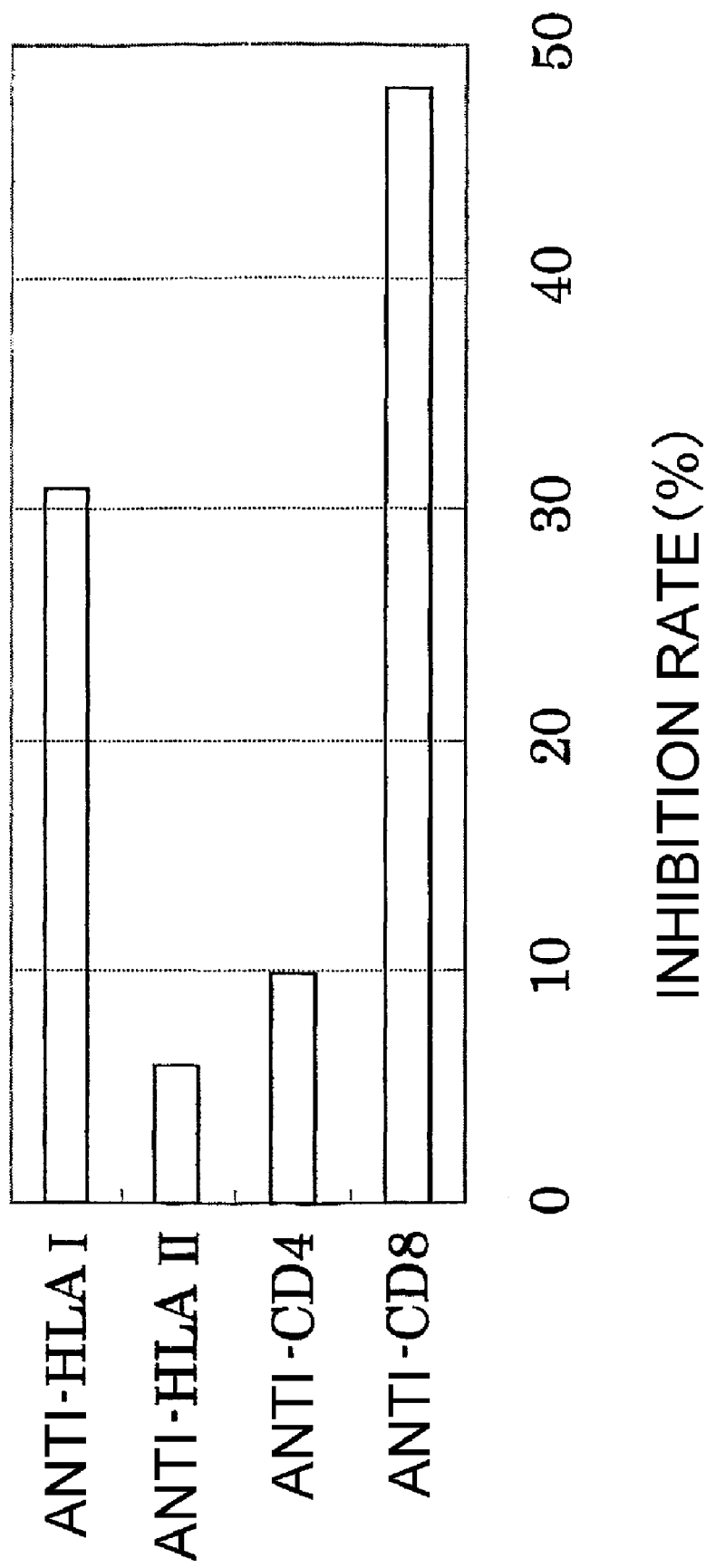
FIG. 16 shows the inhibitory effect of each type of antibody on the cytotoxic effect of the CTL clones.

In the results, shown in FIG. 16, cytotoxic function was inhibited by anti-HLA Class I antibody against HLA antigens displayed by target cells, and anti-CD8 antibody against CD8 used as a marker for cytotoxic T cells.

Example 22

Examination of Angiogenesis-Inhibiting Activity by Dorsal Air Sac (DAS) Assay

The actual angiogenesis-inhibiting activity of peptide epitopes was evaluated in mice using a DAS assay (see, Clinical Cancer Research, Vol. 5, 2185-2191, August 1999; Cancer Research 62, 6116-6123, Nov. 1, 2002).

Specifically, a membrane filter was fixed to both sides of a chamber ring, and sterilized with ethylene oxide gas. B16 melanoma cells were prepared to $5 \times 10^5$ cells/0.15 mL, and injected into the chamber. Mice (A2/kb transgenic mice (derived from B16)) were immobilized face down, and an air sac was produced by injecting 5 to 10 mL of air in to the murine dorsal hypoderm using a syringe. An approximately 1-cm incision was made to the lower part of the sac. The chamber ring, filled with cell suspension solution, was implanted in the dorsal hypoderm, and the skin was closed using a skin stapler. Six days after implantation, the mouse skin was decorticated together with the chamber, fixed in an extended form, and marked with a black rubber ring to observe the newly formed blood vessels using a microscope. Blood vessels that are newly formed by angiogenic factors released from malignant tumor cells characteristically run in a zigzag manner, and are morphologically different from naturally occurring background blood vessels. Therefore, blood vessels of 3-mm or longer within the rubber ring and running in a zigzag manner were determined to be newly formed blood vessels, and were evaluated using an angiogenesis index (AI). AIs was evaluated into six levels, from 0 to 5 according to the number of tortuous blood vessels. All those with five or more tortuous blood vessels were determined to be 5.

Vaccination was performed 14 days prior to chamber implantation, and repeated after one week (a total of two times) by respectively injecting $5 \times 10^4$ cells of HBSS, DC alone, or peptide-pulsed DC, to the tail vein. The results are shown in FIG. 17 and in Table 8, as shown below.

Figure 17:
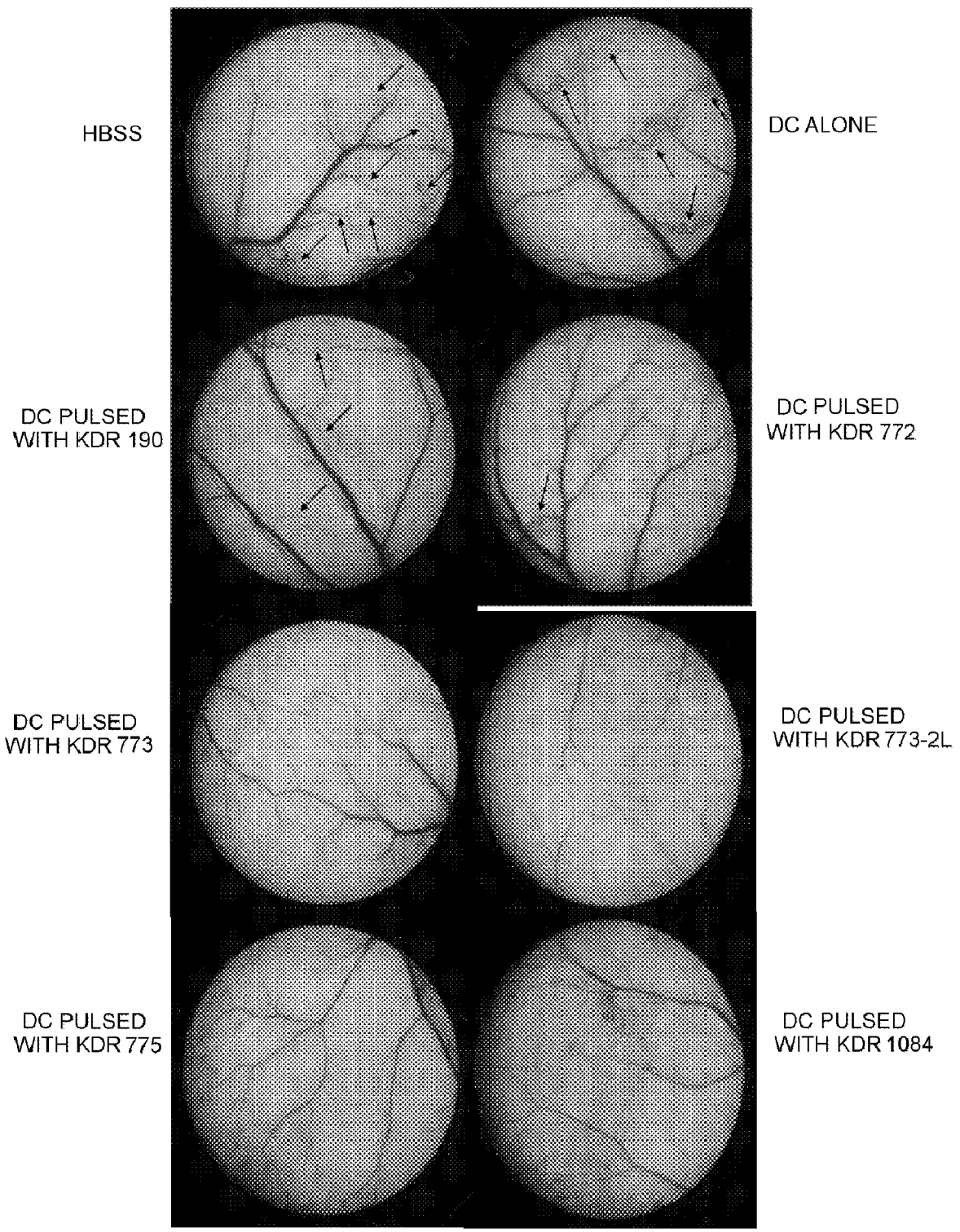
FIG. 17 shows the inhibitory activity of the peptides of this invention on the B16 cell-induced angiogenic response in A2/Kb TGM. Mice were vaccinated twice with HBSS, unpulsed DC, or DC pulsed with the epitope peptides of this invention (KDR190, KDR772, KDR773, KDR773-2L, KDR775, or KDR1084). The arrows indicate newly formed blood vessels, which run in a characteristic zigzag pattern.

FIG. 17 and Table 8 showed that the formation of tortuous blood vessels was clearly suppressed in the groups vaccinated with DCs pulsed with the peptides of SEQ ID NO:40 (amino acid initiation position KDR190), SEQ ID NO:33 (KDR772), SEQ ID NO:30 (KDR773), SEQ ID NO:54 (KDR773-2L), SEQ ID NO:29 (KDR775), and SEQ ID NO:46 (KDR1084), respectively, as compared to the group to which DC was administered alone. This indicated a statistically significant angiogenesis inhibitory effect.

Wound healing and fertility in vaccinated mice were analyzed in order to observe the adverse effects of vaccination using these epitope peptides on normal physiological angiogenesis. However, no significant adverse effects were found in the vaccinated mice. Furthermore, using CTL clones that recognize KDR peptides, cytotoxicity against non-proliferative or proliferative endothelial cells was tested in vitro to examine adverse effects in humans. As a result, these clones showed stronger activity against proliferative endothelial cells than against non-proliferative endothelial cells.

Example 23

Using A2/Kb transgenic mice expressing human HLA-A0201, the peptides of SEQ ID NO:30 (amino acid initiation position KDR773) and SEQ ID NO:34 (KDR1084) were each mixed with incomplete Freund's adjuvant, then administered on day 3 and 13 to colon cancer strain MC38-implanted tumor-bearing mice so as to indicate changes in tumor volume.

Figure 18:
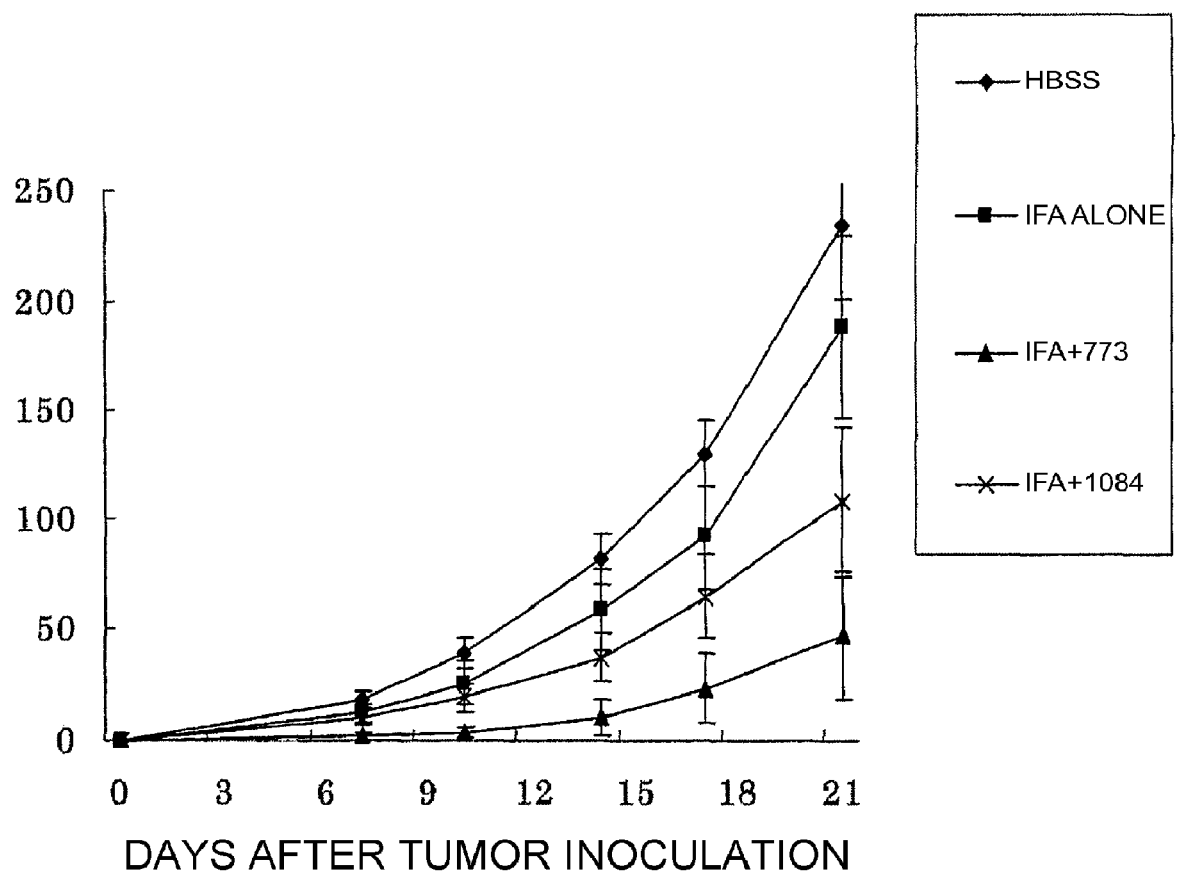
FIG. 18 shows the suppressive effect of the peptides of this invention on the increase in volume of human tumors in transgenic mice.

The in vivo anti-tumor effect in a therapeutic model of HLA-A*0201-immobilized epitope peptide (KDR773) was evaluated using the area of the tumor, using the same vaccination method as in Example 22. The result, as apparent from FIG. 18, confirm a significant tumor growth suppression effect by vaccination with the peptides of SEQ ID NO:30 and SEQ ID NO:34.

Example 24

The peptide of SEQ ID NO:40 (amino acid initiation position KDR190) was added to HLA-A0201-positive T2 strain to produce target cells. Using these cells, the cytotoxic effect of the CTL clone (KWC65-190) obtained from the peptide of SEQ ID NO:40 in Example 13 was examined using chromium release assay.

TABLE 8

Effect of DAS assay

| INOCULATION | PEPTIDE STIMULATION | | ANGIOGENESIS INDEX (AI) | P |
|---|---|---|---|---|
| VEHICLE | — | | (0.7 ± 0.2) | |
| HBSS | — | | (4.5 ± 0.2) | |
| DC | NONE | | (4.2 ± 0.4) | |
| DC | KDR190 | (SEQ ID NO: 40) | (3.6 ± 0.5) | 0.3453 |
| DC | KDR772 | (SEQ ID NO: 33) | (2.8 ± 0.5) | 0.0346 |
| DC | KDR773 | (SEQ ID NO: 30) | (2.2 ± 0.7) | 0.0034 |
| DC | KDR773-2L | (SEQ ID NO: 54) | (1.3 ± 0.5) | 0.0001 |
| DC | KDR775 | (SEQ ID NO: 29) | (2.2 ± 0.5) | 0.0007 |
| DC | KDR1084 | (SEQ ID NO: 46) | (1.7 ± 0.3) | <0.0001 |

Figure 19:
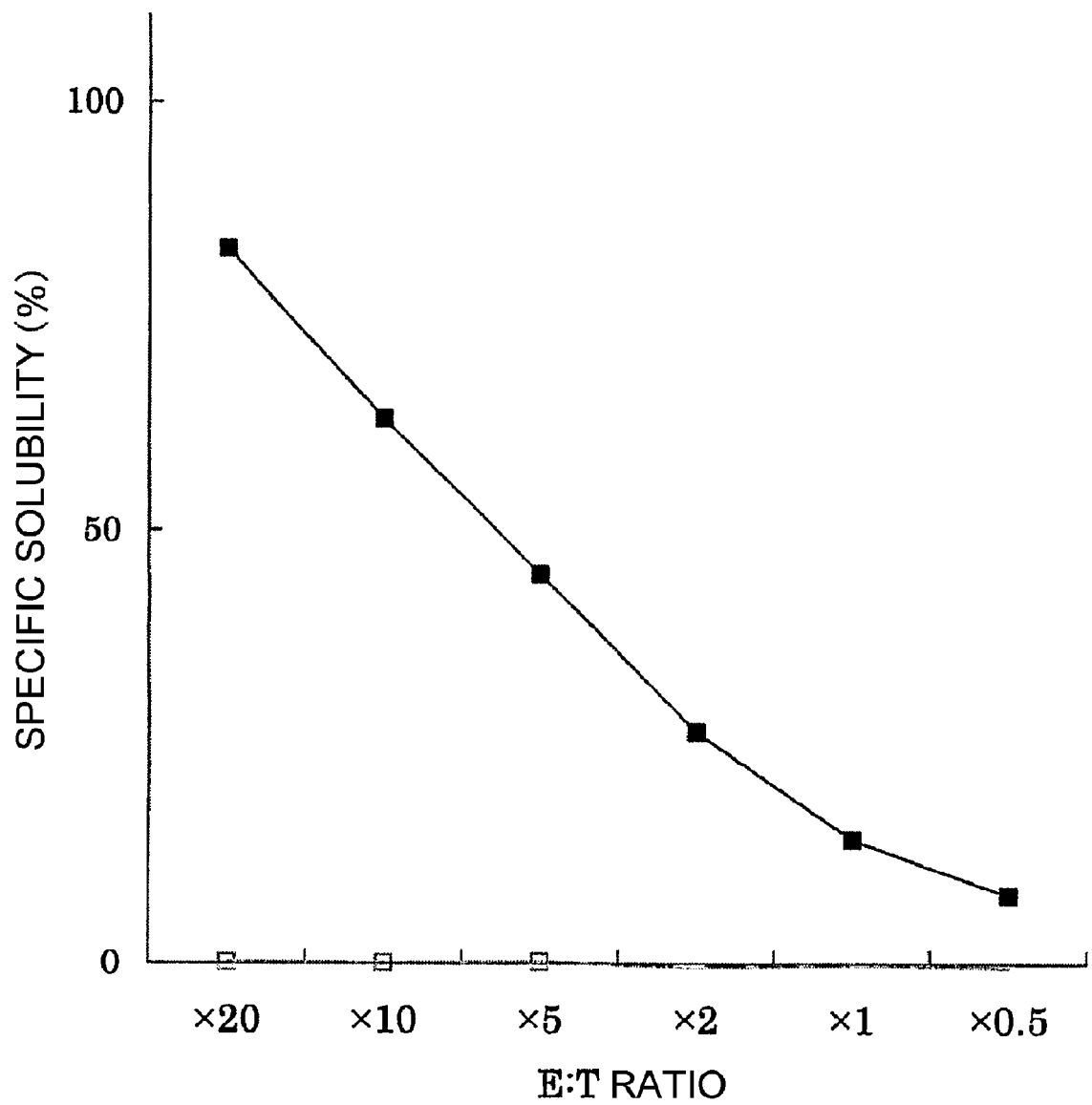
FIG. 19 shows the cytotoxic effect of CTL clone KWC65-190 on HLA-A0201-positive cells presenting peptides of this invention, in the presence (black boxes) or absence (white boxes) of the peptides.

In the results, shown in FIG. 19, CTL clone KWC65-190 clearly showed a cytotoxic effect against HLA-A0201-positive cells presenting the peptide of SEQ ID NO:40. In contrast, absolutely no cytotoxic effect was observed against control cells not presenting the peptide of SEQ ID NO:40.

Example 25

The peptide of SEQ ID NO:33 (amino acid initiation position KDR772) was added to HLA-A0201-positive T2 strain to produce target cells. Using these cells, the cytotoxic effect of the CTL clone (KWC72-772) obtained from the peptide of SEQ ID NO:33 in Example 13 was examined using a chromium release assay.

Figure 20:
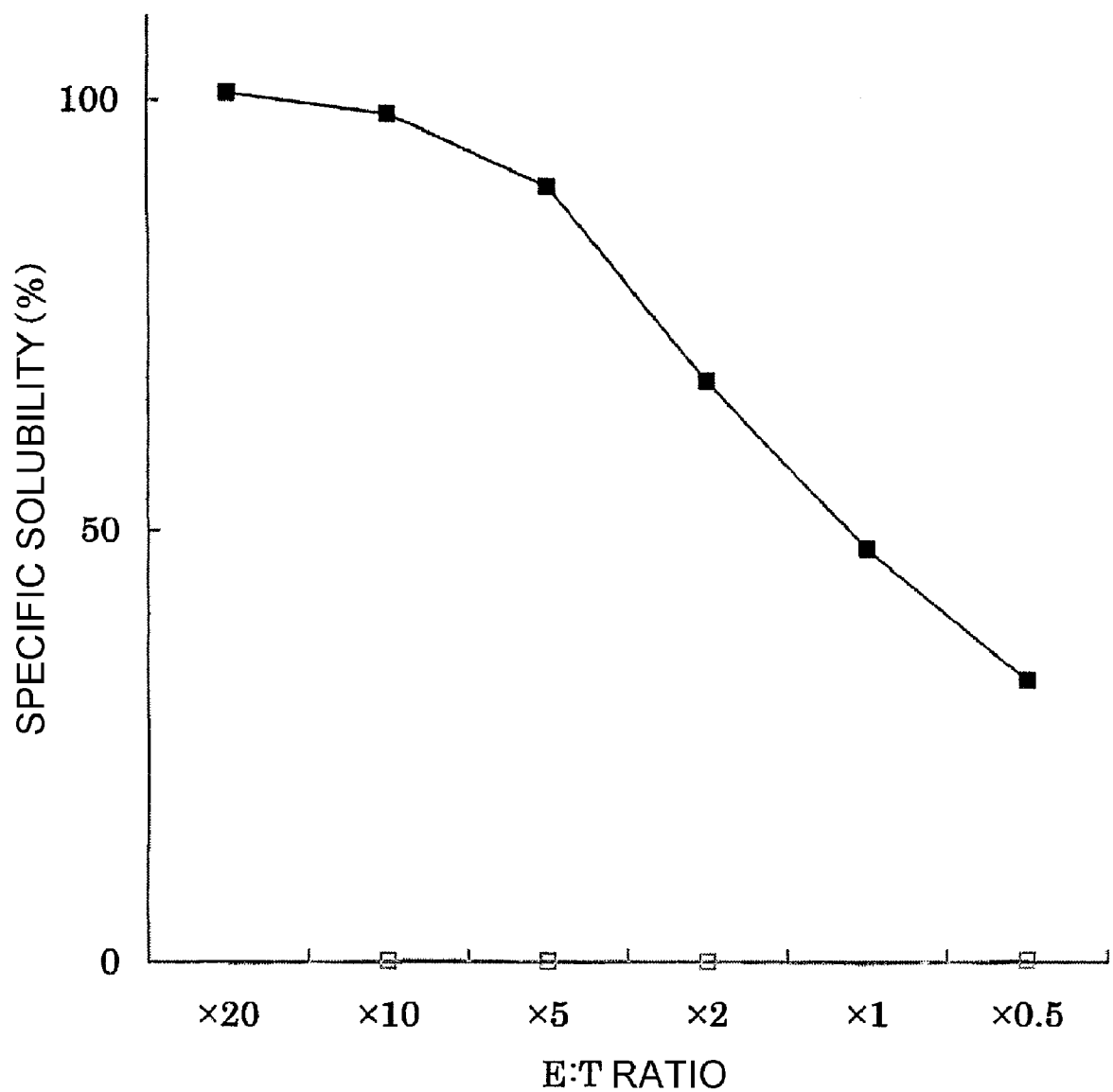
FIG. 20 shows the cytotoxic effect of CTL clone KWC72-772 on HLA-A0201-positive cells presenting peptides of this invention, in the presence (black boxes) or absence (white boxes) of the peptides.

In the results, shown in FIG. 20, CTL clone KWC72-772 clearly showed a cytotoxic effect against HLA-A0201-positive cells presenting the peptide of SEQ ID NO:33. In contrast, absolutely no cytotoxic effect was observed against control cells that did not present the peptide of SEQ ID NO:33.

Example 26

The cytotoxic effect of the CTL clone (KWC72-772) against hepatocellular carcinoma cell line HLA-A0201-positive HePG2, forced by adenoviruses to express KDR, was examined by chromium release assay. HLA-A0201-positive HePG2 forced to express EGFP was used as control.

Figure 21:
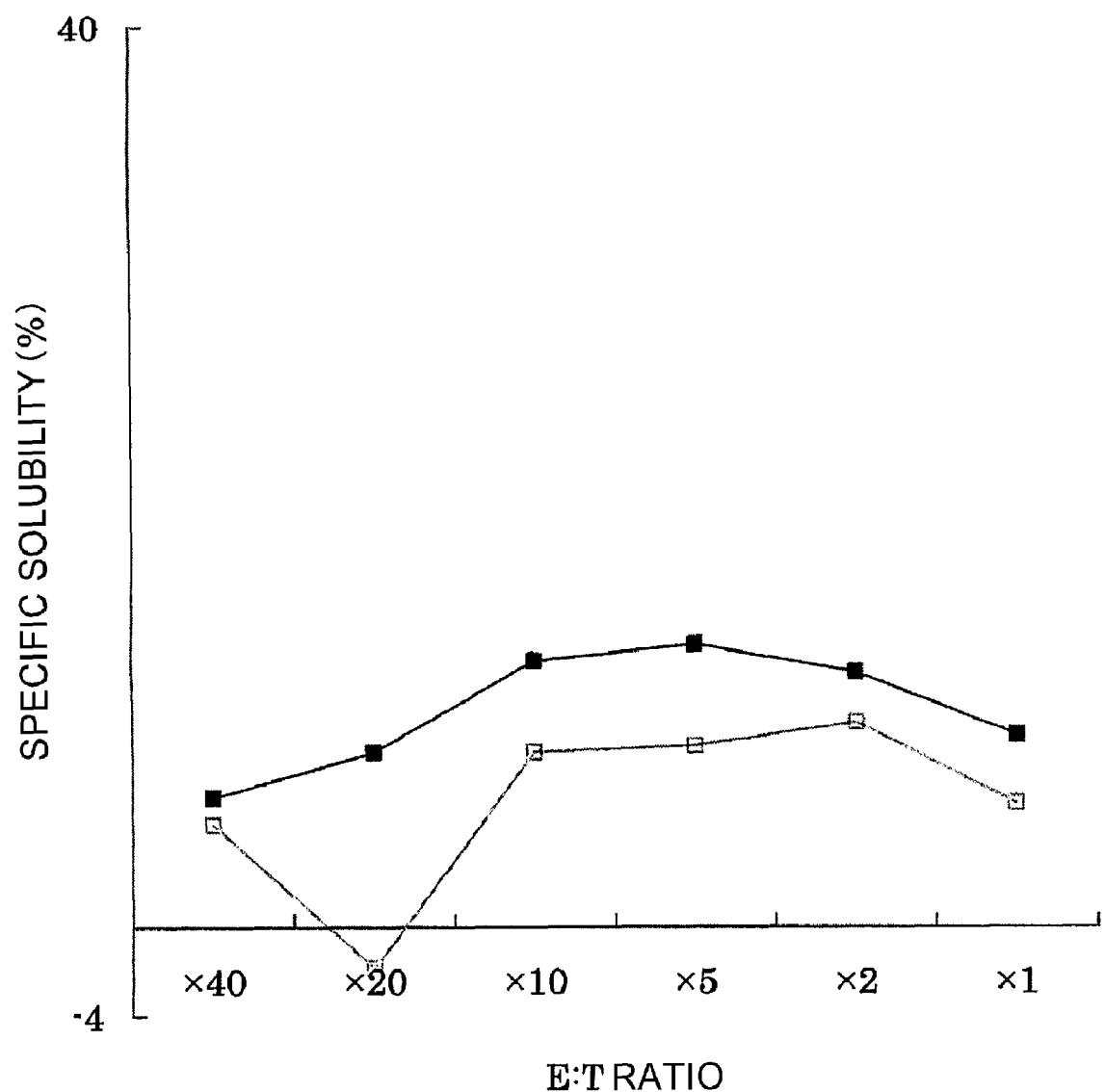
FIG. 21 shows the cytotoxic effect of CTL clone KWC72-772 on HLA-A0201-positive cells presenting KDR peptides. HePG2-VEGFR2: black boxes; HePG2-EGFP: white boxes.
Figure 22:
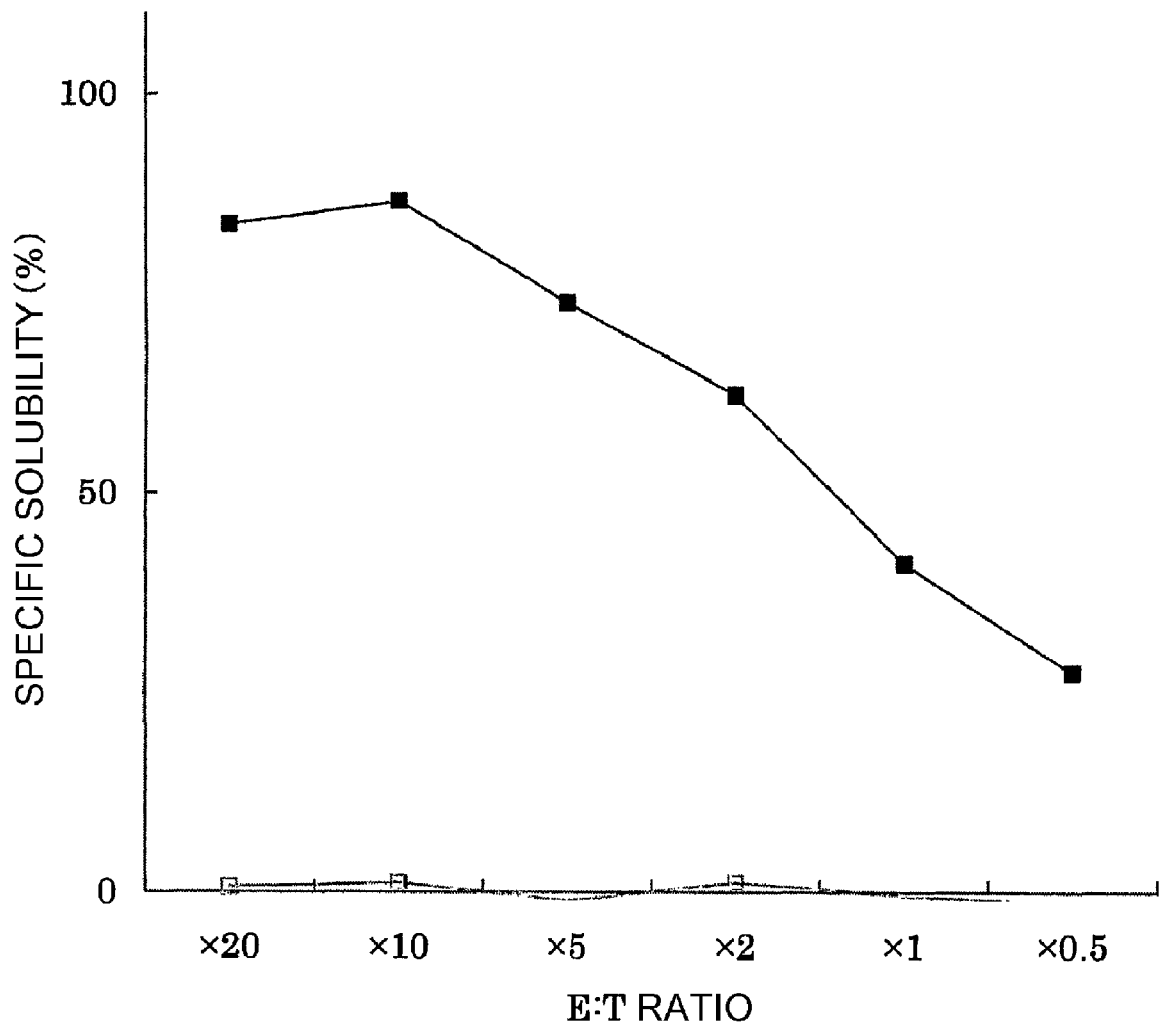
FIG. 22 shows the cytotoxic effect of CTL clone C7-1318 on HLA-A24-positive cells presenting peptides of this invention, in the presence (black boxes) or absence (white boxes) of the peptides.
Figure 23:
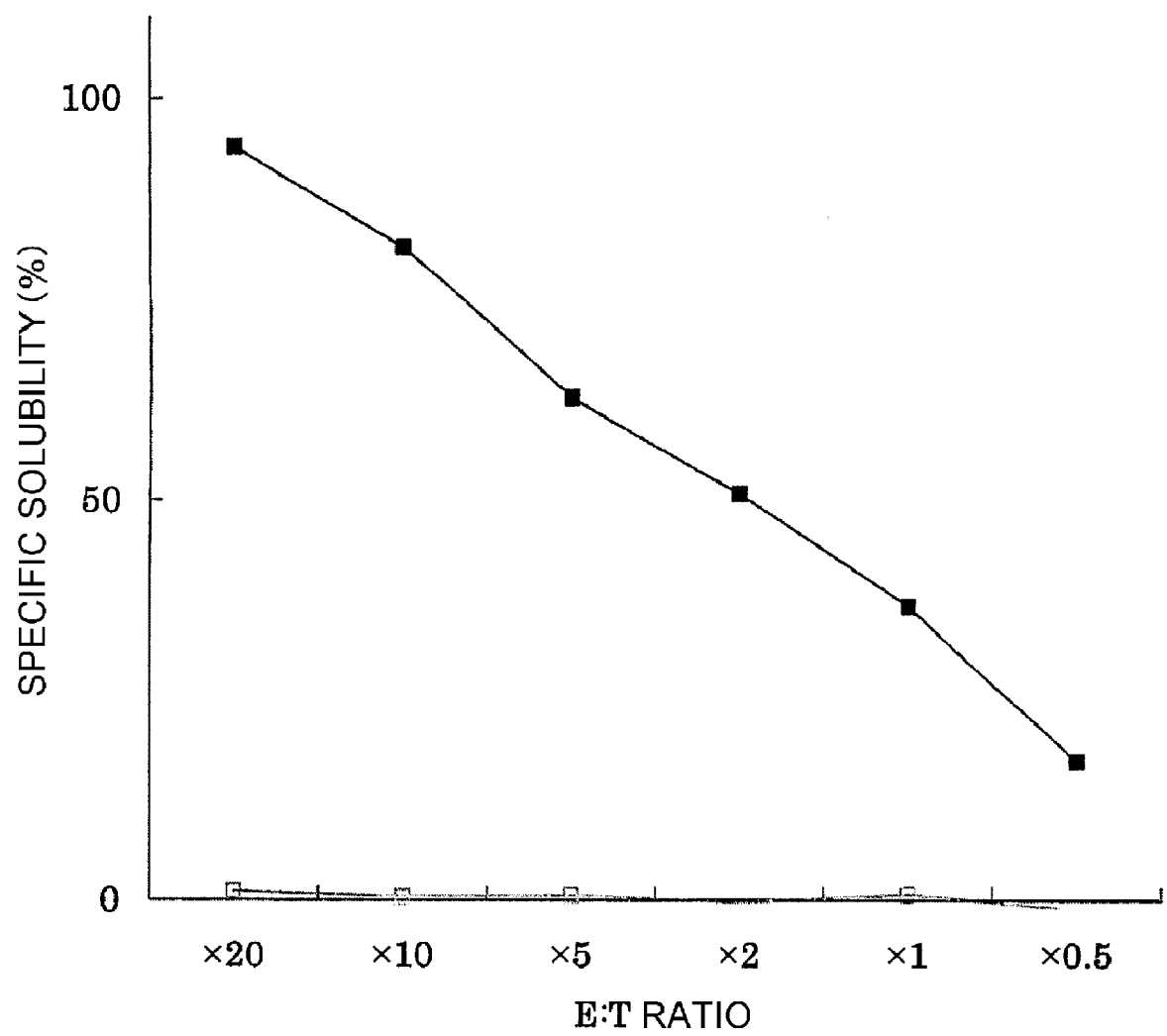
FIG. 23 shows the cytotoxic effect of CTL clone KWC46 on HLA-A24-positive cells presenting peptides of this invention, in the presence (black boxes) or absence (white boxes) of the peptides.
Figure 24:
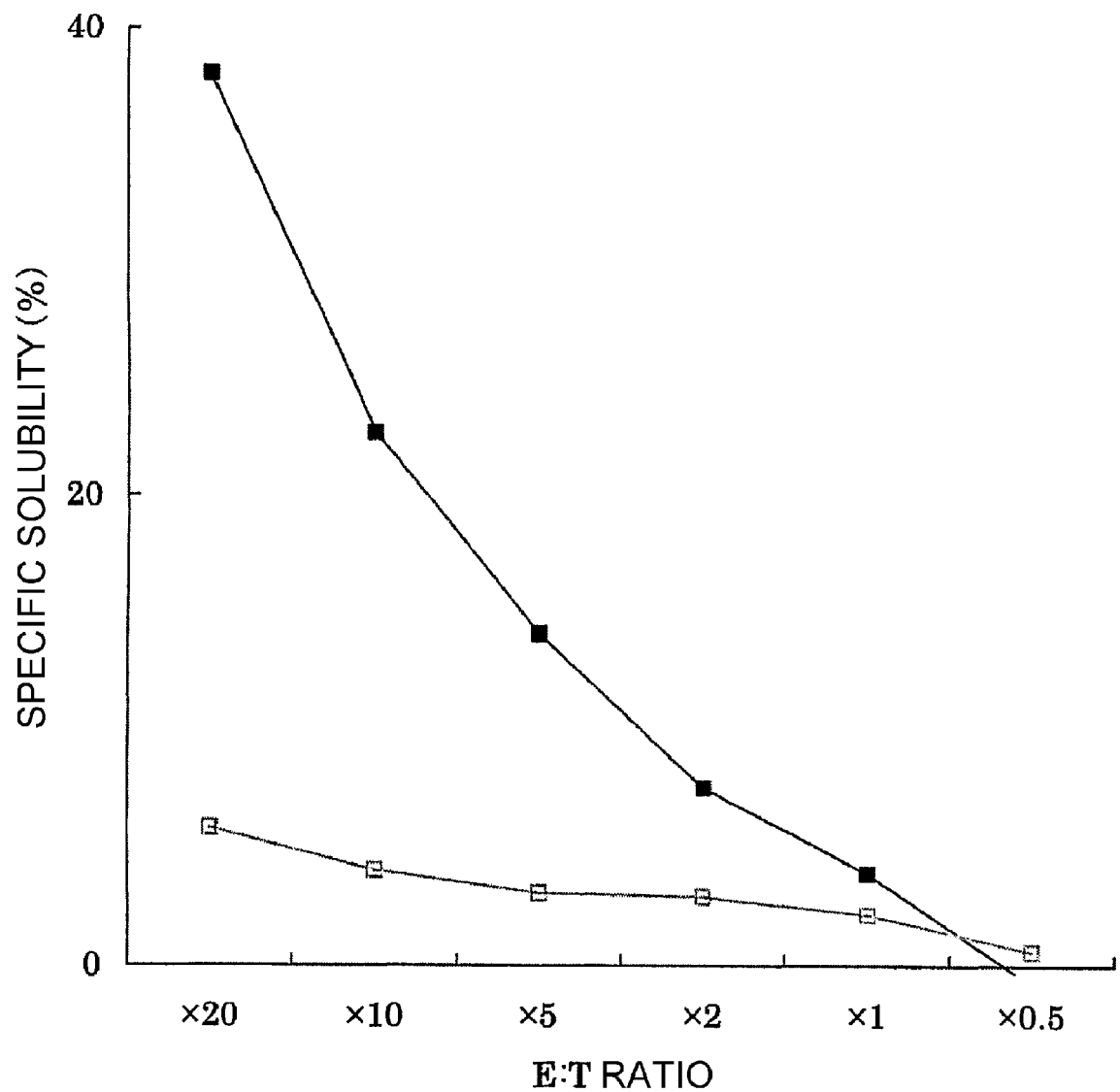
FIG. 24 shows the cytotoxic effect of CTL clone C18-189 on HLA-A24-positive cells presenting peptides of this invention, in the presence (black boxes) or absence (white boxes) of the peptides.
Figure 25:
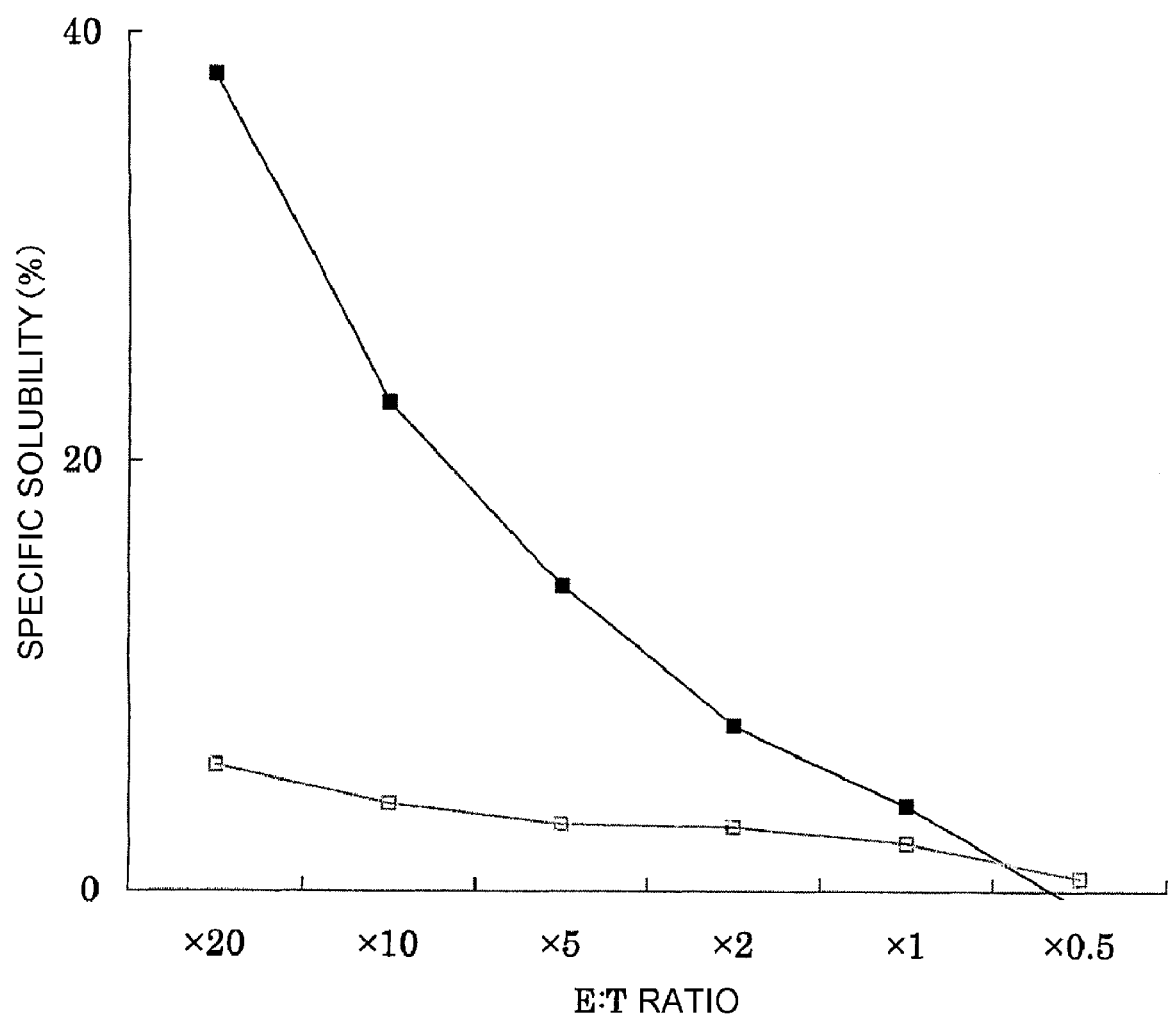
FIG. 25 shows the cytotoxic effect of CTL clone C65-826 on HLA-A24-positive cells presenting peptides of this invention, in the presence (black boxes) or absence (white boxes) of the peptides.
Figure 26:
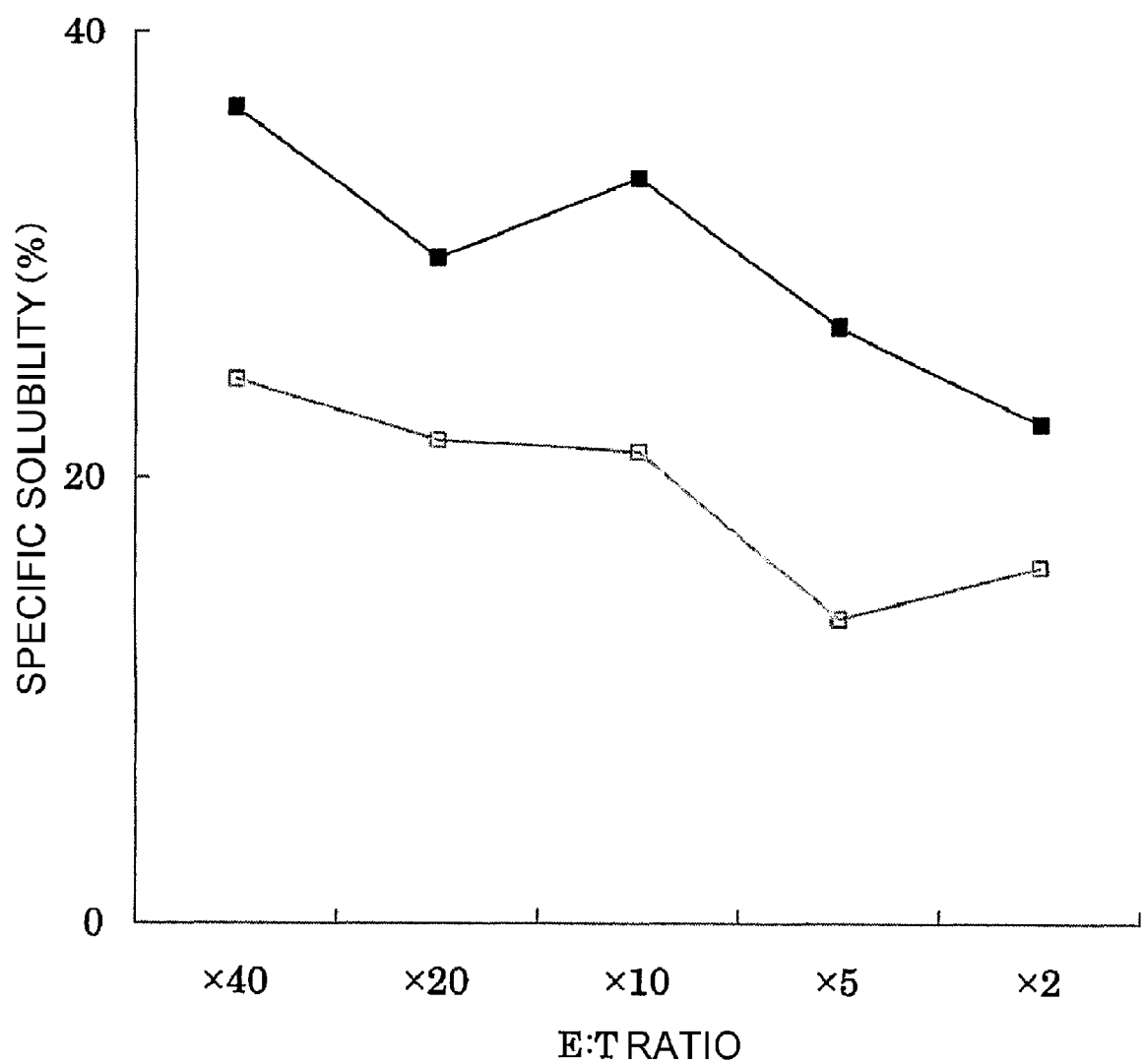
FIG. 26 shows the cytotoxic effect of CTL clone C7-1318 on HLA-A24-positive cells presenting peptides of this invention. HT29-VEGFR2: black boxes; HT29-EGFP: white boxes.
Figure 27:
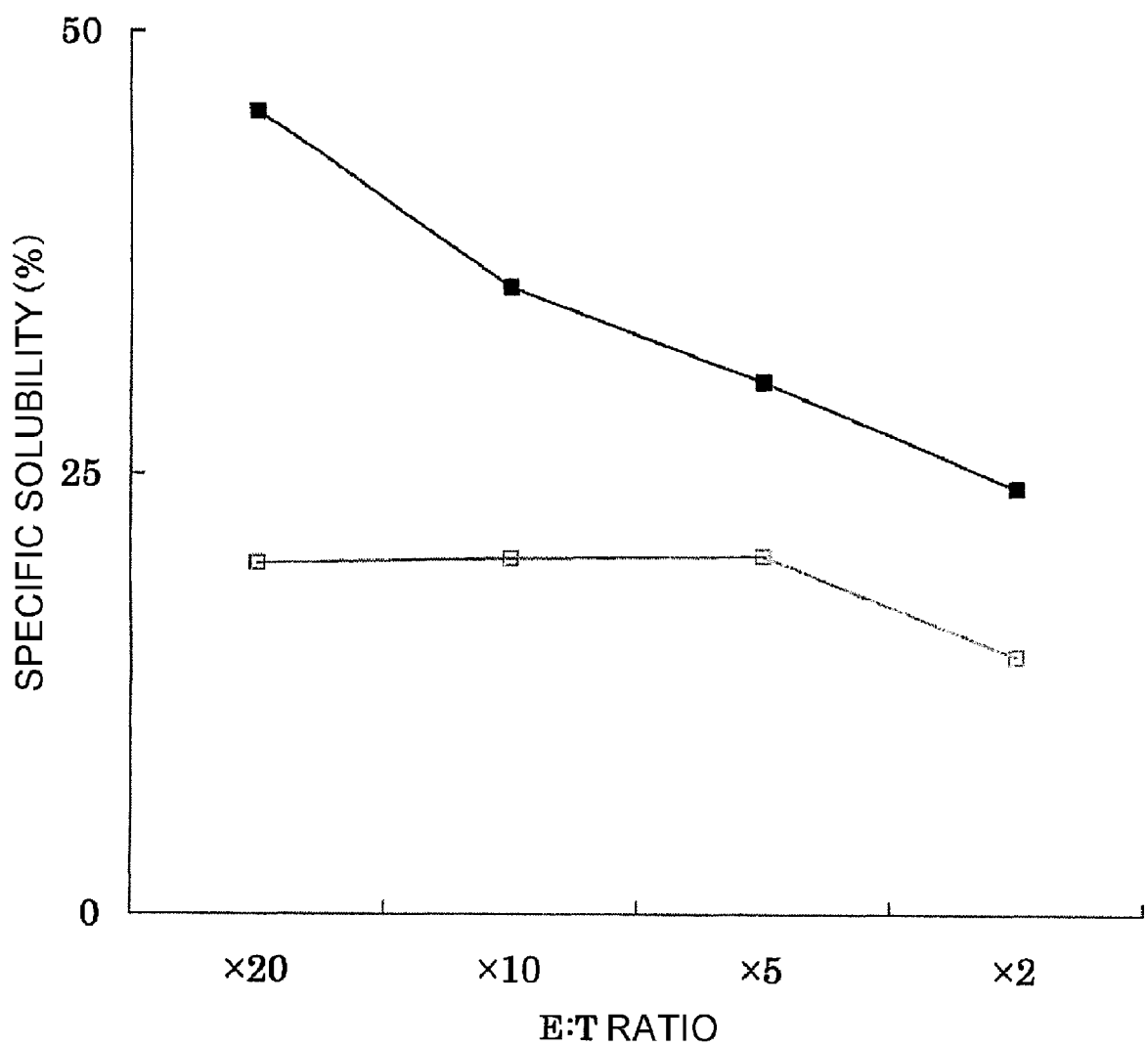
FIG. 27 shows the cytotoxic effect of CTL clone KWC46 on HLA-A24-positive cells presenting peptides of this invention. HT29-VEGFR2: black boxes; HT29-EGFP: white boxes.
Figure 28:
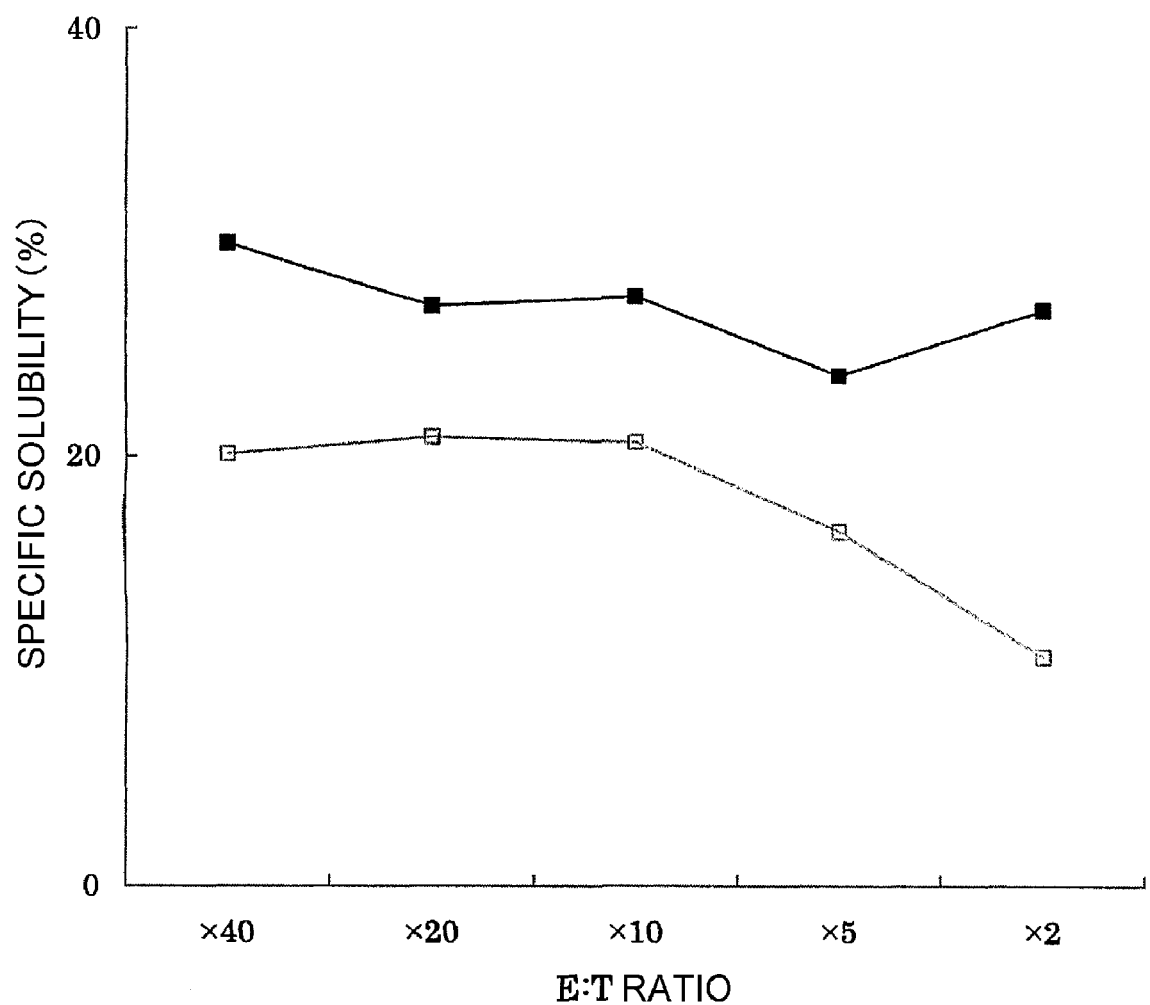
FIG. 28 shows the cytotoxic effect of CTL clone C18-189 on HLA-A24-positive cells presenting peptides of this invention. HT29-VEGFR2: black boxes; HT29-EGFP: white boxes.
Figure 29:
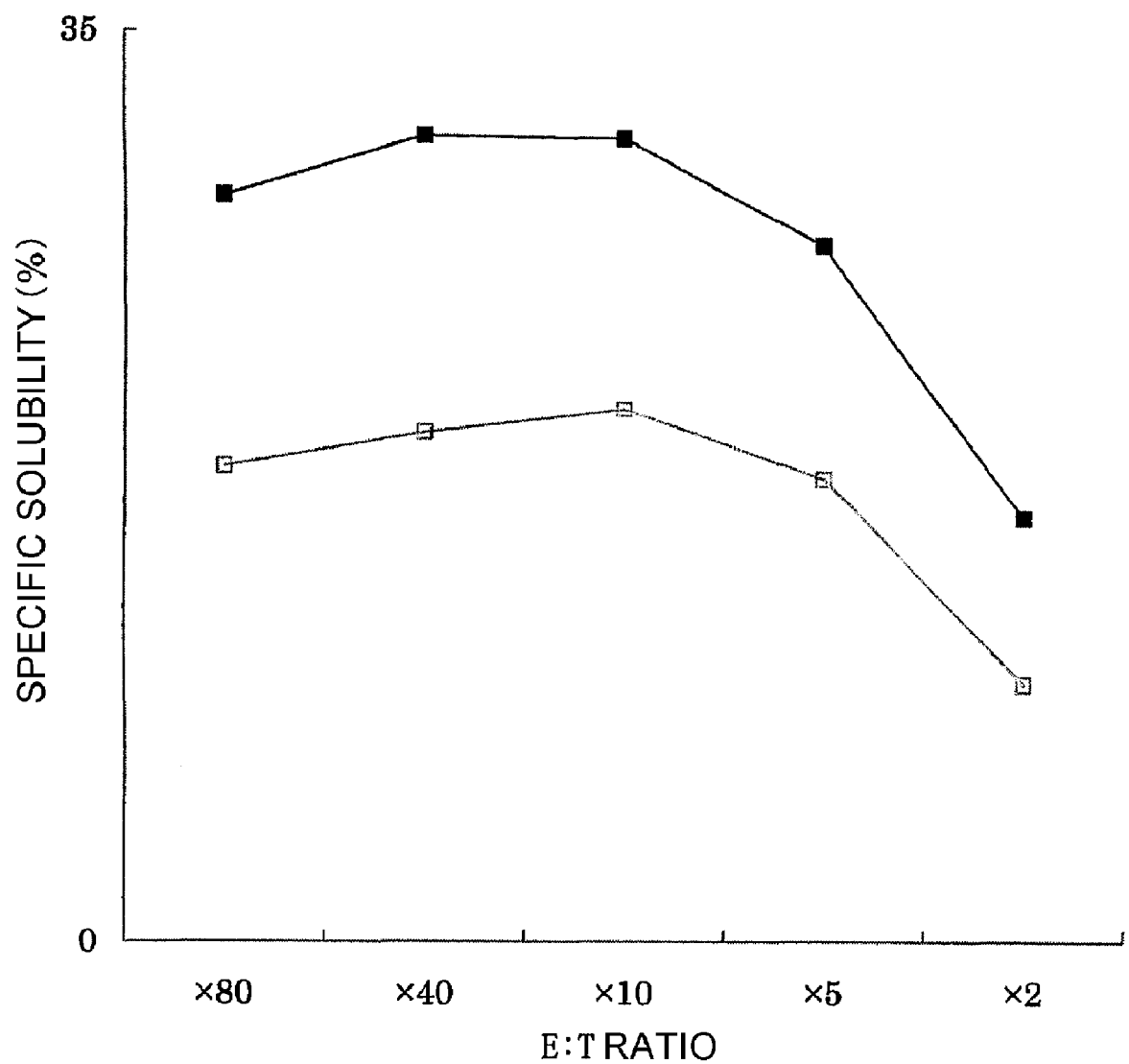
FIG. 29 shows the cytotoxic effect of CTL clone C65-826 on HLA-A24-positive cells presenting peptides of this invention. HT29-VEGFR2: black boxes; HT29-EGFP: white boxes.

In the results, as shown in FIG. 21, CTL clone KWC72-772 showed remarkably high cytotoxic effect against HLA-A0201-positive cells presenting KDR peptides on their surface, as compared to activity against cells presenting the EGFP peptide.

Example 27

The peptides of SEQ ID NO:2 (amino acid initiation position KDR1318), SEQ ID NO:3 (KDR220), SEQ ID NO:5 (KDR189), and SEQ ID NO:11 (KDR826) were added to HLA-A24-positive human B-lymphocyte strain A24-LCL (HLA-A24/24, Takara Shuzo) to produce target cells. Using these cells, the cytotoxic effects of CTL clones, C7-1318, KWC46, C18-189, and C65-826, described in Example 3, were examined by chromium release assay.

In the results, shown in FIGS. 22 to 25, each of the CTL clones, C7-1318, KWC46, C18-189, and C65-826, clearly showed a cytotoxic effect against each of the HLA-A24-positive cells presenting the peptides of SEQ ID NOs:2, 3, 5, and 11, respectively. In contrast, hardly any or absolutely no cytotoxic effect was observed against each of the control cells, which did not present the peptides.

Example 28

As for Example 11, the cytotoxic effects of the CTL clones, C7-1318, KWC46, C18-189, and C65-826, described in Example 3, against human colon cancer HT29 strain (ATCC), forced by adenoviruses to express KDR, were examined by chromium release assay. HLA-A24-positive HT29 strain forcedly expressing EGFP was used as a control.

In the results, shown in FIGS. 26 to 29, all CTL clones, C7-1318, KWC46, C18-189, and C65-826, showed remarkably high cytotoxic effect against HLA-A24-positive HT29 forcedly expressing KDR, compared to activity against cells forcedly expressing EGFP.

Example 29

As for Example 22, the angiogenesis inhibitory activity of peptide epitopes against the angiogenic response induced by Colon 26 cells in BALB/c mice was evaluated by DAS assay.

Figure 30:
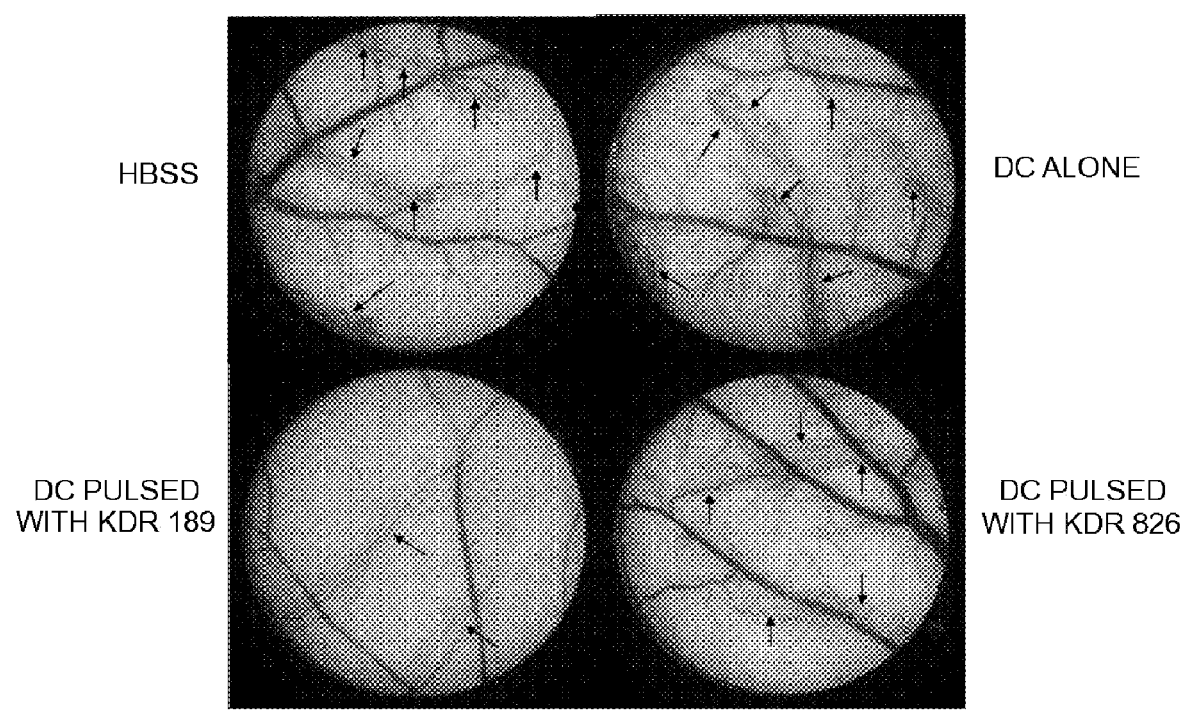
FIG. 30 shows the inhibitory activity of the peptides of this invention on the Colon 26 cell-induced angiogenic response in BALB/c mice. The mice were vaccinated twice with HBSS, unpulsed DC, or DC pulsed with an epitope peptide of this invention (KDR189 or KDR826). The arrows indicate newly formed blood vessels, which run in a characteristic zigzag pattern.
Figure 31:
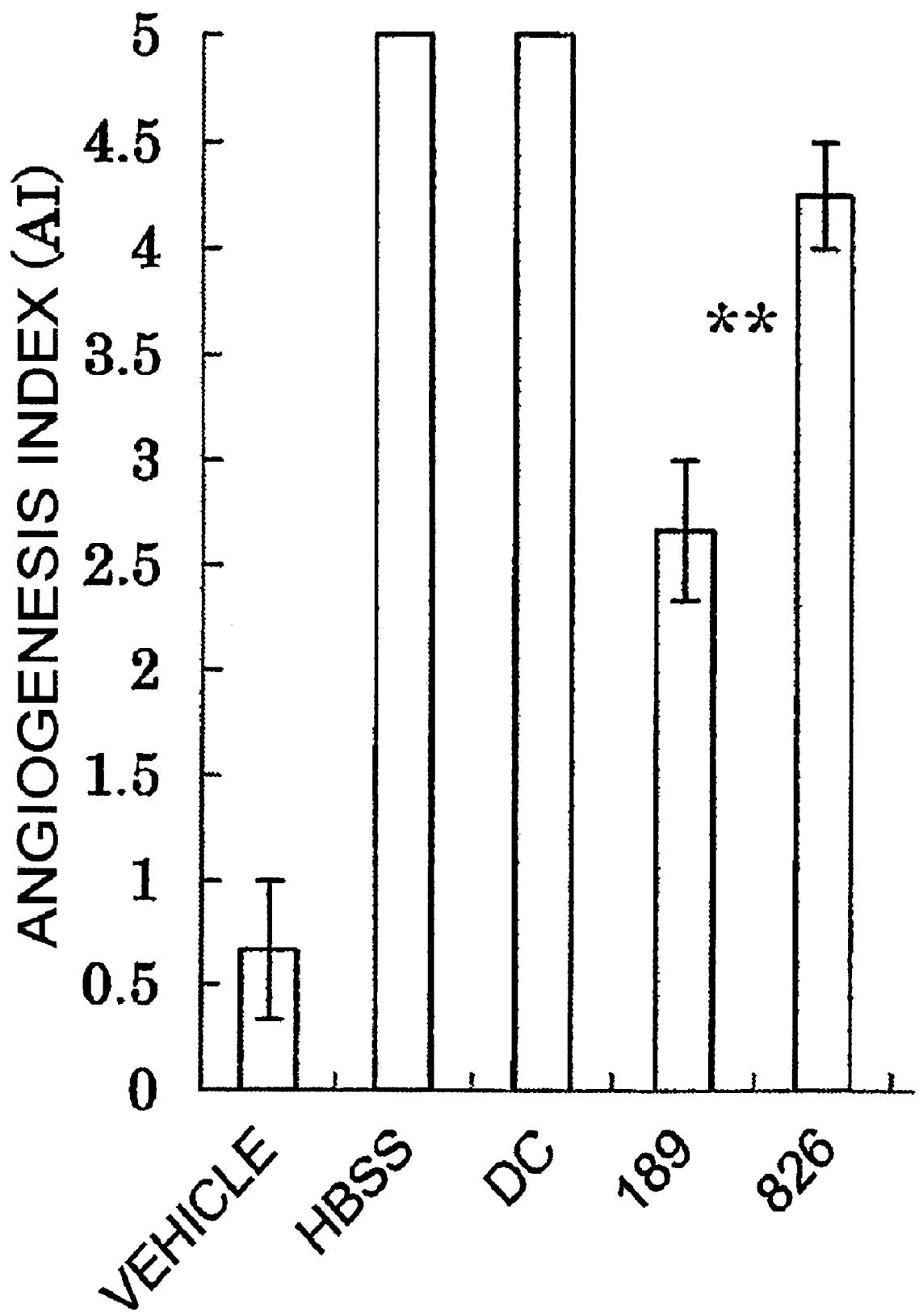
FIG. 31 shows the inhibition of Colon 26 cell-induced angiogenic response in BALB/c by the peptides of this invention. The bars indicate the average, and the vertical error bars indicate standard error.

As apparent from the results of FIGS. 30 and 31, in the groups vaccinated with DCs pulsed with the peptides of SEQ ID NO:5 (amino acid initiation position KDR189) and SEQ ID NO:11 (KDR826), respectively, the formation of tortuous blood vessels was clearly suppressed as compared to the group administered with DC alone. This indicated a statistically significant angiogenesis suppression effect.

Example 30

The CTL response against each type of following epitope peptides was investigated using PBMC of cancer patients after stimulation with each peptide:

Peptides of SEQ ID NO:8 (amino acid initiation position KDR169), SEQ ID NO:5 (KDR189), SEQ ID NO:3 (KDR220), SEQ ID NO:11 (KDR826), and SEQ ID NO:17 (KDR1318), with high HLA-24 binding affinity; and peptides of SEQ ID NO:40 (KDR190), SEQ ID NO:33 (KDR772), SEQ ID NO:30 (KDR773), SEQ ID NO:29 (KDR775), and SEQ ID NO:34 (KDR1328), with high HLA-A0201 binding affinity.

Using the method reported by Maeda, Y. et al., Br. J. Cancer, 87:796-804 (2002), peptide-specific CTLs were detected in PBMC. First, PBMC collected from patients ($1 \times 10^5$ cells) were incubated with 10 µM of each peptide in a U-shaped bottom 96-well plate comprising 200 µL medium. The medium consisted of 45% RPMI1640 medium, 45% AIM-V medium, 10% FBS, 100 U/mL interleukin-2 (IL-2), and 0.1 µM MEM non-essential amino acid solution. Every three days, half of the medium was removed and replaced with fresh medium containing the corresponding peptide (20 µM). After incubation for twelve days, cells were collected to test IFN-γ production ability in response to each peptide. When the amount of IFN-γ produced by peptide-stimulated PBMC in response to a corresponding peptide was two times or more than the amount produced in response to the control HIV peptide, that test peptide was deemed positive.

These results showed that a CTL precursor is produced in HLA-A2- and HLA-A24-type cancer patients, as in a healthy donor (Table 9). In the table, patients A, B, and C are HLA-A24-type patients; and patient D is an HLA-A02-type patient. Patients A and D are colon cancer patients; and patients B and C are melanoma patients. CMVs refer to the cytomegalovirus-derived peptides used as positive controls. The peptides with high A-24 binding affinity are described in Kuzushima, K. et al., Blood 2001, 98(6):p 1872-1881, and such; and the peptides with high A-2 binding affinity are described in Solache, A. et al., J. Immunol. 1999, 163(10); p 5512-5518, and such.

TABLE 9

| | Cancer patient-derived CTL precursor | | | | | | | | |
|---|---|---|---|---|---|---|---|---|---|
| | PATIENT A | | PATIENT B | | PATIENT C | | | PATIENT D | |
| | POSITIVE WELLS | TOTAL WELLS | POSITIVE WELLS | TOTAL WELLS | POSITIVE WELLS | TOTAL WELLS | | POSITIVE WELLS | TOTAL WELLS |
| CMV | 1 | 32 | 1 | 24 | 0 | 16 | CMV | 5 | 20 |
| KDR 169 | 12 | 32 | 4 | 32 | 1 | 24 | KDR 190 | 3 | 24 |
| KDR 189 | 3 | 32 | 1 | 32 | 0 | 24 | KDR 772 | 3 | 24 |
| KDR 220 | 0 | 32 | 3 | 32 | 0 | 24 | KDR 773 | 1 | 24 |
| KDR 826 | 11 | 32 | 3 | 32 | 0 | 24 | KDR 775 | 2 | 24 |
| KDR 1318 | 0 | 32 | 9 | 32 | 1 | 24 | KDR 1328 | 0 | 24 |

Figure 32:
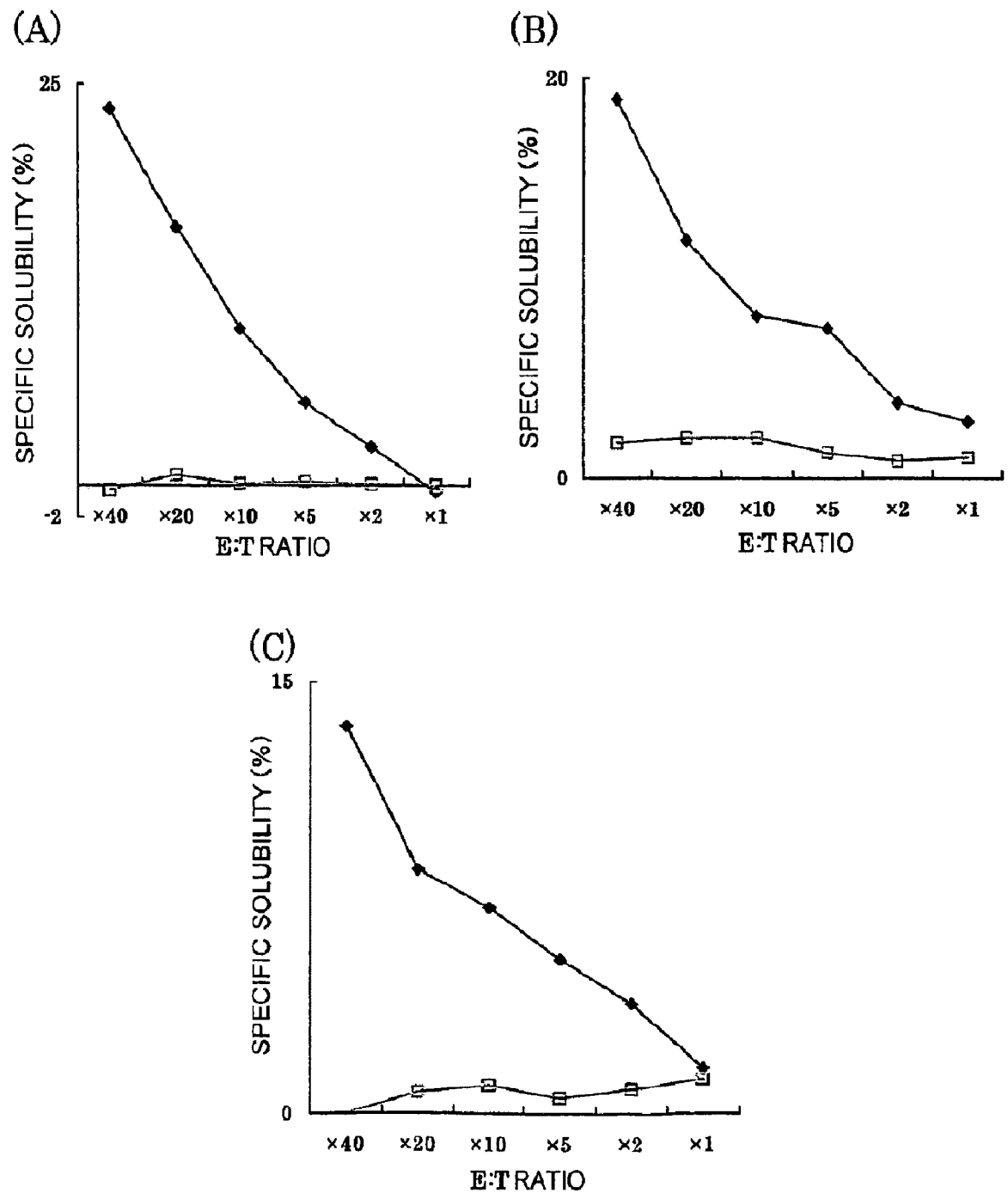
FIG. 32 shows the cytotoxic effect of CTL, derived from patients stimulated with the peptides of this invention, on HLA-A24-positive cells, in the presence (black diamonds) or absence (white squares) of the peptides.

As for Example 14 and the like, a standard $^{51}$Cr release assay was performed for four hours to establish CTL lines from the CTL precursors (FIG. 32).

INDUSTRIAL APPLICABILITY

The present invention provides novel peptides, which induce cytotoxic T cells by targeting the endothelial cells formed in a wide range of tumoral tissues, and which are extremely effective as cancer vaccines. The present invention also provides pharmaceuticals for treating and preventing tumors, where the pharmaceuticals comprise these peptides.

All publications, patents, and patent applications cited herein are incorporated into the present description by reference.

What is claimed is:

1. A nonapeptide or decapeptide selected from peptides consisting of the amino acid sequence of SEQ ID NO: 34, 40, and 46.

2. A peptide with cytotoxic T cell inducibility, wherein zero, one or two amino acids are substituted in the amino acid sequence of SEQ ID NO: 34, 40, or 46, wherein the peptide binds to an HLA-A02 restricted T cell receptor and induces a CTL response.

3. The peptide of claim 2, wherein the second amino acid from the N-terminus of SEQ ID NO: 34 or 40 is leucine or methionine.

4. The peptide of claim 2 or 3, wherein the C-terminal amino acid of SEQ ID NO: 40 or 46 is leucine or valine.

5. A composition comprising one or more peptides selected from the group consisting of:

(a) a nonapeptide or decapeptide selected from peptides consisting of the amino acid sequence of SEQ ID NO: 34, 40, and 46, (b) a peptide with cytotoxic T cell inducibility, wherein zero, one, or two amino acids are substituted in the amino acid sequence of SEQ ID NO: 34, 40, or 46, wherein the peptide binds to an HLA-A02 restricted T cell receptor and induces a CTL response, (c) the peptide of (b), wherein the second amino acid from the N-terminus of SEQ ID NO: 34 or 40 is leucine or methionine, and (d) the peptide of (b) or (c), wherein the C-terminal amino acid of SEQ ID NO: 40 or 46 is leucine or valine.

6. A method for inducing in vitro an antigen-presenting cell with high cytotoxic T cell inducibility, wherein said method comprises contacting said cell with a peptide selected from the group consisting of:

(a) a nonapeptide or decapeptide selected from peptides consisting of the amino acid sequence of SEQ ID NO: 34, 40, and 46, (b) a peptide with cytotoxic T cell inducibility, wherein zero, one, or two amino acids are substituted in the amino acid sequence of SEQ ID NO: 34, 40, or 46, wherein the peptide binds to an HLA-A02 restricted T cell receptor and induces a CTL response, (c) the peptide of (b), wherein the second amino acid from the N-terminus of SEQ ID NO: 34 or 40 is leucine or methionine, and (d) the peptide of (b) or (c), wherein the C-terminal amino acid of SEQ ID NO: 40 or 46 is leucine or valine.

7. A method for inducing in vitro a cytotoxic T cell, wherein said method comprises stimulating said cell with an antigen-presenting cell contacted with a peptide selected from the group consisting of:

(a) a nonapeptide or decapeptide selected from peptides consisting of the amino acid sequence of SEQ ID NO: 34, 40, and 46, (b) a peptide with cytotoxic T cell inducibility, wherein zero, one, or two amino acids are substituted in the amino acid sequence of SEQ ID NO: 34, 40, or 46, wherein the peptide binds to an HLA-A02 restricted T cell receptor and induces a CTL response, (c) the peptide of (b), wherein the second amino acid from the N-terminus of SEQ ID NO: 34 or 40 is leucine or methionine, and (d) the peptide of (b) or (c), wherein the C-terminal amino acid of SEQ ID NO: 40 or 46 is leucine or valine.

8. A composition for inhibiting angiogenesis at a diseased site, wherein the composition comprises a peptide selected from the group consisting of:

(a) a nonapeptide or decapeptide selected from peptides consisting of the amino acid sequence of SEQ ID NO: 46, (b) the peptide of (a), wherein the C-terminal amino acid of SEQ ID NO: 46 is valine, as an active ingredient.

9. The composition of claim 8, which is used for administration to a subject whose HLA antigen is HLA-A02.

10. The composition of claim 8, which is used to suppress the growth and/or metastasis of malignant tumors.

11. The composition of claim 9, which is used to suppress the growth and/or metastasis of malignant tumors.

* * * * *